(12) United States Patent
Chatterjee et al.

(10) Patent No.: US 12,201,657 B2
(45) Date of Patent: Jan. 21, 2025

(54) ADENO-ASSOCIATED VIRUS COMPOSITIONS FOR RESTORING HBB GENE FUNCTION AND METHODS OF USE THEREOF

(71) Applicant: CITY OF HOPE, Duarte, CA (US)

(72) Inventors: Saswati Chatterjee, Altadena, CA (US); Kamehameha K. Wong, Jr., Altadena, CA (US); Marwa BenHajSalah, Duarte, CA (US); Laura Jane Smith, Westford, MA (US); Albert Barnes Seymour, Westborough, MA (US); Jason Boke Wright, Concord, MA (US); James Anthony McSwiggen, Arlington, MA (US); Serena Nicole Dollive, Waltham, MA (US); Thia Baboval St. Martin, Lunenburg, MA (US); Jaime Michelle Prout, Hudson, NH (US)

(73) Assignee: CITY OF HOPE, Duarte, CA (US)

( * ) Notice: Subject to any disclaimer, the term of this patent is extended or adjusted under 35 U.S.C. 154(b) by 1143 days.

(21) Appl. No.: 16/163,061

(22) Filed: Oct. 17, 2018

(65) Prior Publication Data
US 2019/0134118 A1 May 9, 2019

Related U.S. Application Data

(60) Provisional application No. 62/621,102, filed on Jan. 24, 2018, provisional application No. 62/574,163, filed on Oct. 18, 2017.

(51) Int. Cl.
| | | |
|---|---|---|
| *A61K 35/761* | (2015.01) | |
| *A61K 48/00* | (2006.01) | |
| *C07K 14/075* | (2006.01) | |
| *C07K 14/805* | (2006.01) | |
| *C12N 15/62* | (2006.01) | |
| *C12N 15/86* | (2006.01) | |
| *C12N 15/90* | (2006.01) | |

(52) U.S. Cl.
CPC ........ *A61K 35/761* (2013.01); *A61K 48/0016* (2013.01); *A61K 48/005* (2013.01); *A61K 48/0058* (2013.01); *C07K 14/075* (2013.01); *C07K 14/805* (2013.01); *C12N 15/62* (2013.01); *C12N 15/86* (2013.01); *C12N 15/907* (2013.01); *A01K 2207/12* (2013.01); *A01K 2227/105* (2013.01); *A01K 2267/0381* (2013.01)

(58) Field of Classification Search
None
See application file for complete search history.

(56) References Cited

U.S. PATENT DOCUMENTS

| | | | |
|---|---|---|---|
| 5,563,254 A * | 10/1996 | Hoffman | C07K 14/805 |
| | | | 536/23.5 |
| 6,312,957 B1 | 11/2001 | Wilhelm et al. | |
| 8,628,966 B2 * | 1/2014 | Chatterjee | A61K 48/00 |
| | | | 530/350 |
| 9,890,396 B2 | 2/2018 | Chatterjee et al. | |
| 2014/0038239 A1 * | 2/2014 | Perez-Michaut | C12P 19/34 |
| | | | 435/91.53 |
| 2014/0341852 A1 * | 11/2014 | Srivastava | A61P 1/04 |
| | | | 435/456 |
| 2018/0135074 A1 * | 5/2018 | Srivastava | C12N 15/86 |

FOREIGN PATENT DOCUMENTS

| | | | | |
|---|---|---|---|---|
| CA | 2960209 A1 | 3/2016 | | |
| CN | 101 348 786 A | 1/2009 | | |
| WO | WO-9309239 A1 * | 5/1993 | | C07K 14/805 |
| WO | 2009013622 A2 | 1/2009 | | |
| WO | WO-2015148863 A2 * | 10/2015 | | A61K 48/005 |
| WO | WO-2016049230 A1 * | 3/2016 | | A61K 48/0008 |
| WO | WO-2016134338 A1 * | 8/2016 | | A61K 35/76 |
| WO | WO-2017143042 A2 * | 8/2017 | | A61K 48/005 |

OTHER PUBLICATIONS

NCBI accession No. L26475.1, pp. 1-3 (Year: 1994).*
Linden et al PNAS, 93, 11288-11294, (Year: 1996).*
Khan et al Nat Protoc.; 6(4): 482-501 (Year: 2011).*
Hirata et al Journal of Virology, 4612-4620 (Year: 2000).*
Zhang et al Genome Biology 18:35, 1-18 (Year: 2017).*
Chatterjee et al. (1993) "Adeno-associated viral vectors for the delivery of antisense RNA," Methods. 5:51-59.
Einerhand et al. (1995) "Regulated high-level human β-globin gene expression in erythroid cells following recombinant adeno-associated virus-mediated gene transfer," Gene Therapy. 2(5):336-343.
Giraud et al. (1994) "Recombinant junctions formed by site-specific integration of adeno-associated virus into an episome," Proc Natl Acad Sci USA 91(21)10039-43.
Hacein-Bey-Abina (2008) "Insertional oncogenesis in 4 patients after retrovirus-mediated gene therapy of SCID-X1.," J Clin Invest. 118(9):3132-42.
Khan et al. (2011) "AAV-mediated gene targeting methods for human cells," Nature Protocols. 6(4):482-501.
Linden et al. (1996) "Site-specific integration by adeno-associated virus," Proc Natl Acad Sci USA. 93(21):11288-94.
Linden et al. (1996) "The recombination signals for adeno-associated virus site-specific integration," Proc Natl Acad Sci USA. 93(15)7966-72.

(Continued)

*Primary Examiner* — Anoop K Singh
(74) *Attorney, Agent, or Firm* — MINTZ, LEVIN, COHN, FERRIS, GLOVSKY AND POPEO, P.C.

(57) ABSTRACT

Provided herein are adeno-associated virus (AAV) compositions for correcting a mutation in a beta globin gene (HBB) gene and methods of using the same to correct an HBB gene mutation in a cell. Also provided are packaging systems for making the adeno-associated virus compositions.

3 Claims, 15 Drawing Sheets

Specification includes a Sequence Listing.

(56) References Cited

OTHER PUBLICATIONS

Mroske et al. (2012) "A capillary electrophoresis sequencing method for the identification of mutations in the inverted terminal repeats of adeno-associated virus," Hum Gene Ther Methods. 23(2):128-36.

Ponnazhagan et al. (1997) "Adeno-Associated Virus Type 2-Mediated Transduction of Murine Hematopoietic Cells with Long-Term Repopulating Ability and Sustained Expression of a Human Globin Gene In Vivo," J. Virol. 71(4):3098-3104.

Regan et al. (2015) "A rapid molecular approach for chromosomal phasing," PLoS One. 10(3):e0118270.

Sibley et al. (2016) "Lessons from non-canonical splicing," Nat. Rev. Genet. 17(7):407-421.

NCBI Reference Sequence: NC_000019.10 (Mar. 26, 2018) "*Homo sapiens* chromosome 19, GRCh38.p12 Primary Assembly," online at: https://www.ncbi.nlm.nih.gov/nuccore/NC_000019.10/.

NCBI Reference Sequence: NM_000518.4 (May 1, 2018) "*Homo sapiens* hemoglobin subunit beta (HBB), mRNA," online at: https://www.ncbi.nlm.nih.gov/nuccore/nm_000518.4.

NCBI Reference Sequence: NG_000007.3 (Feb. 17, 2019) "*Homo sapiens* beta globin region (HBB@); and beta globin locus transcript 3 (BGLT3); and hemoglobin subunit delta (HBD); and hemoglobin subunit epsilon 1 (HBE1); and hemoglobin subunit gamma 1 (HBG1); and hemoglobin subunit gamma 2 (HBG2), RefSeqGene on chromosome 11," online at: https://www.ncbi.nlm.nih.gov/nuccore/ng_000007.3.

Ohi et al. (1996) "Synthesis of human globin polypeptides mediated by recombinant adeno-associated virus vectors," J Pharm Sci. 85(3):274-281.

International Search Report with Written Opinion from PCT/US2018/056271 dated Jan. 2, 2019.

GenBank U01317.1 [online], Human beta globin region on chromosome 11, Oct. 16, 2008, uploaded, Internet, [retrieved on May 24, 2023], <URL: https://www.ncbi.nlm.nih.gov/nucleotide/U01317.1>.

\* cited by examiner

Lanes:
1. Negative Control
2. 16265 SCD LCLs untransduced
3. 16265 SCD LCLs transduced with AAVHSC17-hHBB-hL-014 vector
4. 16266 SCD LCLs untransduced
5. 16266 SCD LCLs transduced with AAVHSC17-hHBB-hL-014 vector
6. 16267 SCD LCLs untransduced
7. 16267 SCD LCLs transduced with AAVHSC17-hHBB-hL-014 vector

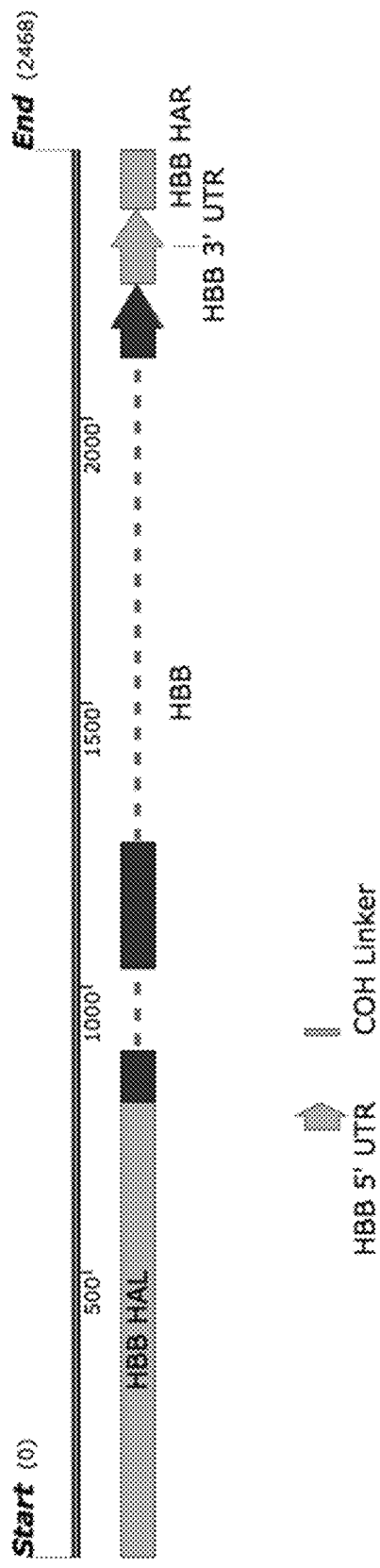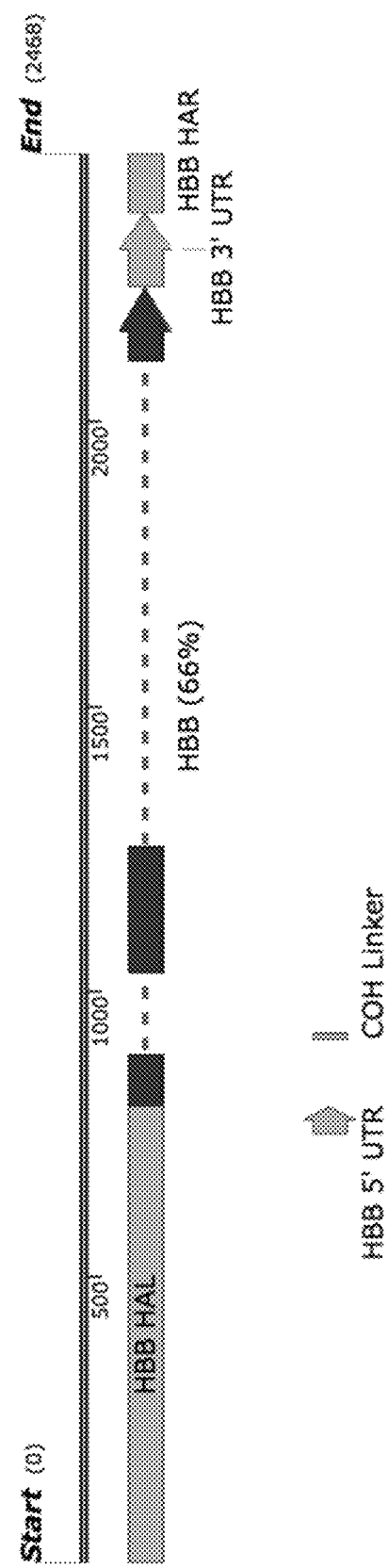
Figure 4C
Figure 4D

Lanes (two lanes for each type of sample):
1. hHBB-hL-011
2. hHBB-hL-001
3. hHBB-hL-014

Lanes:
1. hHBB-hL-011
2. hHBB-hLW-012

Lanes:
1. negative control
2. untranduced cells
3. RKO cells transduced with hHBB-h1W-002
4. RKO cells transduced with hHBB-h1-010
5. LCL cells transduced with hHBB-h1-010

ADENO-ASSOCIATED VIRUS COMPOSITIONS FOR RESTORING HBB GENE FUNCTION AND METHODS OF USE THEREOF

CROSS-REFERENCE TO RELATED APPLICATIONS

This application claims the benefit of U.S. Provisional Application Nos.: 62/574,163, filed Oct. 18, 2017; and 62/621,102, filed Jan. 24, 2018, each of which is hereby incorporated by reference in its entirety.

STATEMENT OF GOVERNMENT INTEREST

This invention was made with government support under Grant No. P30CA033572 awarded by the National Institutes of Health. The Government has certain rights in the invention.

SEQUENCE LISTING

The instant application contains a Sequence Listing which has been submitted electronically in ASCII format, created on Oct. 12, 2018, named 606273_HMT-023_Sequence-_Listing, and is 200,630 bytes in size. The Sequence Listing is hereby incorporated by reference in its entirety.

BACKGROUND

Hemoglobinopathies comprise a family of genetic disorders in which the production, structure, and/or function of a hemoglobin protein is abnormal. Hemoglobin protein makes up approximately 97% of the dry weight of erythrocytes and it increases the oxygen carrying ability of blood by about seventy-fold. The predominant adult hemoglobin protein is composed of two alpha globin (HBA) subunits, two beta globin (HBB) subunits, and a heme group associated with each subunit. Genetic defects in HBB on chromosome 11 can cause certain hemoglobinopathies such as sickle cell disease (SCD) and beta thalassemia.

Sickle cell disease, also called sickle cell anemia, is an autosomal recessive disease affecting approximately 100,000 Americans. It is prevalent among African Americans but also present in other ethnic groups. In West and Central Africa, 1-2% of all babies are born with SCD. SCD is caused by homozygous mutation at nucleotide 20 in the coding sequence of HBB. This mutation replaces the negatively charged amino acid glutamate (encoded by GAG) with a neutral, hydrophobic residue, valine (encoded by GUG) at the sixth amino acid of mature beta globin. Hemoglobin containing a beta globin chain having the SCD mutation tends to aggregate into multi-stranded polymers which distort the shape of erythrocytes, making these cells fragile and shaped like crescents or sickles. These abnormal erythrocytes are more disposed towards hemolysis and deliver less oxygen to tissues and organs. Moreover, hemoglobin aggregation renders erythrocytes rigid and easily retained in small blood vessels, thereby decreasing the blood flow and causing vascular occlusion. As a result, SCD patients suffer from anemia and episodes of pain called "crisis", and organ damage during the crisis is the major cause of the mortality and morbidity associated with SCD. In particular, infarction (i.e., necrosis of tissue due to insufficient blood supply) of bone, spleen, kidney, and lungs is particularly common. By contrast, people who are heterozygous for the sickle cell mutation are largely asymptomatic.

Beta thalassemia affects about 1 out of 100,000 individuals throughout the world and about 1 out of 10,000 people in the European Union. Beta thalassemia is a group of disorders caused by various mutations in HBB that reduce expression of beta globin. So far, 884 different mutations, including substitution, insertions and deletions, have been identified in beta thalassemia (HbVar database). These mutations are located throughout the genomic locus of HBB. Among the substitutions, insertions, and small deletions, pathogenic variants have been found upstream of the 5' UTR and into the 3' UTR. Besides these known 884 mutations, additional variants may be pathogenic only in conjunction with specific variation in the HBB sequence. The beta thalassemia mutations may affect gene transcription, RNA processing, post-transcriptional modification, translation of mRNA, etc. Beta thalassemia is highly variable in severity, with some HBB mutations leading to complete loss of beta globin production and other HBB mutations leading to only a reduction in the quantity of beta globin. Patients with severe beta thalassemia (i.e., thalassemia major), who often have HBB mutation(s) in both alleles, suffer anemia, growth retardation and abnormal organ development. Patients with mild to moderate beta thalassemia (i.e., thalassemia minor or thalassemia intermedia) manifest less severe symptoms.

Hemoglobinopathy can be managed by blood transfusion and supportive care, with SCD and beta thalassemia major requiring chronic transfusions. However, repeated transfusions result in iron overload and require iron chelation therapy to reduce the incidence of complications. Morbidity and mortality of SCD and beta thalassemia can also be attenuated by hydroxyurea, the only FDA approved drug to date for SCD. However, this treatment is not widely used due to its low prescription rate and poor compliance.

In order to cure SCD or beta thalassemia, patients need to receive hematopoietic stem cells carrying at least one copy of functional beta hemoglobin that can be adequately expressed. One approach is to obtain wild-type hematopoietic stem cells from an allogeneic donor through bone marrow transplantation. However, the availability of matched donors is a major limiting factor, and bone marrow transplantation is often associated with serious complications that lead to a mortality rate of 5-10%. More recently, gene therapy approaches have been employed to introduce a beta globin expressing polynucleotide ex vivo into mutant hematopoietic stem cells isolated from the patient.

To date, all HBB gene therapy clinical trials have involved the use of retroviral vectors, such as lentiviral vectors. However, retrovirus-based gene therapy raises a number of safety and efficacy concerns. For example, because insertion of retroviral vectors into the human genome is non-targeted, there is a risk of the vector disrupting a tumor suppressor gene or activating an oncogene, thereby causing a malignancy. Indeed, in a clinical trial for treating X-linked severe combined immunodeficiency (SCID) by transducing CD34+ bone marrow precursors with a gammaretroviral vector, four out of ten patients developed leukemia (Hacein-Bey-Abina et al., J Clin Invest. (2008) 118(9):3132-42). Moreover, due to these safety concerns, lentiviral gene therapy can only be performed ex vivo. This ex vivo use reduces the efficacy of the therapy because the number of hematopoietic stem cells that can be extracted from a subject for ex vivo therapy is only a small fraction of those present in the subject, and there is no reliable method currently in clinical use to expand hematopoietic stem cells ex vivo.

It has also been speculated that nuclease-based gene editing technologies, such as meganucleases, zinc finger nucleases (ZFNs), transcription activator-like effector nucleases (TALENs), and clustered, regularly interspaced, short palindromic repeat (CRISPR) technology, may be used to correct defect in the HBB gene in SCD and beta thalassemia patients. However, each of these technologies raises safety concerns due to the potential for off-target mutation of sites in the human genome similar in sequence to the intended target site.

Accordingly, there is a need in the art for improved gene therapy compositions and methods that can efficiently and safely restore HBB gene function in SCD and beta thalassemia patients.

SUMMARY

Provided herein are adeno-associated virus (AAV) compositions for correcting a mutation in an HBB gene and methods of using the same to correct an HBB gene mutation in a cell. Also provided are packaging systems for making the adeno-associated virus compositions.

The AAV compositions and methods disclosed herein are particularly advantageous in that they allow for highly efficient correction of mutations in an HBB gene in vivo, without the need for cleavage of genomic DNA using an exogenous nuclease (e.g., a meganuclease, a zinc finger nuclease, a transcriptional activator-like nuclease (TALEN), or an RNA-guided nuclease such as a Cas9).

Accordingly, in one aspect, the instant disclosure provides a replication-defective adeno-associated virus (AAV) comprising (a) an AAV capsid comprising an AAV Clade F capsid protein, and (b) a correction genome comprising (i) an editing element for editing a target locus in a target gene, (ii) a 5' homology arm nucleotide sequence 5' of the editing element having homology to a first genomic region 5' to the target locus, and (iii) a 3' homology arm nucleotide sequence 3' of the editing element having homology to a second genomic region 3' to the target locus.

In another aspect, the instant disclosure provides a method for correcting a mutation in a beta globin (HBB) gene in a cell, the method comprising transducing the cell with a replication-defective adeno-associated virus (AAV) comprising (a) an AAV capsid comprising an AAV Clade F capsid protein, and (b) a correction genome comprising: (i) an editing element for editing a target locus in a target gene; (ii) a 5' homology arm nucleotide sequence 5' of the editing element having homology to a first genomic region 5' to the target locus; and (iii) a 3' homology arm nucleotide sequence 3' of the editing element having homology to a second genomic region 3' to the target locus, wherein the cell is transduced without co-transducing or co-administering an exogenous nuclease or a nucleotide sequence that encodes an exogenous nuclease.

In certain embodiments, the cell is a pluripotent stem cell. In certain embodiments, the cell is a hematopoietic stem cell. In certain embodiments, the cell is a CD34+ hematopoietic stem cell. In certain embodiments, the cell is in a mammalian subject and the AAV is administered to the subject in an amount effective to transduce the cell in the subject.

In another aspect, the instant disclosure provides a method for treating a subject having a disease or disorder associated with an HBB gene mutation, the method comprising (a) transducing an erythrocyte progenitor cell from the subject ex vivo with a replication-defective AAV comprising an AAV capsid comprising an AAV Clade F capsid protein; and a correction genome comprising: (i) an editing element for editing a target locus in a target gene; (ii) a 5' homology arm nucleotide sequence 5' of the editing element having homology to a first genomic region 5' to the target locus; and (iii) a 3' homology arm nucleotide sequence 3' of the editing element having homology to a second genomic region 3' to the target locus; and (b) administering the transduced cell to the subject, wherein the cell is transduced without co-transducing or co-administering an exogenous nuclease or a nucleotide sequence that encodes an exogenous nuclease.

In certain embodiments, the erythrocyte progenitor cell is a pluripotent stem cell. In certain embodiments, the erythrocyte progenitor cell is a hematopoietic stem cell. In certain embodiments, the erythrocyte progenitor cell is CD34+ hematopoietic stem cell.

In another aspect, the instant disclosure provides a method for treating a subject having a disease or disorder associated with an HBB gene mutation, the method comprising administering to the subject an effective amount of a replication-defective AAV comprising: (a) an AAV capsid comprising an AAV Clade F capsid protein, and (b) a correction genome comprising (i) an editing element for editing a target locus in a target gene; (ii) a 5' homology arm nucleotide sequence 5' of the editing element having homology to a first genomic region 5' to the target locus; and (iii) a 3' homology arm nucleotide sequence 3' of the editing element having homology to a second genomic region 3' to the target locus, wherein the cell is transduced without co-transducing or co-administering an exogenous nuclease or a nucleotide sequence that encodes an exogenous nuclease.

In certain embodiments, the disease or disorder is thalassemia or sickle cell disease. In certain embodiments, the subject is a human subject.

The following embodiments apply to each of the foregoing aspects.

In certain embodiments, the target gene is the HBB gene. In certain embodiments, the target locus is at a nucleotide point mutation or deletion in the HBB gene. In certain embodiments, the nucleotide point mutation or deletion in the HBB gene is selected from the group consisting of G at position −87, G at position −31, A at position −30, G at position −29, G at position −28, T at position −10, C at position 1, A at position 1, G at position 2, deletion of C and T at positions 17 and 18, A at position 19, deletion of A at position 20, T at position 20, deletion of A and A at positions 25 and 26, addition of G after position 26, A at position 47, A at position 48, deletion of C at position 51, A at position 52, G at position 58, G at position 59, A at position 79, T at position 82, addition of C after position 84, T at position 93, A at position 93, C at position 97, C at position 98, G at position 202, G at position 208, C at position 222, deletion of T at position 241 or 242, deletion of T and T and C and T at positions 254 to 257, T at position 260, deletion of C at position 264 or 265, addition of A after position 343, deletion of G and T at positions 399 and 400, T at position 401, addition of A after position 417, A at position 446, T at position 1099, A at position 1293, T at position 1344. In certain embodiments, the editing element comprises a portion of the wild-type HBB gene that corresponds to the mutation.

In certain embodiments, the editing element comprises the coding regions of one or more exons of an HBB gene. In certain embodiments, the editing element consists of the coding regions of one or more exons of an HBB gene.

In certain embodiments, the editing element comprises a portion of an HBB gene comprising the coding region of exon 1, the entire intron 1, the entire exon 2, the entire intron 2, and the coding region of exon 3. In certain embodiments, the coding regions have been silently altered to be less than 100%, 95%, 90%, 85%, 80%, 75%, 70%, 65%, 60%, 55%, or 50% identical to the corresponding exons of the wild-type HBB gene. In certain embodiments, the editing element comprises at least one of the nucleotide sequences selected from the group consisting of SEQ ID NOs: 43-46 and 105-107.

In certain embodiments, the target locus is AAVS1.

In certain embodiments, the editing element comprises a coding sequence of the HBB gene or a portion thereof. In certain embodiments, the editing element comprises a nucleotide sequence encoding SEQ ID NO: 48. In certain embodiments, the nucleotide sequence encoding SEQ ID NO: 48 consists of nucleotides 4 to 444 of SEQ ID NO: 27. In certain embodiments, the nucleotide sequence encoding SEQ ID NO: 48 is silently altered to be less than 70%, 75%, 80%, 85%, or 90% identical to nucleotides 4 to 444 of SEQ ID NO: 27. In certain embodiments, the nucleotide sequence encoding SEQ ID NO: 48 consists of the sequence of SEQ ID NO: 47 or 100. In certain embodiments, the editing element comprises a stuffer-inserted coding sequence of the HBB gene.

In certain embodiments, the target locus is the internucleotide bond between nucleotide 3 and nucleotide 4 of the target gene, whereby integration of the editing element at the target locus results in the target locus comprising an HBB coding sequence or stuffer-inserted coding sequence starting with the start codon of the target gene. In certain embodiments, the editing element comprises an HBB coding sequence or stuffer-inserted coding sequence consisting of 5' to 3' a start codon and the nucleotide sequence encoding SEQ ID NO: 48, or a portion of the HBB coding sequence or stuffer-inserted coding sequence. In certain embodiments, the target locus is in an intron of the target gene, and wherein the editing element comprises 5' to 3' a splice acceptor site, a ribosomal skipping element, and an HBB coding sequence or stuffer-inserted coding sequence. In certain embodiments, the target locus is in intron 1 of the HBB gene. In certain embodiments, the target locus is adjacently 3' to a coding nucleotide of the target gene, and wherein the editing element comprises 5' to 3' a ribosomal skipping element and an HBB coding sequence or stuffer-inserted coding sequence. In certain embodiments, the target locus is the stop codon of a wild-type target gene (e.g., HBB gene) or the corresponding nucleotides of a mutant target gene (e.g., HBB gene). In certain embodiments, the target locus is the internucleotide bond adjacently 5' to the stop codon of a wild-type target gene (e.g., HBB gene) or the corresponding internucleotide bond of a mutant target gene (e.g., HBB gene).

In certain embodiments, the 5' homology arm nucleotide sequence is at least 90%, 95%, 96%, 97%, 98%, or 99% identical to the first genomic region. In certain embodiments, the 3' homology arm nucleotide sequence is at least 90%, 95%, 96%, 97%, 98%, or 99% identical to the second genomic region. In certain embodiments, the first genomic region is located in a first editing window, and the second genomic region is located in a second editing window. In certain embodiments, the first and second editing windows are different. In certain embodiments, the first and second editing windows are the same. In certain embodiments, the first editing window consists of the nucleotide sequence set forth in SEQ ID NO: 101, 102, or 103. In certain embodiments, the second editing window consists of the nucleotide sequence set forth in SEQ ID NO: 101, 102, or 103. In certain embodiments, the first genomic region consists of the nucleotide sequence set forth in SEQ ID NO: 101. In certain embodiments, the second genomic region consists of the nucleotide sequence set forth in SEQ ID NO: 102. In certain embodiments, the 5' homology arm consists of the nucleotide sequence set forth in SEQ ID NO: 101. In certain embodiments, the 3' homology arm consists of the nucleotide sequence set forth in SEQ ID NO: 102.

In certain embodiments, the editing element further comprises an exogenous polyadenylation sequence 3' to the nucleotide sequence encoding SEQ ID NO: 48. In certain embodiments, the editing element further comprises a restriction endonuclease site not present in the target gene. In certain embodiments, the editing element comprises the nucleotide sequence set forth in any one of SEQ ID NOs: 23-28.

In certain embodiments, each of the 5' and 3' homology arm nucleotide sequences independently has a length of about 100 to about 2000 nucleotides.

In certain embodiments, the correction genome further comprises a 5' inverted terminal repeat (5' ITR) nucleotide sequence 5' of the 5' homology arm nucleotide sequence, and a 3' inverted terminal repeat (3' ITR) nucleotide sequence 3' of the 3' homology arm nucleotide sequence. In certain embodiments, the 5' ITR nucleotide sequence has at least 95% sequence identity to SEQ ID NO:18, and the 3' ITR nucleotide sequence has at least 95% sequence identity to SEQ ID NO:19. In certain embodiments, the 5' ITR nucleotide sequence has at least 95% sequence identity to SEQ ID NO:20, and the 3' ITR nucleotide sequence has at least 95% sequence identity to SEQ ID NO:21. In certain embodiments, the correction genome comprises the nucleotide sequence set forth in any one of SEQ ID NOs: 29-42 and 104.

In certain embodiments, the AAV Clade F capsid protein comprises an amino acid sequence having at least 95% sequence identity with the amino acid sequence of amino acids 203-736 of SEQ ID NO:2, optionally wherein: the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G.

In certain embodiments, (a) the amino acid in the capsid protein corresponding to amino acid 626 of SEQ ID NO: 2 is G, and the amino acid in the capsid protein corresponding to amino acid 718 of SEQ ID NO: 2 is G; (b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M; (c) the amino acid in the capsid protein corresponding to amino acid 505 of SEQ ID NO: 2 is R, and the amino acid in the capsid protein corresponding to amino acid 687 of SEQ ID NO: 2 is R; (d) the amino acid in the capsid protein corresponding to amino acid 346 of SEQ ID NO: 2 is A, and the amino acid in the capsid protein corresponding to amino acid 505 of SEQ ID NO: 2 is R; or (e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 203-736 of SEQ ID NO: 2, 3, 4, 6, 7, 10, 11, 12, 13, 15, 16, or 17.

In certain embodiments, the AAV Clade F capsid protein comprises an amino acid sequence having at least 95% sequence identity with the amino acid sequence of amino acids 138-736 of SEQ ID NO:2, optionally wherein: the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G.

In certain embodiments, (a) the amino acid in the capsid protein corresponding to amino acid 626 of SEQ ID NO: 2 is G, and the amino acid in the capsid protein corresponding to amino acid 718 of SEQ ID NO: 2 is G; (b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M; (c) the amino acid in the capsid protein corresponding to amino acid 505 of SEQ ID NO: 2 is R, and the amino acid in the capsid protein corresponding to amino acid 687 of SEQ ID NO: 2 is R; (d) the amino acid in the capsid protein corresponding to amino acid 346 of SEQ ID NO: 2 is A, and the amino acid in the capsid protein corresponding to amino acid 505 of SEQ ID NO: 2 is R; or (e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 138-736 of SEQ ID NO: 2, 3, 4, 5, 6, 7, 9, 10, 11, 12, 13, 15, 16, or 17.

In certain embodiments, the AAV Clade F capsid protein comprises an amino acid sequence having at least 95% sequence identity with the amino acid sequence of amino acids 1-736 of SEQ ID NO:2, optionally wherein: the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G.

In certain embodiments, (a) the amino acid in the capsid protein corresponding to amino acid 2 of SEQ ID NO: 2 is T, and the amino acid in the capsid protein corresponding to amino acid 312 of SEQ ID NO: 2 is Q; (b) the amino acid in the capsid protein corresponding to amino acid 65 of SEQ ID NO: 2 is I, and the amino acid in the capsid protein corresponding to amino acid 626 of SEQ ID NO: 2 is Y; (c) the amino acid in the capsid protein corresponding to amino acid 77 of SEQ ID NO: 2 is R, and the amino acid in the capsid protein corresponding to amino acid 690 of SEQ ID NO: 2 is K; (d) the amino acid in the capsid protein corresponding to amino acid 119 of SEQ ID NO: 2 is L, and the amino acid in the capsid protein corresponding to amino acid 468 of SEQ ID NO: 2 is S; (e) the amino acid in the capsid protein corresponding to amino acid 626 of SEQ ID NO: 2 is G, and the amino acid in the capsid protein corresponding to amino acid 718 of SEQ ID NO: 2 is G; (f) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M; (g) the amino acid in the capsid protein corresponding to amino acid 505 of SEQ ID NO: 2 is R, and the amino acid in the capsid protein corresponding to amino acid 687 of SEQ ID NO: 2 is R; (h) the amino acid in the capsid protein corresponding to amino acid 346 of SEQ ID NO: 2 is A, and the amino acid in the capsid protein corresponding to amino acid 505 of SEQ ID NO: 2 is R; or (i) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 1-736 of SEQ ID NO: 2, 3, 4, 5, 6, 7, 8, 9, 10, 11, 12, 13, 15, 16, or 17.

In certain embodiments, the integration efficiency of the editing element into the target locus is at least 1% when the AAV is contacted in vitro in the absence of an exogenous nuclease with a population of CD34+ human stem cells under standard AAV transduction conditions. In certain embodiments, the allelic frequency of integration of the editing element into the target locus is at least 0.5% when the AAV is contacted in vitro in the absence of an exogenous nuclease with a population of CD34+ human stem cells under standard AAV transduction conditions.

In another aspect, the instant disclosure provides a pharmaceutical composition comprising an AAV as disclosed herein.

In another aspect, the instant disclosure provides a packaging system for recombinant preparation of an AAV, wherein the packaging system comprises (a) a Rep nucleotide sequence encoding one or more AAV Rep proteins, (b) a Cap nucleotide sequence encoding one or more AAV Clade F capsid proteins as described herein, and (c) a correction genome as disclosed herein, wherein the packaging system is operative in a cell for enclosing the correction genome in the capsid to form the AAV.

In certain embodiments, the packaging system comprises a first vector comprising the Rep nucleotide sequence and the Cap nucleotide sequence, and a second vector comprising the correction genome. In certain embodiments, the Rep nucleotide sequence encodes an AAV2 Rep protein. In certain embodiments, the AAV2 Rep protein is 78/68 or Rep 68/52. In certain embodiments, the AAV2 Rep protein comprises an amino acid sequence having a minimum percent sequence identity to the AAV2 Rep amino acid sequence of SEQ ID NO:22, wherein the minimum percent sequence identity is at least 70% across the length of the amino acid sequence encoding the AAV2 Rep protein.

In certain embodiments, the packaging system further comprises a third vector, wherein the third vector is a helper virus vector. In certain embodiments, the helper virus vector is an independent third vector. In certain embodiments, the helper virus vector is integral with the first vector. In certain embodiments, the helper virus vector is integral with the second vector. In certain embodiments, the third vector comprises genes encoding helper virus proteins.

In certain embodiments, the helper virus is selected from the group consisting of adenovirus, herpes virus, vaccinia virus, and cytomegalovirus (CMV). In certain embodiments, the helper virus is adenovirus. In certain embodiments, the adenovirus genome comprises one or more adenovirus RNA genes selected from the group consisting of E1, E2, E4 and VA. In certain embodiments, the helper virus is herpes simplex virus (HSV). In certain embodiments, the HSV genome comprises one or more of HSV genes selected from the group consisting of UL5/8/52, ICP0, ICP4, ICP22 and UL30/UL42.

In certain embodiments, the first vector and the third vector are contained within a first transfecting plasmid. In certain embodiments, the nucleotides of the second vector and the third vector are contained within a second transfecting plasmid. In certain embodiments, the nucleotides of the first vector and the third vector are cloned into a recombinant helper virus. In certain embodiments, the nucleotides of the second vector and the third vector are cloned into a recombinant helper virus.

In another aspect, the instant disclosure provides a method for recombinant preparation of an AAV, the method comprising introducing a packaging system as described herein into a cell under conditions operative for enclosing the correction genome in the capsid to form the AAV.

BRIEF DESCRIPTION OF THE DRAWINGS

FIGS. 4A, 4B, 4C, and 4D are vector maps showing the genetic elements between the two AAV ITRs of HBB correction vectors hHBB-hL-001, hHBB-hLW-013, hHBB-hL-011, and hHBB-hLW-012, respectively. In these figures, the black regions of HBB denote nucleotide sequences in the exons encoding a human HBB protein, and the dashed lines between the black regions denote introns between the exons.

In FIGS. 7A-D, the black regions labeled as "HBB coding region" or "HBB coding region (66%)" denote nucleotide sequences encoding a human HBB protein, either from the start codon to the stop codon (FIGS. 7C and 7D), or from the second codon to the stop codon (FIGS. 7 and 7B).

DETAILED DESCRIPTION

Figure 1A:
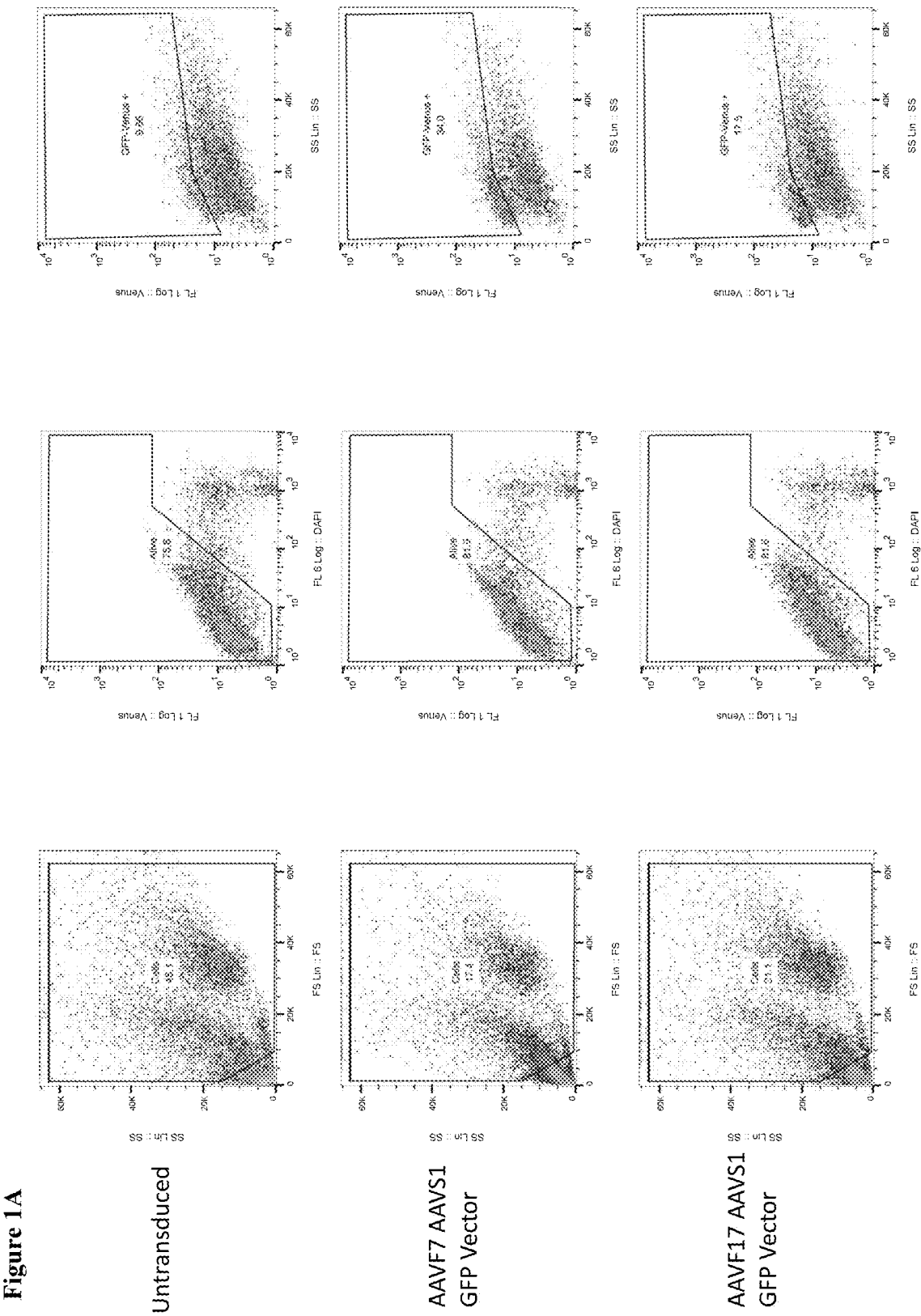
FIGS. 1A and 1B are graphs showing flow cytometry results of integration of AAVS1-FP into the genome of the GM16265 cells, wherein the AAVS1-FP vector was packaged in AAVHSC7, AAVHSC15, and AAVHSC17.

The instant disclosure provides adeno-associated virus (AAV) compositions for correcting a mutation in an HBB gene and methods of using the same to correct an HBB gene mutation in a cell. Also provided are packaging systems for making the adeno-associated virus compositions.

I. DEFINITIONS

As used herein, the term "replication-defective adeno-associated virus" refers to an AAV comprising a genome lacking Rep and Cap genes.

As used herein, the term "HBB gene" refers to a wild-type or mutant human beta globin gene, including but not limited to the coding regions, exons, introns, 5' UTR, 3' UTR, and transcriptional regulatory regions of the HBB gene.

As used herein, the term "correcting a mutation in an HBB gene" refers to the insertion, deletion, or substitution of one or more nucleotides at a target locus in a target gene (e.g., a mutant HBB gene) to create a locus that is capable of expressing a wild-type HBB protein or a functional equivalent thereof. In certain embodiments, "correcting a mutation in an HBB gene" involves reverting a mutation in an HBB gene back to the wild-type sequence. In certain embodiments, "correcting a mutation in an HBB gene" involves inserting a nucleotide sequence encoding at least a portion of a wild-type beta globin protein or a functional equivalent thereof into the target gene (e.g., the mutant HBB gene), such that a wild-type beta globin protein or a functional equivalent thereof is expressed from the locus of the target gene (e.g., the mutant HBB gene locus), optionally under the control of an endogenous target gene promoter (e.g., HBB gene promoter). As used herein, a "functional equivalent" refers to a product of a gene or fragment thereof that can function as a wild-type beta globin. In certain embodiments, a functional equivalent of HBB can include other globin genes or pseudogenes, such as epsilon globin (HBE), delta globin (HBD), gamma globin 1 (HBG1), gamma globin 2 (HBG2), and HBB pseudogene HBBP. In certain embodiments, a functional equivalent of HBB can be a modified beta globin protein, wherein the modification confers at least one characteristic not found in wild-type beta globin, e.g., the ability to inhibit aggregation of beta globin carrying an SCD mutation.

As used herein, the term "correction genome" refers to a recombinant AAV genome that is capable of integrating an editing element (e.g., one or more nucleotides or an internucleotide bond) via homologous recombination into a target locus to correct a genetic defect in an HBB gene. In certain embodiments, the target locus is in the human HBB gene. The skilled artisan will appreciate that the portion of a correction genome comprising the 5' homology arm, editing element, and 3' homology arm can be in the sense or antisense orientation relative to the target locus (e.g., the human HBB gene).

As used herein, the term "editing element" refers to the portion of a correction genome that when integrated at a target locus modifies the target locus. An editing element can mediate insertion, deletion or substitution of one or more nucleotides at the target locus.

As used herein, the term "target locus" refers to a region of a chromosome or an internucleotide bond that is modified by an editing element. In certain embodiments, the target locus is a region or an internucleotide bond in the HBB gene, optionally wherein the target locus comprises at least one genetic mutation that compromises the expression or function of beta globin protein. In certain embodiments, the target locus is AAVS1. The AAVS1 locus is on chromosome 19 qter13.3-13.4, nucleotides 55,090,913 to 55,117,600 of NCBI Reference Sequence No. NC_000019.10, as described in Giraud et al., Proc Natl Acad Sci USA. (1994) 91(21): 10039-43; Linden et al., Proc Natl Acad Sci USA. (1996) 93(21):11288-94; and Linden et al., Proc Natl Acad Sci USA. (1996) 93(15):7966-72, each of which is incorporated herein by reference in its entirety. In certain embodiments, the target locus is a safe harbor locus. Safe harbor loci are sites in the genome able to accommodate the integration of new genetic material in a manner that ensures that the newly inserted genetic material: (1) function predictably; and (2) do not cause alterations of the host genome that may pose a risk to the host cell or organism. Accordingly, in certain embodiments, the target locus may be any safe harbor locus known in the art that can support predictable transgene expression while minimizing the risk of unwanted interactions with the host genome.

As used herein, the term "target gene" refers to a gene in which a target locus or a portion thereof is located. In certain embodiments, the target locus is fully in a target gene. In certain embodiments, the target gene is HBB. In certain embodiments, the target gene is human PPP1R12C. In certain embodiments, the target gene is expressed in an erythrocyte progenitor.

As used herein, the term "homology arm" refers to a portion of a correction genome positioned 5' or 3' of an editing element that is substantially identical to the genome flanking a target locus. In certain embodiments, the target locus is in a human HBB gene, and the homology arm comprises a sequence substantially identical to the genome flanking the target locus.

As used herein, the term "Clade F capsid protein" refers to an AAV VP1, VP2, or VP3 capsid protein that comprises an amino acid sequence having at least 90% identity with the VP1, VP2, or VP3 amino acid sequences set forth, respectively, in amino acids 1-736, 138-736, and 203-736 of SEQ ID NO:1 herein. As used herein, the identity between two nucleotide sequences or between two amino acid sequences is determined by the number of identical nucleotides or amino acids in alignment divided by the full length of the longer nucleotide or amino acid sequence.

As used herein, the term "a disease or disorder associated with an HBB gene mutation" refers to any disease or disorder caused by, exacerbated by, or genetically linked with variation of an HBB gene. In certain embodiments, the disease or disorder associated with an HBB gene mutation is a hemoglobinopathy, such as sickle cell disease or beta thalassemia.

As used herein, the term "silently altered" refers to alteration of a coding sequence or a stuffer-inserted coding sequence of a gene (e.g., by nucleotide substitution) without changing the amino acid sequence of the polypeptide encoded by the coding sequence or stuffer-inserted coding sequence. Such silent alteration is advantageous in that it reduces the likelihood of integration of the correction genome into loci of other genes or pseudogenes paralogous to the target gene (e.g., another globin gene locus or a beta globin pseudogene locus). Such silent alteration also reduces the homology between the editing element and the target gene, thereby reducing undesired integration mediated by the editing element rather than by a homology arm.

As used herein, the term "coding sequence" refers to the portion of a complementary DNA (cDNA), or a silently altered sequence thereof, that encodes a polypeptide, starting at a start codon and ending at a stop codon. A gene may have one or more wild-type coding sequences due to alternative splicing and/or alternative translation initiation. An exemplary wild-type HBB coding sequence is set forth in nucleotides 51-494 of the NCBI Reference Sequence: NM_000518.4.

As used herein, the term "coding nucleotide" refers to a nucleotide of a gene that corresponds to a nucleotide in a coding sequence of the gene, except the 3' nucleotide of the stop codon. Accordingly, in certain embodiments, a coding nucleotide of the HBB gene is any one of nucleotides 1-443 of the HBB gene.

As used herein, the term "stuffer-inserted coding sequence" of a gene refers to a nucleotide sequence comprising one or more introns inserted in a coding sequence of the gene. In certain embodiments, at least one of the introns is a nonnative intron, i.e., having a sequence different from a native intron of the gene. In certain embodiments, all of the introns in the stuffer-inserted coding sequence are nonnative introns. A nonnative intron can have the sequence of an intron from a different species or the sequence of an intron in a different gene from the same species. Alternatively or additionally, at least a portion of a nonnative intron sequence can be synthetic. A skilled worker will appreciate that nonnative intron sequences can be designed to mediate RNA splicing by introducing any consensus splicing motifs known in the art. Exemplary consensus splicing motifs are provided in Sibley et al., (2016) Nature Reviews Genetics, 17, 407-21, which is incorporated by reference herein in its entirety. Insertion of a nonnative intron may promote the efficiency and robustness of vector packaging, as stuffer sequences allow adjustments of the vector to reach an optimal size (e.g., 4.5-4.8 kb). In certain embodiments, at least one of the introns is a native intron of the gene. In certain embodiments, all of the introns in the stuffer-inserted coding sequence are native introns of the gene. The nonnative or native introns can be inserted at any internucleotide bonds in the coding sequence. In certain embodiments, one or more nonnative or native introns are inserted at internucleotide bonds predicted to promote efficient splicing (see e.g., Zhang (1998) Human Molecular Genetics, 7(5):919-32, which is incorporated by reference herein in its entirety). In certain embodiments, one or more nonnative or native introns are inserted at internucleotide bonds that link two endogenous exons.

As used herein, the term "ribosomal skipping element" refers to a nucleotide sequence encoding a short peptide sequence capable of causing generation of two peptide chains from translation of one mRNA molecule. As used herein, the term "ribosomal skipping peptide" refers to a peptide encoded by a ribosomal skipping element. In certain embodiments, the ribosomal skipping peptide comprises a consensus motif of $X_1X_2EX_3NPGP$, wherein $X_1$ is D or G, $X_2$ is V or I, and $X_3$ is any amino acid (SEQ ID NO: 49). In certain embodiments, the ribosomal skipping peptide is selected from the group consisting of thosea-asigna virus 2A peptide (T2A), porcine teschovirus-1 2A peptide (P2A), foot-and-mouth disease virus 2A peptide (F2A), equine rhinitis A virus 2A peptide (E2A), cytoplasmic polyhedrosis virus 2A peptide (BmCPV 2A), and flacherie virus of *B. mori* 2A peptide (BmIFV 2A). Exemplary amino acid sequences of T2A peptide and P2A peptide are set forth in SEQ ID NOs: 71 and 73, respectively. Exemplary nucleotide sequences of T2A element and P2A element are set forth in SEQ ID NOs: 72 and 74, respectively. In certain embodiments, the ribosomal skipping element encodes a peptide that further comprises a sequence of Gly-Ser-Gly at the N terminus, optionally wherein the sequence of Gly-Ser-Gly is encoded by the nucleotide sequence of GGCAGCGGA (SEQ ID NO: 75). While not wishing to be bound by theory, it is hypothesized that ribosomal skipping elements function by: terminating translation of the first peptide chain and re-initiating translation of the second peptide chain; or by cleavage of a peptide bond in the ribosomal skipping peptide by an intrinsic protease activity of the encoded peptide or by another protease in the environment (e.g., cytosol).

As used herein, the term "polyadenylation sequence" refers to a DNA sequence that when transcribed into RNA constitutes a polyadenylation signal sequence.

In the instant disclosure, nucleotide positions in a gene are specified relative to the first nucleotide of the start codon. The first nucleotide of a start codon is position 1, nucleotides 5' to the first nucleotide of a start codon have negative numbers, and the nucleotides 3' to the first nucleotide of a start codon have positive numbers. For example, nucleotide 1 of the HBB gene as used herein is nucleotide 70,595 of the NCBI Reference Sequence: NG_000007.3. The nucleotide adjacently 5' to the start codon is nucleotide −1.

In the instant disclosure, exons and introns in a gene are specified relative to the exon encompassing the first nucleotide of the start codon. The exon encompassing the first nucleotide of the start codon is exon 1. Exons 3' to exon 1 are from 5' to 3': exon 2, exon 3, etc. Introns 3' to exon 1 are from 5' to 3': intron 1, intron 2, etc. Accordingly, a gene comprises from 5' to 3': exon 1, intron 1, exon 2, intron 2, exon 3, etc. An exemplary exon 1 of the human HBB gene is nucleotides 70,545 to 70,686 of the NCBI Reference Sequence: NG_000007.3. An exemplary intron 1 of the human HBB gene is nucleotides 70,687 to 70,816 of the NCBI Reference Sequence: NG_000007.3. A skilled artisan will appreciate that a gene may be transcribed into multiple different mRNAs. As such, a gene (e.g., HBB) may have multiple different sets of exons and introns.

As used herein, the term "integration" refers to introduction of an editing element into a target locus by homologous recombination between a correction genome and the target gene. Integration of an editing element can result in substitution, insertion and/or deletion of one or more nucleotides in the target gene.

As used herein, the term "integration efficiency of the editing element into the target locus" refers to the percentage of cells in a transduced population in which integration of the editing element into the target locus has occurred.

As used herein, the term "allelic frequency of integration of the editing element into the target locus" refers to the percentage of alleles in a population of transduced cells in which integration of the editing element into the target locus has occurred.

As used herein, the term "standard AAV transduction conditions" refers to transduction of $2\times10^5$ CD34$^+$ human stem cells with an AAV at a multiplicity of infection (MOI)

of 1.5×10⁵, wherein the cells are cultured in Iscove's Modified Dulbecco's Medium (IMDM) supplemented with 20% Fetal Calf Serum (FCS), 100 µg/mL streptomycin, 100 U/mL penicillin, 2 mmol/L L-glutamine, 10 ng/mL human IL-3, 10 ng/mL human IL-6, and 1 ng/mL human SCF, at 37° C. in an incubator environment of 5% carbon dioxide ($CO_2$), wherein the AAV is formulated in phosphate buffered saline (PBS), and wherein the AAV is added to the cell culture medium containing the CD34⁺ cells in a volume that is less than or equal to ⅛th of the volume of the culture medium.

As used herein, the term "effective amount" in the context of the administration of an AAV to a subject refers to the amount of the AAV that achieves a desired prophylactic or therapeutic effect.

As used herein, the term "an erythrocyte progenitor" refers to a cell capable of differentiating into an erythrocyte. In certain embodiments, the erythrocyte progenitor is a pluripotent stem cell. In certain embodiments, the erythrocyte progenitor is an induced pluripotent stem cell. In certain embodiments, the erythrocyte progenitor is a hematopoietic stem cell. In certain embodiments, the erythrocyte progenitor is a CD34⁺ hematopoietic stem cell. In certain embodiments, the erythrocyte progenitor is a myeloid progenitor cell. In certain embodiments, the erythrocyte progenitor is a megakaryocyte-erythroid progenitor cell. In certain embodiments, the erythrocyte progenitor is an erythroid precursor cell.

II. ADENO-ASSOCIATED VIRUS COMPOSITIONS

In one aspect, the disclosure provides novel replication-defective AAV compositions useful for correcting mutations in an HBB gene. The AAV disclosed herein generally comprise: an AAV capsid comprising an AAV Clade F capsid protein; and a correction genome for editing a target locus in an HBB gene.

Any AAV Clade F capsid protein or derivative thereof can be used in the AAV compositions disclosed herein. For example, in certain embodiments, the AAV Clade F capsid protein comprises an amino acid sequence having at least 80%, 85%, 90%, 95%, or 99% sequence identity with the amino acid sequence of amino acids 203-736 of SEQ ID NO:2. In certain embodiments, the AAV Clade F capsid protein comprises an amino acid sequence having at least 80%, 85%, 90%, 95%, or 99% sequence identity with the amino acid sequence of amino acids 203-736 of SEQ ID NO:2, wherein: the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 203-736 of SEQ ID NO: 2, 3, 4, 6, 7, 10, 11, 12, 13, 15, 16, or 17.

For example, in certain embodiments, the AAV Clade F capsid protein comprises an amino acid sequence having at least 80%, 85%, 90%, 95%, or 99% sequence identity with the amino acid sequence of amino acids 138-736 of SEQ ID NO:2. In certain embodiments, the AAV Clade F capsid protein comprises an amino acid sequence having at least 80%, 85%, 90%, 95%, or 99% sequence identity with the amino acid sequence of amino acids 138-736 of SEQ ID NO:2, wherein: the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 138-736 of SEQ ID NO: 2, 3, 4, 5, 6, 7, 9, 10, 11, 12, 13, 15, 16, or 17.

For example, in certain embodiments, the AAV Clade F capsid protein comprises an amino acid sequence having at least 90%, 95%, or 99% sequence identity with the amino acid sequence of amino acids 1-736 of SEQ ID NO:2. In certain embodiments, the AAV Clade F capsid protein comprises an amino acid sequence having at least 90%, 95%, or 99% sequence identity with the amino acid sequence of amino acids 1-736 of SEQ ID NO:2, wherein: the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 2 of SEQ ID NO: 2 is T, and the amino acid in the capsid protein corresponding to amino acid 312 of SEQ ID NO: 2 is Q. In certain embodiments, the amino acid in the capsid protein corresponding to amino acid 65 of SEQ ID NO: 2 is I, and the amino acid in the capsid protein corresponding to amino acid 626 of SEQ ID NO: 2 is Y. In certain embodiments, the amino acid in the capsid protein corresponding to amino acid 77 of SEQ ID NO: 2 is R, and the amino acid in the capsid protein corresponding to amino acid 690 of SEQ ID NO: 2 is K. In certain embodiments, the amino acid in the capsid protein corresponding to amino acid 119 of SEQ ID NO: 2 is L, and the amino acid in the capsid protein corresponding to amino acid 468 of SEQ ID NO: 2 is S. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 1-736 of SEQ ID NO: 2, 3, 4, 5, 6, 7, 8, 9, 10, 11, 12, 13, 15, 16, or 17.

In certain embodiments, the AAV capsid comprises two or more of: (a) a Clade F capsid protein comprising the amino acid sequence of amino acids 203-736 of SEQ ID NO: 2, 3, 4, 6, 7, 10, 11, 12, 13, 15, 16, or 17; (b) a Clade F capsid protein comprising the amino acid sequence of amino acids 138-736 of SEQ ID NO: 2, 3, 4, 5, 6, 7, 9, 10, 11, 12, 13, 15, 16, or 17; and (c) a Clade F capsid protein comprising the amino acid sequence of amino acids 1-736 of SEQ ID NO: 2, 3, 4, 5, 6, 7, 8, 9, 10, 11, 12, 13, 15, 16, or 17. In certain embodiments, the AAV capsid comprises: (a) a Clade F capsid protein having an amino acid sequence consisting of amino acids 203-736 of SEQ ID NO: 2, 3, 4, 6, 7, 10, 11, 12, 13, 15, 16, or 17; (b) a Clade F capsid protein having an amino acid sequence consisting of amino acids 138-736 of SEQ ID NO: 2, 3, 4, 5, 6, 7, 9, 10, 11, 12, 13, 15, 16, or 17; and (c) a Clade F capsid protein having an amino acid sequence consisting of amino acids 1-736 of SEQ ID NO: 2, 3, 4, 5, 6, 7, 8, 9, 10, 11, 12, 13, 15, 16, or 17.

In certain embodiments, the AAV capsid comprises one or more of: (a) a Clade F capsid protein comprising the amino acid sequence of amino acids 203-736 of SEQ ID NO: 8; (b) a Clade F capsid protein comprising the amino acid sequence of amino acids 138-736 of SEQ ID NO: 8; and (c) a Clade F capsid protein comprising the amino acid sequence of amino acids 1-736 of SEQ ID NO: 8. In certain embodiments, the AAV capsid comprises two or more of: (a) a Clade F capsid protein comprising the amino acid sequence of amino acids 203-736 of SEQ ID NO: 8; (b) a Clade F capsid protein comprising the amino acid sequence of amino acids 138-736 of SEQ ID NO: 8; and (c) a Clade F capsid protein comprising the amino acid sequence of amino acids 1-736 of SEQ ID NO: 8. In certain embodiments, the AAV capsid comprises: (a) a Clade F capsid protein having an amino acid sequence consisting of amino acids 203-736 of SEQ ID NO: 8; (b) a Clade F capsid protein having an amino acid sequence consisting of amino acids 138-736 of SEQ ID NO: 8; and (c) a Clade F capsid protein having an amino acid sequence consisting of amino acids 1-736 of SEQ ID NO: 8.

In certain embodiments, the AAV capsid comprises one or more of: (a) a Clade F capsid protein comprising the amino acid sequence of amino acids 203-736 of SEQ ID NO: 13; (b) a Clade F capsid protein comprising the amino acid sequence of amino acids 138-736 of SEQ ID NO: 13; and (c) a Clade F capsid protein comprising the amino acid sequence of amino acids 1-736 of SEQ ID NO: 13. In certain embodiments, the AAV capsid comprises two or more of: (a) a Clade F capsid protein comprising the amino acid sequence of amino acids 203-736 of SEQ ID NO: 13; (b) a Clade F capsid protein comprising the amino acid sequence of amino acids 138-736 of SEQ ID NO: 13; and (c) a Clade F capsid protein comprising the amino acid sequence of amino acids 1-736 of SEQ ID NO: 13. In certain embodiments, the AAV capsid comprises: (a) a Clade F capsid protein having an amino acid sequence consisting of amino acids 203-736 of SEQ ID NO: 13; (b) a Clade F capsid protein having an amino acid sequence consisting of amino acids 138-736 of SEQ ID NO: 13; and (c) a Clade F capsid protein having an amino acid sequence consisting of amino acids 1-736 of SEQ ID NO: 13.

In certain embodiments, the AAV capsid comprises one or more of: (a) a Clade F capsid protein comprising the amino acid sequence of amino acids 203-736 of SEQ ID NO: 16; (b) a Clade F capsid protein comprising the amino acid sequence of amino acids 138-736 of SEQ ID NO: 16; and (c) a Clade F capsid protein comprising the amino acid sequence of amino acids 1-736 of SEQ ID NO: 16. In certain embodiments, the AAV capsid comprises two or more of: (a) a Clade F capsid protein comprising the amino acid sequence of amino acids 203-736 of SEQ ID NO: 16; (b) a Clade F capsid protein comprising the amino acid sequence of amino acids 138-736 of SEQ ID NO: 16; and (c) a Clade F capsid protein comprising the amino acid sequence of amino acids 1-736 of SEQ ID NO: 16. In certain embodiments, the AAV capsid comprises: (a) a Clade F capsid protein having an amino acid sequence consisting of amino acids 203-736 of SEQ ID NO: 16; (b) a Clade F capsid protein having an amino acid sequence consisting of amino acids 138-736 of SEQ ID NO: 16; and (c) a Clade F capsid protein having an amino acid sequence consisting of amino acids 1-736 of SEQ ID NO: 16.

Correction genomes useful in the AAV compositions disclosed herein generally comprise: (i) an editing element for editing a target locus in a target gene, (ii) a 5' homology arm nucleotide sequence 5' of the editing element having homology to a first genomic region 5' to the target locus, and (iii) a 3' homology arm nucleotide sequence 3' of the editing element having homology to a second genomic region 3' to the target locus. In certain embodiments, the correction genome comprises a 5' inverted terminal repeat (5' ITR) nucleotide sequence 5' of the 5' homology arm nucleotide sequence, and a 3' inverted terminal repeat (3' ITR) nucleotide sequence 3' of the 3' homology arm nucleotide sequence.

Editing elements used in the correction genomes disclosed herein can mediate insertion, deletion, or substitution of one or more nucleotides at the target locus. The target locus can locate fully or partially in a target gene, which can be the HBB gene or another gene expressed in an erythrocyte progenitor.

In certain embodiments, when correctly integrated by homologous recombination at the target locus, the editing element corrects a mutation in an HBB gene back to the wild-type HBB sequence or to a silently altered sequence that encodes the wild-type HBB protein or a functional equivalent thereof. Most mutations in the HBB gene can be corrected by an editing element as disclosed herein. In certain embodiments, the editing element is one or more nucleotides that correct a substitution or deletion mutation in the HBB gene. In certain embodiments, the editing element is an internucleotide bond that deletes an insertion mutation in the HBB gene. In certain embodiments, the editing element comprises one or more coding exons of an HBB gene. For example, the editing element can comprise a portion of an HBB gene that encompasses the coding region of exon 1, the entire intron 1, the entire exon 2, the entire intron 2, and the coding region of exon 3. The exons can be wild-type or silently altered as disclosed herein.

In certain embodiments, the editing element comprises at least a portion of a coding sequence or stuffer-inserted coding sequence of an HBB gene. In certain embodiments, the editing element comprises all or substantially all of a coding sequence or stuffer-inserted coding sequence of an HBB gene. For example, in certain embodiments, the editing element comprises nucleotides 4 to 444 of an HBB coding sequence, or a portion of an HBB stuffer-inserted coding sequence from nucleotide 4 to the stop codon, optionally further comprising an exogenous polyadenylation sequence 3' to the portion of HBB coding sequence or stuffer-inserted coding sequence. In certain embodiments, the editing element comprises a nucleotide sequence encoding SEQ ID NO: 48, and can optionally further comprise an exogenous polyadenylation sequence 3' to the nucleotide sequence encoding SEQ ID NO: 48. In certain embodiments, such editing elements can be integrated into exon 1 immediately after the endogenous start codon of the HBB gene (e.g., between nucleotide 3 and nucleotide 4 of the HBB gene) by homologous recombination, whereby integration of the editing element results in generation of a complete HBB coding sequence in-frame with the start codon of the endogenous HBB gene. In certain embodiments, such editing elements can be integrated into exon 1 immediately after the endogenous start codon of a non-HBB target gene (e.g., between nucleotide 3 and nucleotide 4 of the target gene) by homologous recombination, whereby integration of the editing element results in generation of a complete HBB coding sequence in-frame with the start codon of the endogenous target gene. The portion of HBB coding sequence in the editing element can be wild-type or silently mutated as disclosed herein. The portion of HBB amino acid sequence encoded by the editing element can be wild-type or a functional equivalent thereof.

In certain embodiments, the editing element comprises at least a portion of an HBB coding sequence or stuffer-inserted coding sequence (e.g., a complete HBB coding sequence or stuffer-inserted coding sequence), and a ribosomal skipping element or an exogenous polyadenylation sequence. In certain embodiments, the editing element comprises 5' to 3' a ribosomal skipping element, and at least a portion of an HBB coding sequence or stuffer-inserted coding sequence (e.g., a complete HBB coding sequence or stuffer-inserted coding sequence). In certain embodiments, the editing element comprises 5' to 3': a ribosomal skipping element; a complete HBB coding sequence or stuffer-inserted coding sequence; and an exogenous polyadenylation sequence. In certain embodiments, the aforementioned editing element can be integrated adjacently 3' to a coding nucleotide of a target gene (e.g., adjacently 5' to the stop codon of the native HBB gene) by homologous recombination to produce a recombinant target gene comprising 5' to 3': a 5' portion of the target gene ending at the coding nucleotide, a ribosomal skipping element, a complete HBB coding sequence or stuffer-inserted coding sequence, and an exogenous polyadenylation sequence, wherein the ribosomal skipping element is positioned such that it is in frame with the coding region of the target gene and the complete HBB coding sequence or stuffer-inserted coding sequence. Expression of this recombinant target gene produces a first polypeptide comprising the amino acid sequence encoded by an N-terminal portion of the target gene fused to a first portion of the encoded ribosomal skipping peptide, and a second polypeptide comprising a second portion of the encoded ribosomal skipping peptide (e.g., a single proline residue) fused to the complete HBB amino acid sequence. The HBB coding sequence or the coding regions of the HBB stuffer-inserted coding sequence in the editing element can be wild-type or silently mutated as disclosed herein. The HBB amino acid sequence encoded by the editing element can be wild-type or a functional equivalent thereof (e.g., lacking the first methionine). The target locus can be an internucleotide bond or a nucleotide sequence adjacently 3' to a coding nucleotide of the target gene. In certain embodiments, the target locus consists of the native stop codon of the HBB gene.

In certain embodiments, the editing element comprises at least a portion of an HBB coding sequence or stuffer-inserted coding sequence (e.g., a complete HBB coding sequence or stuffer-inserted coding sequence), and one or more of: a splice acceptor site; a splice donor site; a ribosomal skipping element; and an exogenous polyadenylation sequence. In certain embodiments, the editing element comprises 5' to 3': a splice acceptor site; a ribosomal skipping element; and at least a portion of an HBB coding sequence or stuffer-inserted coding sequence (e.g., a complete HBB coding sequence or stuffer-inserted coding sequence). In certain embodiments, the editing element comprises 5' to 3': a splice acceptor site; a ribosomal skipping element; a complete HBB coding sequence or stuffer-inserted coding sequence; and an exogenous polyadenylation sequence. In certain embodiments, the aforementioned editing element can be integrated into an intron of a target gene (e.g., intron 1 of the endogenous HBB gene) by homologous recombination to produce a recombinant HBB gene comprising 5' to 3': the one or more exons 5' to the intron of the target gene; a 5' portion of the intron including the endogenous splice donor site; a splice acceptor site; a ribosomal skipping element, a complete HBB coding sequence or stuffer-inserted coding sequence; and an exogenous polyadenylation sequence, wherein the ribosomal skipping element is positioned such that it is in frame with the complete HBB coding sequence or stuffer-inserted coding sequence and such that splicing of the splice acceptor site to the endogenous splice donor site of the target gene places it in frame with the coding region of the target gene. Expression of this recombinant target gene produces a first polypeptide comprising the target gene amino acid sequence encoded by the endogenous exon(s) 5' to the insertion site fused to a first portion of the encoded ribosomal skipping peptide, and a second polypeptide comprising a second portion of the encoded ribosomal skipping peptide (e.g., a single proline residue) fused to a complete HBB amino acid sequence. The HBB coding sequence or stuffer-inserted coding sequence in the editing element can be wild-type or silently mutated as disclosed herein. The HBB amino acid sequence encoded by the editing element can be wild-type or a functional equivalent thereof (e.g., lacking the first methionine). The target locus can be an internucleotide bond or a nucleotide sequence adjacently 3' to a nucleotide in an intron of the target gene.

In certain embodiments, one or more portions of an HBB coding sequence or stuffer-inserted coding sequence within an editing element can be silently altered to be non-identical to the corresponding exons of the wild-type HBB gene. Such silent alteration is advantageous in that it reduces the likelihood of integration of the correction genome into loci of other globin genes or pseudogenes, e.g., a beta globin pseudogene locus. Such silent alteration also reduces the homology between the editing element and the target gene, thereby reducing undesired integration mediated by the editing element rather than by a homology arm.

Accordingly, in certain embodiments, the editing element comprises coding regions of one or more exons of an HBB gene that have been silently altered to be less than 100% (e.g., less than 95%, 90%, 85%, 80%, 75%, 70%, 65%, 60%, 55%, or 50%) identical to the corresponding coding regions of exons of the wild-type HBB gene. In certain embodiments, the editing element comprises coding regions of one or more exons of an HBB gene that have been silently altered to be less than 70% identical to the corresponding coding regions of exons of the wild-type HBB gene. In certain embodiments, the editing element comprises coding regions of one or more exons of an HBB gene that have been silently altered to be less than 85% identical to the corresponding coding regions of exons of the wild-type HBB gene.

In certain embodiments, the editing element comprises a portion of an HBB gene encompassing the coding region of exon 1, the entire intron 1, the entire exon 2, the entire intron 2, and the coding region of exon 3, wherein one or more of the coding region of exon 1, the entire exon 2, and the coding region of exon 3 has been silently altered to be less than 100% (e.g., less than 95%, 90%, 85%, 80%, 75%, 70%, 65%, 60%, 55%, or 50%) identical to the corresponding regions of exons of the wild-type HBB gene. In certain embodiments, the editing element comprises a portion of an HBB gene encompassing the coding region of exon 1, the entire intron 1, the entire exon 2, the entire intron 2, and the coding region of exon 3, wherein one or more of the coding region of exon 1, the entire exon 2, and the coding region of exon 3 has been silently altered to be less than 70% identical to the corresponding regions of exons of the wild-type HBB gene.

In certain embodiments, the editing element comprises a portion of an HBB gene encompassing the coding region of exon 1, the entire intron 1, the entire exon 2, the entire intron 2, and the coding region of exon 3, wherein each one of the coding region of exon 1, the entire exon 2, and the coding region of exon 3 has been silently altered to be less than 100% (e.g., less than 95%, 90%, 85%, 80%, 75%, 70%, 65%, 60%, 55%, or 50%) identical to the corresponding regions of exons of the wild-type HBB gene. In certain embodiments, the editing element comprises a portion of an HBB gene encompassing the coding region of exon 1, the entire intron 1, the entire exon 2, the entire intron 2, and the coding region of exon 3, wherein each one of the coding region of exon 1, the entire exon 2, and the coding region of exon 3 has been silently altered to be less than 70% identical to the corresponding regions of exons of the wild-type HBB gene.

In certain embodiments, the editing element comprises one or more of the nucleotide sequences selected from the group consisting of SEQ ID NOs: 43-46 and 105-107. In certain embodiments, the editing element comprises two or more of the nucleotide sequences selected from the group consisting of SEQ ID NOs: 43-46 and 105-107. In certain embodiments, the editing element comprises the nucleotide sequence set forth in SEQ ID NO: 46. In certain embodiments, the editing element comprises the nucleotide sequences set forth in SEQ ID NOs: 43, 44, and 45. In certain embodiments, the editing element comprises the nucleotide sequences set forth in SEQ ID NOs: 105, 106, and 107.

In certain embodiments, the editing element comprises at least a portion of an HBB coding sequence that has been silently altered to be less than 100% (e.g., less than 95%, 90%, 85%, 80%, 75%, 70%, 65%, 60%, 55%, or 50%) identical to the corresponding portion of the wild-type HBB coding sequence. In certain embodiments, the editing element comprises at least a portion of an HBB coding sequence that has been silently altered to be less than 70% identical to the corresponding portion of the wild-type HBB coding sequence. In certain embodiments, the editing element comprises at least a portion of an HBB coding sequence that has been silently altered to be less than 85% identical to the corresponding portion of the wild-type HBB coding sequence.

In certain embodiments, the editing element comprises at least a portion of an HBB stuffer-inserted coding sequence that has been silently altered, such that the at least a portion of HBB stuffer-inserted coding sequence can be transcribed and spliced into a coding sequence less than 100% (e.g., less than 95%, 90%, 85%, 80%, 75%, 70%, 65%, 60%, 55%, or 50%) identical to the corresponding portion of the wild-type HBB coding sequence. In certain embodiments, the editing element comprises at least a portion of an HBB stuffer-inserted coding sequence that has been silently altered, such that the at least a portion of HBB stuffer-inserted coding sequence can be transcribed and spliced into a coding sequence less than 70% identical to the corresponding portion of the wild-type HBB coding sequence. In certain embodiments, the editing element comprises at least a portion of an HBB stuffer-inserted coding sequence that has been silently altered, such that the at least a portion of HBB stuffer-inserted coding sequence can be transcribed and spliced into a coding sequence less than 85% identical to the corresponding portion of the wild-type HBB coding sequence.

In certain embodiments, the editing element comprises nucleotides 4 to 444 of an HBB coding sequence that has been silently altered to be less than 100% (e.g., less than 95%, 90%, 85%, 80%, 75%, 70%, 65%, 60%, 55%, or 50%) identical to the corresponding portion of the wild-type HBB coding sequence. In certain embodiments, the editing element comprises nucleotides 4 to 444 of an HBB coding sequence that has been silently altered to be less than 70% identical to the corresponding portion of the wild-type HBB coding sequence. In certain embodiments, the editing element comprises the nucleotide sequence set forth in SEQ ID NO: 47. In certain embodiments, the editing element comprises nucleotides 4 to 444 of an HBB coding sequence that has been silently altered to be less than 85% identical to the corresponding portion of the wild-type HBB coding sequence. In certain embodiments, the editing element comprises the nucleotide sequence set forth in SEQ ID NO: 100. Such editing elements can further comprise an exogenous polyadenylation sequence 3' to the HBB gene coding sequence. In certain embodiments, the editing element comprises 5' to 3': nucleotides 4 to 444 of an HBB coding sequence; and an exogenous polyadenylation sequence, wherein the nucleotides 4 to 444 of an HBB coding sequence have been silently altered to be less than 100% (e.g., less than 95%, 90%, 85%, 80%, 75%, 70%, 65%, 60%, 55%, or 50%) identical to the corresponding region of the wild-type HBB coding sequence.

In certain embodiments, the editing element comprises a portion of HBB stuffer-inserted coding sequence that has been silently altered, such that the portion of HBB stuffer-inserted coding sequence can be transcribed and spliced into nucleotides 4 to 444 of an HBB coding sequence that is less than 100% (e.g., less than 95%, 90%, 85%, 80%, 75%, 70%, 65%, 60%, 55%, or 50%) identical to the corresponding portion of the wild-type HBB coding sequence. In certain embodiments, the editing element comprises a portion of HBB stuffer-inserted coding sequence that has been silently altered, such that the portion of HBB stuffer-inserted coding sequence can be transcribed and spliced into nucleotides 4 to 444 of an HBB coding sequence that is less than 70% identical to the corresponding portion of the wild-type HBB coding sequence. In certain embodiments, the portion of HBB stuffer-inserted coding sequence can be transcribed and spliced into the nucleotide sequence set forth in SEQ ID NO: 47. In certain embodiments, the editing element comprises a portion of HBB stuffer-inserted coding sequence that has been silently altered, such that the portion of HBB stuffer-inserted coding sequence can be transcribed and spliced into nucleotides 4 to 444 of an HBB coding sequence that is less than 85% identical to the corresponding portion of the wild-type HBB coding sequence. In certain embodiments, the portion of HBB stuffer-inserted coding sequence can be transcribed and spliced into the nucleotide sequence set forth in SEQ ID NO: 100. Such editing elements can further comprise an exogenous polyadenylation sequence 3' to the HBB gene coding sequence. In certain embodiments, the editing element comprises 5' to 3': a portion of HBB stuffer-inserted coding sequence that has been silently altered; and an exogenous polyadenylation sequence, wherein the portion of HBB stuffer-inserted coding sequence can be transcribed and spliced into nucleotides 4 to 444 of an HBB coding sequence that is less than 100% (e.g., less than 95%, 90%, 85%, 80%, 75%, 70%, 65%, 60%, 55%, or 50%) identical to the corresponding region of the wild-type HBB coding sequence.

In certain embodiments, the editing element comprises a complete HBB coding sequence that has been silently altered to be less than 100% (e.g., less than 95%, 90%, 85%, 80%, 75%, 70%, 65%, 60%, 55%, or 50%) identical to the wild-type HBB coding sequence. In certain embodiments, the editing element comprises a complete HBB coding sequence that has been silently altered to be less than 70% identical to the wild-type HBB coding sequence. In certain embodiments, the editing element comprises 5' to 3' a start codon and the nucleotide sequence set forth in SEQ ID NO: 47. In certain embodiments, the editing element comprises the nucleotide sequence set forth in SEQ ID NO: 28. In certain embodiments, the editing element comprises a complete HBB coding sequence of an HBB gene that has been silently altered to be less than 85% identical to the wild-type HBB coding sequence. In certain embodiments, the editing element comprises 5' to 3' a start codon and the nucleotide sequence set forth in SEQ ID NO: 100. In certain embodiments, the editing element comprises the nucleotide sequence set forth in SEQ ID NO: 99. Such editing elements can further comprise one or more of: a splice acceptor site; a ribosomal skipping element; and an exogenous polyadenylation sequence 3' to the HBB gene coding sequence. In certain embodiments, the editing element comprises 5' to 3': a ribosomal skipping element; and a complete HBB coding sequence optionally lacking the start codon, wherein the complete HBB coding sequence has been silently altered to be less than 100% (e.g., less than 95%, 90%, 85%, 80%, 75%, 70%, 65%, 60%, 55%, or 50%) identical to the corresponding region of the wild-type HBB coding sequence. In certain embodiments, the editing element comprises 5' to 3': a ribosomal skipping element; a complete HBB coding sequence optionally lacking the start codon; and an exogenous polyadenylation sequence, wherein the complete HBB coding sequence has been silently altered to be less than 100% (e.g., less than 95%, 90%, 85%, 80%, 75%, 70%, 65%, 60%, 55%, or 50%) identical to the corresponding region of the wild-type HBB coding sequence. In certain embodiments, the editing element comprises 5' to 3': a splice acceptor site; a ribosomal skipping element; and a complete HBB coding sequence optionally lacking the start codon, wherein the complete HBB coding sequence has been silently altered to be less than 100% (e.g., less than 95%, 90%, 85%, 80%, 75%, 70%, 65%, 60%, 55%, or 50%) identical to the corresponding region of the wild-type HBB coding sequence. In certain embodiments, the editing element comprises 5' to 3': a splice acceptor site; a ribosomal skipping element; a complete HBB coding sequence optionally lacking the start codon; and an exogenous polyadenylation sequence, wherein the complete HBB coding sequence has been silently altered to be less than 100% (e.g., less than 95%, 90%, 85%, 80%, 75%, 70%, 65%, 60%, 55%, or 50%) identical to the corresponding region of the wild-type HBB coding sequence.

In certain embodiments, the editing element comprises an HBB stuffer-inserted coding sequence that has been silently altered, such that the HBB stuffer-inserted coding sequence can be transcribed and spliced into a complete HBB coding sequence that is less than 100% (e.g., less than 95%, 90%, 85%, 80%, 75%, 70%, 65%, 60%, 55%, or 50%) identical to the wild-type HBB coding sequence. In certain embodiments, the editing element comprises an HBB stuffer-inserted coding sequence that has been silently altered, such that the HBB stuffer-inserted coding sequence can be transcribed and spliced into a complete HBB coding sequence that is less than 70% identical to the wild-type HBB coding sequence. In certain embodiments, the complete HBB coding sequence consists of 5' to 3' a start codon and the nucleotide sequence set forth in SEQ ID NO: 47. In certain embodiments, the complete HBB coding sequence consists of the nucleotide sequence set forth in SEQ ID NO: 28. In certain embodiments, the HBB stuffer-inserted coding sequence comprises the nucleotide sequences set forth in SEQ ID NOs: 43-45. In certain embodiments, the editing element comprises an HBB stuffer-inserted coding sequence that has been silently altered, such that the HBB stuffer-inserted coding sequence can be transcribed and spliced into a complete HBB coding sequence that is less than 85% identical to the wild-type HBB coding sequence. In certain embodiments, the HBB stuffer-inserted coding sequence comprises 5' to 3' the nucleotide sequences set forth in SEQ ID NOs: 105, 106, and 107. Such editing elements can further comprise one or more of: a splice acceptor site; a ribosomal skipping element; and an exogenous polyadenylation sequence 3' to the HBB gene coding sequence. In certain embodiments, the editing element comprises 5' to 3': a ribosomal skipping element; and an HBB stuffer-inserted coding sequence that has been silently altered, wherein the HBB stuffer-inserted coding sequence can be transcribed and spliced into a complete HBB coding sequence that is less than 100% (e.g., less than 95%, 90%, 85%, 80%, 75%, 70%, 65%, 60%, 55%, or 50%) identical to the corresponding region of the wild-type HBB coding sequence. In certain embodiments, the editing element comprises 5' to 3': a ribosomal skipping element; an HBB stuffer-inserted coding sequence that has been silently altered; and an exogenous polyadenylation sequence, wherein the HBB stuffer-inserted coding sequence can be transcribed and spliced into a complete HBB coding sequence that is less than 100% (e.g., less than 95%, 90%, 85%, 80%, 75%, 70%, 65%, 60%, 55%, or 50%) identical to the corresponding region of the wild-type HBB coding sequence. In certain embodiments, the editing element comprises 5' to 3': a splice acceptor site; a ribosomal skipping element; and an HBB stuffer-inserted coding sequence that has been silently altered, wherein the HBB stuffer-inserted coding sequence can be transcribed and spliced into a complete HBB coding sequence that is less than 100% (e.g., less than 95%, 90%, 85%, 80%, 75%, 70%, 65%, 60%, 55%, or 50%) identical to the corresponding region of the wild-type HBB coding sequence. In certain embodiments, the editing element comprises 5' to 3': a splice acceptor site; a ribosomal skipping element; an HBB stuffer-inserted coding sequence that has been silently altered; and an exogenous polyadenylation sequence, wherein the HBB stuffer-inserted coding sequence can be transcribed and spliced into a complete HBB coding sequence that is less than 100% (e.g., less than 95%, 90%, 85%, 80%, 75%, 70%, 65%, 60%, 55%, or 50%) identical to the corresponding region of the wild-type HBB coding sequence.

Any and all of the editing elements disclosed herein can further include a unique sequence not present in the target gene (e.g., wild-type or mutant HBB gene, or a gene encoding a functional equivalent thereof), thereby allowing for identification of cells that have integration of the editing element at the target locus. Such unique sequence can be a suitable sequence for nucleic acid sequencing analysis (e.g., by PCR or next-generation sequencing) of the target locus and its flanking regions or a nucleic acid amplified therefrom. Such unique sequence can also be a restriction endonuclease site that allows for identification of cells that have integration of the editing element at the target locus based upon restriction fragment length polymorphism analysis of the target locus and its flanking regions or a nucleic acid amplified therefrom.

Any and all of the editing elements disclosed herein can comprise one or more nucleotide alterations that cause one or more amino acid modifications (e.g., substitution, insertion, or deletion) in beta globin protein when integrated into the target locus. In certain embodiments, the modified beta globin protein is a functional equivalent of the wild-type beta globin, i.e., can function as a wild-type beta globin. In certain embodiments, the functionally equivalent beta globin further comprises at least one characteristic not found in wild-type beta globin, e.g., the ability to inhibit aggregation of beta globin carrying the SCD mutation.

In certain embodiments, an editing element as described herein comprises at least 0, 1, 2, 10, 100, 200, 500, 1000, 1500, 2000, 3000, 4000, or 5000 nucleotides. In certain embodiments, the editing element comprises or consists of 1 to 5000, 1 to 4500, 1 to 4000, 1 to 3000, 1 to 2000, 1 to 1000, 1 to 500, 1 to 200, 1 to 100, 1 to 50, or 1 to 10 nucleotides.

In certain embodiments, an editing element as described herein comprises or consists of an exon, an intron, a 5' untranslated region (UTR), a 3' UTR, a promoter, a splice donor, a splice acceptor, a ribosomal skipping element, a sequence encoding a non-coding RNA, an insulator, a gene, or a combination thereof.

In certain embodiments, the editing element comprises the nucleotide sequence set forth in any one of SEQ ID NOs: 23-28. In certain embodiments, the editing element consists of the nucleotide sequence set forth in any one of SEQ ID NOs: 23-26.

Homology arms used in the correction genomes disclosed herein can be directed to any region of the target gene (e.g., the HBB gene) or a gene nearby on the genome. The precise identity and positioning of the homology arms are determined by the identity of the editing element and/or the target locus.

Homology arms employed in the correction genomes disclosed herein are substantially identical to the genome flanking a target locus (e.g., a target locus in the HBB gene). In certain embodiments, the 5' homology arm has at least about 90% (e.g., at least about 95%, 96%, 97%, 98%, 99%, or 99.5%) nucleotide sequence identity to a first genomic region 5' to the target locus. In certain embodiments, the 5' homology arm has 100% nucleotide sequence identity to the first genomic region. In certain embodiments, the 3' homology arm has at least about 90% (e.g., at least about 95%, 96%, 97%, 98%, 99%, or 99.5%) nucleotide sequence identity to a second genomic region 3' to the target locus. In certain embodiments, the 3' homology arm has 100% nucleotide sequence identity to the second genomic region. In certain embodiments, the 5' and 3' homology arms are each at least about 90% (e.g., at least about 95%, 96%, 97%, 98%, 99%, or 99.5%) identical to a first genomic region 5' to the target locus and a second genomic region 3' to the target locus, respectively. In certain embodiments, the 5' and 3' homology arms are each 100% identical to the first and second genomic regions, respectively. In certain embodiments, the differences in nucleotide sequences of the 5' homology arm and the first genomic region, and/or the difference in nucleotide sequences of the 3' homology arm and the second genomic region, comprise, consist essentially of or consist of non-coding differences in nucleotide sequences.

The skilled worker will appreciate that homology arms do not need to be 100% identical to the genomic sequence flanking the target locus to be able to mediate integration of an editing element into that target locus by homologous recombination. The skilled worker will further appreciate that in situations where a homology arm is not 100% identical to the genomic sequence flanking the target locus, homologous recombination between the homology arm and the genome may alter the genomic sequence flanking the target locus such that it becomes identical to the sequence of the homology arm used.

In certain embodiments, the first genomic region 5' to the target locus is located in a first editing window, wherein the nucleotide sequence of the first editing window consists of a sequence selected from the group consisting of SEQ ID NOs: 101-103. In certain embodiments, the second genomic region 3' to the target locus is located in a second editing window, wherein the nucleotide sequence of the second editing window consists of a sequence selected from the group consisting of SEQ ID NOs: 101-103. In certain embodiments, the first genomic region 5' to the target locus is located in a first editing window, wherein the nucleotide sequence of the first editing window consists of a sequence selected from the group consisting of SEQ ID NOs: 101-103; and the second genomic region 3' to the target locus is located in a second editing window, wherein the nucleotide sequence of the second editing window consists of a nucleotide sequence set forth in SEQ ID NO: 101, 102, or 103.

In certain embodiments, the first and second editing windows are different. In certain embodiments, the first editing window is located 5' to the second editing window. In certain embodiments, the first editing window consists of the nucleotide sequence set forth in SEQ ID NO: 101. In certain embodiments, the second editing window consists of the nucleotide sequence set forth in SEQ ID NO: 102. In certain embodiments, the first editing window consists of the nucleotide sequence set forth in SEQ ID NO: 101, and the second editing window consists of the nucleotide sequence set forth in SEQ ID NO: 102. In certain embodiments, the first genomic region consists of a sequence that is shorter than the sequence of the first editing window. In certain embodiments, the first genomic region consists of the sequence of the first editing window. In certain embodiments, the second genomic region consists of a sequence that is shorter than the sequence of the second editing window. In certain embodiments, the second genomic region consists of the sequence of the second editing window.

In certain embodiments, the first and second editing windows are the same. In certain embodiments, the target locus is an internucleotide bond or a nucleotide sequence in the editing window, wherein the first genomic locus consists of a first portion of the editing window 5' to the target locus, and the second genomic locus consists of a second portion of the editing window 3' to the target locus. In certain embodiments, the first portion of the editing window consists of the sequence from the 5' end of the editing window to the nucleotide adjacently 5' to the target locus. In certain embodiments, the second portion of the editing window consists of the sequence from the nucleotide adjacently 3' to the target locus to the 3' end of the editing window. In certain embodiments, the first portion of the editing window consists of the sequence from the 5' end of the editing window to the nucleotide adjacently 5' to the target locus, and the second portion of the editing window consists of the sequence from the nucleotide adjacently 3' to the target locus to the 3' end of the editing window. In certain embodiments, the editing window consists of the nucleotide sequence set forth in SEQ ID NO: 103. In certain embodiments, the first and second portions of the editing windows have substantially equal lengths (e.g., the ratio of the length of the shorter portion to the length of the longer portion is greater than 0.5, 0.55, 0.6, 0.65, 0.7, 0.75, 0.8, 0.85, 0.9, 0.95, 0.96, 0.97, 0.98, or 0.99).

In certain embodiments, the 5' homology arm has a length of about 50 to about 4000 nucleotides (e.g., about 100 to about 3000, about 200 to about 2000, about 500 to about 1000 nucleotides). In certain embodiments, the 5' homology arm has a length of about 800 nucleotides. In certain embodiments, the 5' homology arm has a length of about 100 nucleotides. In certain embodiments, the 3' homology arm has a length of about 50 to about 4000 nucleotides (e.g., about 100 to about 3000, about 200 to about 2000, about 500 to about 1000 nucleotides). In certain embodiments, the 3' homology arm has a length of about 800 nucleotides. In certain embodiments, the 3' homology arm has a length of about 100 nucleotides. In certain embodiments, each of the 5' and 3' homology arms independently has a length of about 50 to about 4000 nucleotides (e.g., about 100 to about 3000, about 200 to about 2000, about 500 to about 1000 nucleotides). In certain embodiments, the 5' and 3'homology arm has a length of about 800 nucleotides.

In certain embodiments, the 5' and 3' homology arms have substantially equal nucleotide lengths. In certain embodiments, the 5' and 3' homology arms have asymmetrical nucleotide lengths. In certain embodiments, the asymmetry in nucleotide length is defined by a difference between the 5' and 3' homology arms of up to 90% in the length, such as up to an 80%, 70%, 60%, 50%, 40%, 30%, 20%, or 10% difference in the length.

In certain embodiments, the correction genome comprises the nucleotide sequence set forth in any one of SEQ ID NOs: 29-42.

In certain embodiments, the correction genome comprises 5' to 3': the sequence set forth in SEQ ID NO: 101; a ribosomal skipping element; an HBB coding sequence that has been silently altered to be less than 95%, 90%, 85%, 80%, 75%, 70%, 65%, 60%, 55%, or 50% identical to the wild-type HBB coding sequence; an exogenous polyadenylation sequence (e.g., as set forth in SEQ ID NO: 76, 77, 78, or 79); and the sequence set forth in SEQ ID NO: 102. In certain embodiments, the correction genome comprises 5' to 3': the sequence set forth in SEQ ID NO: 101; a ribosomal skipping element; the sequence set forth in SEQ ID NO: 99; an exogenous polyadenylation sequence (e.g., as set forth in SEQ ID NO: 76, 77, 78, or 79); and the sequence set forth in SEQ ID NO: 102. In certain embodiments, the correction genome comprises 5' to 3': the sequence set forth in SEQ ID NO: 101; a ribosomal skipping element; the coding region of the first exon of HBB that has been silently altered to be less than 95%, 90%, 85%, 80%, 75%, 70%, 65%, 60%, 55%, or 50% identical to wild-type coding region of the first exon of HBB; an optional first nonnative intron; the second exon of HBB that has been silently altered to be less than 95%, 90%, 85%, 80%, 75%, 70%, 65%, 60%, 55%, or 50% identical to wild-type second exon of HBB; an optional second intron; the coding region of the third exon of HBB that has been silently altered to be less than 95%, 90%, 85%, 80%, 75%, 70%, 65%, 60%, 55%, or 50% identical to wild-type coding region of the third exon of HBB; an exogenous polyadenylation sequence (e.g., as set forth in SEQ ID NO: 76, 77, 78, or 79); and the sequence set forth in SEQ ID NO: 102. In certain embodiments, the correction genome comprises 5' to 3': the sequence set forth in SEQ ID NO: 101; a ribosomal skipping element; the sequence set forth in SEQ ID NO: 105; an optional first nonnative intron; the sequence set forth in SEQ ID NO: 106; an optional second intron; the sequence set forth in SEQ ID NO: 107; an exogenous polyadenylation sequence (e.g., as set forth in SEQ ID NO: 76, 77, 78, or 79); and the sequence set forth in SEQ ID NO: 102. In certain embodiments, the correction genome comprises the nucleotide sequence set forth in SEQ ID NO: 104.

In certain embodiments, the correction genomes disclosed herein further comprise a 5' inverted terminal repeat (5' ITR) nucleotide sequence 5' of the 5' homology arm nucleotide sequence, and a 3' inverted terminal repeat (3' ITR) nucleotide sequence 3' of the 3' homology arm nucleotide sequence. ITR sequences from any AAV serotype or variant thereof can be used in the correction genomes disclosed herein. The 5' and 3' ITR can be from an AAV of the same serotype or from AAVs of different serotypes. Exemplary ITRs for use in the correction genomes disclosed herein are set forth in SEQ ID NO: 18-21 herein. In certain embodiments, the 5' ITR nucleotide sequence and the 3' ITR nucleotide sequence are substantially complementary to each other (e.g., are complementary to each other except for mismatch at 1, 2, 3, 4 or 5 nucleotide positions in the 5' or 3' ITR).

In certain embodiments, the 5' ITR or 3' ITR is from AAV2. In certain embodiments, both the 5' ITR and the 3' ITR are from AAV2. In certain embodiments, the 5' ITR nucleotide sequence has at least 95% (e.g., at least 96%, at least 97%, at least 98%, at least 99%, or 100%) sequence identity to SEQ ID NO:18, or the 3' ITR nucleotide sequence has at least 95% (e.g., at least 96%, at least 97%, at least 98%, at least 99%, or 100%) sequence identity to SEQ ID NO:19. In certain embodiments, the 5' ITR nucleotide sequence has at least 95% (e.g., at least 96%, at least 97%, at least 98%, at least 99%, or 100%) sequence identity to SEQ ID NO:18, and the 3' ITR nucleotide sequence has at least 95% (e.g., at least 96%, at least 97%, at least 98%, at least 99%, or 100%) sequence identity to SEQ ID NO:19. In certain embodiments, the correction genome comprises an editing element having the nucleotide sequence set forth in any one of SEQ ID NOs: 23-28, a 5' ITR nucleotide sequence having the sequence of SEQ ID NO:18, and a 3' ITR nucleotide sequence having the sequence of SEQ ID NO:19. In certain embodiments, the correction genome comprises the nucleotide sequence set forth in any one of SEQ ID NOs: 29-42, a 5' ITR nucleotide sequence having the sequence of SEQ ID NO:18, and a 3' ITR nucleotide sequence having the sequence of SEQ ID NO:19. In certain embodiments, the correction genome consists of 5' to 3' a 5' ITR nucleotide sequence having the sequence of SEQ ID NO:18, the nucleotide sequence set forth in any one of SEQ ID NOs: 29-42, and a 3' ITR nucleotide sequence having the sequence of SEQ ID NO: 19.

In certain embodiments, the 5' ITR or 3' ITR are from AAV5. In certain embodiments, both the 5' ITR and 3' ITR are from AAV5. In certain embodiments, the 5' ITR nucleotide sequence has at least 95% (e.g., at least 96%, at least 97%, at least 98%, at least 99%, or 100%) sequence identity to SEQ ID NO:20, or the 3' ITR nucleotide sequence has at least 95% sequence identity to SEQ ID NO:21. In certain embodiments, the 5' ITR nucleotide sequence has at least 95% (e.g., at least 96%, at least 97%, at least 98%, at least 99%, or 100%) sequence identity to SEQ ID NO:20, and the 3' ITR nucleotide sequence has at least 95% (e.g., at least 96%, at least 97%, at least 98%, at least 99%, or 100%) sequence identity to SEQ ID NO:21. In certain embodiments, the correction genome comprises an editing element having the nucleotide sequence set forth in any one of SEQ ID NOs: 23-28, a 5' ITR nucleotide sequence having the sequence of SEQ ID NO:20, and a 3' ITR nucleotide sequence having the sequence of SEQ ID NO:21. In certain embodiments, the correction genome comprises the nucleotide sequence set forth in any one of SEQ ID NOs: 29-42, a 5' ITR nucleotide sequence having the sequence of SEQ ID NO:20, and a 3' ITR nucleotide sequence having the sequence of SEQ ID NO:21. In certain embodiments, the correction genome consists of 5' to 3' a 5' ITR nucleotide sequence having the sequence of SEQ ID NO:20, the nucleotide sequence set forth in any one of SEQ ID NOs: 29-42, and a 3' ITR nucleotide sequence having the sequence of SEQ ID NO:21.

In certain embodiments, the correction genome disclosed herein has a length of about 0.5 to about 8 kb, and any range enclosed therebetween (e.g., about 1 to about 5, about 2 to about 5, about 3 to about 5, about 4 to about 5, about 4.5 to about 4.8, or about 4.7 kb).

The correction genomes disclosed herein can be configured to integrate an editing element into any desired target locus of the HBB gene. In certain embodiments, the target locus is a mutation (e.g., insertion, deletion or substitution of one or more nucleotides) in an HBB gene sequence relative to the corresponding wild-type HBB gene sequence. In certain embodiments, the target locus is at a nucleotide point mutation or deletion in the HBB gene. Exemplary HBB point mutations or deletion include, without limitation, G at position −87, G at position −31, A at position −30, G at position −29, G at position −28, T at position −10, C at position 1, A at position 1, G at position 2, deletion of C and T at positions 17 and 18, A at position 19, deletion of A at position 20, T at position 20, deletion of A and A at positions 25 and 26, addition of G after position 26, A at position 47, A at position 48, deletion of C at position 51, A at position 52, G at position 58, G at position 59, A at position 79, T at position 82, addition of C after position 84, T at position 93, A at position 93, C at position 97, C at position 98, G at position 202, G at position 208, C at position 222, deletion of T at position 241 or 242, deletion of T and T and C and T at positions 254 to 257, T at position 260, deletion of C at position 264 or 265, addition of A after position 343, deletion of G and T at positions 399 and 400, T at position 401, addition of A after position 417, A at position 446, T at position 1099, A at position 1293, T at position 1344. In certain embodiments, the target locus is the sickle cell disease mutation (i.e., T at position 20 of the HBB gene). In certain embodiments, the target locus is a region of chromosome or an internucleotide bond in exon 1 of the HBB gene, e.g., immediately following the endogenous start codon (e.g., the internucleotide bond between nucleotide 3 and nucleotide 4 of the HBB gene). In certain embodiments, the target locus is a region of chromosome or an internucleotide bond in intron 1 of the HBB gene. In certain embodiments, the target locus consists of the native stop codon of a wild-type HBB gene or the corresponding nucleotides of a mutant HBB gene. In certain embodiments, the target locus consists of the internucleotide bond adjacently 5' to the stop codon of a wild-type HBB gene or the corresponding internucleotide bond of a mutant HBB gene.

The AAV compositions disclosed herein are particular advantageous in that they are capable of correcting a mutation in an HBB gene in a cell with high efficiency both in vivo and in vitro. In certain embodiments, the integration efficiency of the editing element into the target locus is at least 0.1% (e.g. at least 0.2%, 0.3%, 0.4%, 0.5%, 0.6%, 0.7%, 0.8%, 0.9%, 1%, 1.5%, 2%, 2.5%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is contacted in vitro in the absence of an exogenous nuclease with a population of $CD34^+$ human hematopoietic stem cells under standard AAV transduction conditions. In certain embodiments, the allelic frequency of integration of the editing element into the target locus is at least 0.05% (e.g. at least 0.1%, 0.2%, 0.3%, 0.4%, 0.5%, 0.6%, 0.7%, 0.8%, 0.9%, 1%, 1.5%, 2%, 2.5%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is contacted in vitro in the absence of an exogenous nuclease with a population of $CD34^+$ human hematopoietic stem cells under standard AAV transduction conditions.

Any methods of determining the efficiency of gene editing can be employed. In certain embodiments, individual cells are separated from the population of transduced cells and subject to single-cell PCR using PCR primers that can identify the presence of an editing element correctly integrated into the target locus. Such a method can further comprise single-cell PCR of the same cells using PCR primers that selectively amplify an unmodified target locus. In this way, the genotype of the cells can be determined. For example, if the single cell PCR showed that a cell has both an edited target locus and an unmodified target locus, then the cell would be considered heterozygous for the edited HBB gene.

Additionally or alternatively, in certain embodiments, linear amplification mediated PCR (LAM-PCR), quantitative PCR (qPCR) or digital droplet PCR (ddPCR) can be performed on DNA extracted from a population of transduced cells (e.g., a tissue or organ) to assess the allelic frequency of integration. In certain embodiments, the extracted DNA is analyzed by digital droplet PCR (ddPCR) using at least two pair of primers that detect different sequences. For example, the ddPCR can employ a first pair of primers that detect the unedited and edited target loci, a second pair of primers that detect a sequence present in the unintegrated and integrated vectors, and optionally a third pair of primers that detect a sequence in the homology arm, which is present in the unedited and edited target loci, as well as the unintegrated and integrated vectors. After correction of the chance of co-partitioning of an unedited genomic DNA and an unintegrated vector, the percentage of droplets positive with both the first and the second pair of primers corresponds to the allelic frequency of integration. An example of this method is described herein in Example 1.

Additionally or alternatively, in certain embodiments, the HBB locus can be amplified from DNA extracted from a population of transduced cells (e.g., a tissue or organ) either by PCR using primers that bind to regions of the HBB gene flanking the genomic region encompassed by the correction genome, or by linear amplification mediated PCR (LAM-PCR) using a primer that binds a region within the correction genome (e.g., a region comprising an exogenous sequence non-native to the locus. The resultant PCR amplicons can be individually sequenced using single molecule next generation sequencing (NGS) techniques to determine the relative number of edited and unedited HBB alleles present in the population of transduced cells. These numbers can be used to determine the allelic frequency of integration of the editing element into the target locus.

In another aspect, the instant disclosure provides pharmaceutical compositions comprising an AAV as disclosed herein together with a pharmaceutically acceptable excipient, adjuvant, diluent, vehicle or carrier, or a combination thereof. A "pharmaceutically acceptable carrier" includes any material which, when combined with an active ingredient of a composition, allows the ingredient to retain biological activity and without causing disruptive physiological reactions, such as an unintended immune reaction. Pharmaceutically acceptable carriers include water, phosphate buffered saline, emulsions such as oil/water emulsion, and wetting agents. Compositions comprising such carriers are formulated by well-known conventional methods such as those set forth in Remington's Pharmaceutical Sciences, current Ed., Mack Publishing Co., Easton Pa. 18042, USA; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al, 7th ed., Lippincott, Williams, & Wilkins; and Handbook of Pharmaceutical Excipients (2000) A. H. Kibbe et al, 3rd ed. Amer. Pharmaceutical Assoc.

III. METHOD OF USE

In another aspect, the instant disclosure provides methods for correcting a mutation in an HBB gene in a cell. The methods generally comprise transducing the cell with a replication-defective AAV as disclosed herein. Such methods are highly efficient at correcting mutations in an HBB gene and do not require cleavage of the genome at the target locus by the action of an exogenous nuclease (e.g., a meganuclease, a zinc finger nuclease, a transcriptional activator-like nuclease (TALEN), or an RNA-guided nuclease such as a Cas9) to facilitate such correction. Accordingly, in certain embodiments, the methods disclosed herein involve transducing the cell with a replication-defective AAV as disclosed herein without co-transducing or co-administering an exogenous nuclease or a nucleotide sequence that encodes an exogenous nuclease.

The methods disclosed herein can be applied to any cell harboring a mutation in an HBB gene. The skilled worker will appreciate that cells that are capable of differentiating into erythrocytes are of particular interest. Accordingly, in certain embodiments, the method is applied to stem cells, including without limitation, pluripotent stem cells, induced pluripotent stem cells (iPSCs), and hematopoietic stem cells (HSC). Exemplary HSCs to which the methods can be applied include without limitation, $CD34^+$ HSCs.

The methods disclosed herein can be performed in vitro for research purposes or can be performed ex vivo or in vivo for therapeutic purposes.

In certain embodiments, the cell to be transduced is taken from a subject and is transduced to correct a mutation in the HBB gene ex vivo according to the methods disclosed herein, and the transduced cell is subsequently administered back to the subject. Accordingly, in certain embodiments, the instant disclosure provides a method for treating a subject having a disease or disorder associated with an HBB gene mutation, the method comprising: transducing a stem cell (e.g., a $CD34^+$ hematopoietic stem cell) ex vivo with a replication-defective AAV as disclosed herein to obtain a transduced cell; and administering the transduced cell to the subject. The transduced cells can be selected for correct genetic integration and/or cultured for clonal expansion before administration to the subject. In certain embodiments, the stem cell to be transduced is obtained from bone marrow, cord blood, or peripheral blood, wherein the stem cell is optionally selected by a method based on one or more cell markers (e.g., cell size, cell density, and surface markers such as CD34). In certain embodiments, the stem cell is autologous, i.e., from the subject to which the cells after AAV transduction will be administered. In certain embodiments, the stem cell is allogeneic to the subject in need thereof, i.e., the stem cell is obtained from a donor that is genetically non-identical to the recipient subject. Accordingly, in certain embodiments, the instant disclosure provides a method for treating a subject having a disease or disorder associated with an HBB gene mutation, the method comprising: transducing an allogeneic stem cell (e.g., a CD34+ hematopoietic stem cell) ex vivo with a replication-defective AAV as disclosed herein to obtain a transduced cell; and administering the transduced cell to the subject. In certain embodiments, the allogeneic stem cell is derived from a matched donor. The skilled worker will recognize that for allogeneic applications, the transduced cell may require further modifications before administration, e.g., genetic modifications to prevent and/or reduce the occurrence of graft-versus-host disease (GVHD). The subject can be a human subject or a rodent subject (e.g., a mouse) containing human erythrocyte precursor cells. Suitable mouse subjects include with limitation, mice into which human stem cells (e.g., human $CD34^+$ HSCs) have been engrafted. Any disease or disorder associated with an HBB gene mutation can be treated using the methods disclosed herein. Suitable diseases or disorders include, without limitation, beta thalassemia or sickle cell disease. In certain embodiments, the cell is transduced without co-transducing an exogenous nuclease or a nucleotide sequence that encodes an exogenous nuclease.

In certain embodiments, the cell to be transduced is in a mammalian subject and the AAV is administered to the subject in an amount effective to transduce the cell in the subject. Accordingly, in certain embodiments, the instant disclosure provides a method for treating a subject having a disease or disorder associated with an HBB gene mutation, the method generally comprising administering to the subject an effective amount of a replication-defect as disclosed herein. The subject can be a human subject, a non-human primate subject (e.g., *Macaca fascicularis*), or a rodent subject (e.g., a mouse) containing human erythrocyte precursor cells. Suitable mouse subjects include without limitation, mice into which human stem cells (e.g., human $CD34^+$ HSCs) have been engrafted. Any disease or disorder associated with an HBB gene mutation can be treated using the methods disclosed herein. Suitable diseases or disorders include, without limitation, beta thalassemia or sickle cell disease. In certain embodiments, the cell is transduced without co-transducing or co-administering an exogenous nuclease or a nucleotide sequence that encodes an exogenous nuclease.

The methods disclosed herein are particularly advantageous in that they are capable of correcting an HBB gene in a cell with high efficiency both in vivo and in vitro. In certain embodiments, the integration efficiency of the editing element into the target locus is at least 0.1% (e.g. at least 0.2%, 0.3%, 0.4%, 0.5%, 0.6%, 0.7%, 0.8%, 0.9%, 1%, 1.5%, 2%, 2.5%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is contacted in vitro in the absence of an exogenous nuclease with a population of $CD34^+$ human stem cells under standard AAV transduction conditions. In certain embodiments, the allelic frequency of integration of the editing element into the target locus is at least 0.05% (e.g. at least 0.1%, 0.2%, 0.3%, 0.4%, 0.5%, 0.6%, 0.7%, 0.8%, 0.9%, 1%, 1.5%, 2%, 2.5%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is contacted in vitro in the absence of an exogenous nuclease with a population of $CD34^+$ human stem cells under standard AAV transduction conditions. Any methods of determining the efficiency of gene editing can be employed including, without limitation, those described herein.

In certain embodiments, transduction of a cell with an AAV composition disclosed herein can be performed as provided herein or by any method of transduction known to one of ordinary skill in the art. In certain embodiments, the cell may be contacted with the AAV at a multiplicity of infection (MOI) of 50,000; 100,000; 150,000; 200,000; 250,000; 300,000; 350,000; 400,000; 450,000; or 500,000, or at any MOI that provides for optimal transduction of the cell. In certain embodiments, the subject may be administered with the AAV at a dose of about $10^{11}$, $10^{12}$, $10^{13}$, $10^{14}$, or $10^{15}$ vector genomes per kg of body weight.

An AAV composition disclosed herein can be administered to a subject by any appropriate route including, without limitation, intravenous, intraperitoneal, subcutaneous, intramuscular, intransal, topical or intradermal routes. In certain embodiments, the composition is formulated for administration via intravenous injection or subcutaneous injection.

IV. AAV PACKAGING SYSTEMS

In another aspect, the instant disclosure provides packaging systems for recombinant preparation of a replication-defective AAV disclosed herein. Such packaging systems generally comprise: a Rep nucleotide sequence encoding one or more AAV Rep proteins; a Cap nucleotide sequence encoding one or more AAV Clade F capsid proteins as disclosed herein; and a correction genome for correction of a mutation in the HBB gene as disclosed herein, wherein the packaging system is operative in a cell for enclosing the correction genome in the capsid to form the AAV.

In certain embodiments, the packaging system comprises a first vector comprising the Rep nucleotide sequence and the Cap nucleotide sequence, and a second vector comprising the correction genome. As used in the context of a packaging system as described herein, a "vector" refers to a nucleic acid molecule that is a vehicle for introducing nucleic acids into a cell (e.g., a plasmid, a virus, a cosmid, an artificial chromosome, etc.).

Any AAV Rep protein can be employed in the packaging systems disclosed herein. In certain embodiments of the packaging system, the Rep nucleotide sequence encodes an AAV2 Rep protein. Suitable AAV2 Rep proteins include, without limitation, Rep 78/68 or Rep 68/52. In certain embodiments of the packaging system, the nucleotide sequence encoding the AAV2 Rep protein comprises a nucleotide sequence that encodes a protein having a minimum percent sequence identity to the AAV2 Rep amino acid sequence of SEQ ID NO:22, wherein the minimum percent sequence identity is at least 70% (e.g., at least 75%, at least 80%, at least 85%, at least 90%, at least 95%, at least 98%, at least 99%, or 100%) across the length of the amino acid sequence of the AAV2 Rep protein. In certain embodiments of the packaging system, the AAV2 Rep protein has the amino acid sequence set forth in SEQ ID NO:22.

In certain embodiments of the packaging system, the packaging system further comprises a third vector, e.g., a helper virus vector. The third vector may be an independent third vector, integral with the first vector, or integral with the second vector. In certain embodiments, the third vector comprises genes encoding helper virus proteins.

In certain embodiments of the packaging system, the helper virus is selected from the group consisting of adenovirus, herpes virus (including herpes simplex virus (HSV)), poxvirus (such as vaccinia virus), cytomegalovirus (CMV), and baculovirus. In certain embodiments of the packaging system, where the helper virus is adenovirus, the adenovirus genome comprises one or more adenovirus RNA genes selected from the group consisting of E1, E2, E4 and VA. In certain embodiments of the packaging system, where the helper virus is HSV, the HSV genome comprises one or more of HSV genes selected from the group consisting of UL5/8/52, ICPO, ICP4, ICP22 and UL30/UL42.

In certain embodiments of the packaging system, the first, second, and/or third vector are contained within one or more transfecting plasmids. In certain embodiments, the first vector and the third vector are contained within a first transfecting plasmid. In certain embodiments the second vector and the third vector are contained within a second transfecting plasmid.

In certain embodiments of the packaging system, the first, second, and/or third vector are contained within one or more recombinant helper viruses. In certain embodiments, the first vector and the third vector are contained within a recombinant helper virus. In certain embodiments, the second vector and the third vector are contained within a recombinant helper virus.

In a further aspect, the disclosure provides a method for recombinant preparation of an AAV as described herein, wherein the method comprises transfecting or transducing a cell with a packaging system as described under conditions operative for enclosing the correction genome in the capsid to form the AAV as described herein. Exemplary methods for recombinant preparation of an AAV include transient transfection (e.g., with one or more transfection plasmids containing a first, and a second, and optionally a third vector as described herein), viral infection (e.g. with one or more recombinant helper viruses, such as a adenovirus, poxvirus (such as vaccinia virus), herpes virus (including HSV, cytomegalovirus, or baculovirus, containing a first, and a second, and optionally a third vector as described herein), and stable producer cell line transfection or infection (e.g., with a stable producer cell, such as a mammalian or insect cell, containing a Rep nucleotide sequence encoding one or more AAV Rep proteins and/or a Cap nucleotide sequence encoding one or more AAV Clade F capsid proteins as described herein, and with a correction genome as described herein being delivered in the form of a transfecting plasmid or a recombinant helper virus).

V. EXAMPLES

The recombinant AAV vectors disclosed herein mediate highly efficient gene editing in vitro and in vivo via a nuclease-free homology dependent repair based mechanism. The following examples demonstrate the efficient correction of an HBB gene which is mutated in certain human diseases, such as sickle cell disease (SCD) and beta thalassemia, using an AAV-based vector as disclosed herein. These examples are offered by way of illustration, and not by way of limitation.

Example 1: Selection of AAV Capsid for Gene Editing of HBB-Mutant Cells

This example characterizes the integration efficiency of a gene editing AAV vector, AAVS1-FP, packaged in clade F AAV capsids, such as AAVHSC7, AAVHSC15, and AAVHSC17, in HBB-mutant cells. AAVHSC7, AAVHSC15, and AAVHSC17, also known as AAVF7, AAVF15, and AAVF17, respectively, are fully described in WO2016049230A1, which is incorporated herein by reference in its entirety.

AAVS1-FP, the gene editing vector employed herein, was fully described in WO2016049230A1. It comprises from 5' to 3': an AAV2 5' inverted terminal repeat (ITR), a 5' homology arm consisting of 800 nucleotides having the sequence of the DNA upstream from a target locus, a splice acceptor, a 2A element, a coding sequence of a fluorescent protein (FP), a 3' homology arm consisting of 800 nucleotides having the sequence of the DNA downstream from a target locus, and an AAV2 3' ITR, wherein the target locus is in intron 1 of human PPP1R12C in the AAVS1 locus on chromosome 19, and wherein after homologous recombination between the AAVS1-FP vector and the human genome, exon 1 of PPP1R12C, the 2A element, and the FP coding sequence are in frame. Because the FP coding sequence in the vector is promoterless, cells transduced with this vector will express the FP only when the vector is integrated into the genome. AAVHSC-scEGFP, a self-complementary AAV vector comprising AAV2 ITRs and a promoter operably linked to enhanced green fluorescent protein (EGFP), served as a control for transduction efficiency (see e.g., U.S. Pat. No. 8,628,966, which is incorporated by reference herein in its entirety).

GM16265 cells, a lymphoblastoid cell line (LCL) having the A to T mutation at position 20 in intron 1 of HBB that is characteristic of sickle cell disease (SCD), were obtained from the Coriell Institute for Medical Research (Camden, NJ). The LCLs were cultured in RPMI supplemented with 15% FCS and 2 mM L-glutamine. Cells were seeded at approximately 200,000 cells per ml and split when reaching 500,000 to 1,000,000 cells per ml. Prior to plating cells, the amount of virus needed was calculated for each transduction. Transduction volume of the virus did not exceed 10% of the total volume of the well. On the day of transduction, log phase cells were counted and plated. Cells were transduced with viruses at a multiplicity of infection (MOI) of $1.5 \times 10^5$. Packaged AAV particles were thawed on ice and sonicated on ice if necessary prior to transduction, and were added to each well individually. The cells were harvested 48 hours after the transduction.

GM16265 cells were transduced with the AAVS1-FP vector packaged in AAVHSC7, AAVHSC15, or AAVHSC17 capsids. The integration efficiency was assessed by flow cytometry using the following method: cells were harvested using FACS Buffer (1×PBS, 2% FCS, 0.1% Sodium Azide) and centrifuged at 1200 RPM for 10 minutes. Excess supernatant was decanted so that approximately 200 µl remained. 4',6-Diamidino-2-Phenylindole (DAPI) was added from a 100 µM working stock immediately before flow cytometry analysis to a final concentration of 3 µM.

Figure 1B:
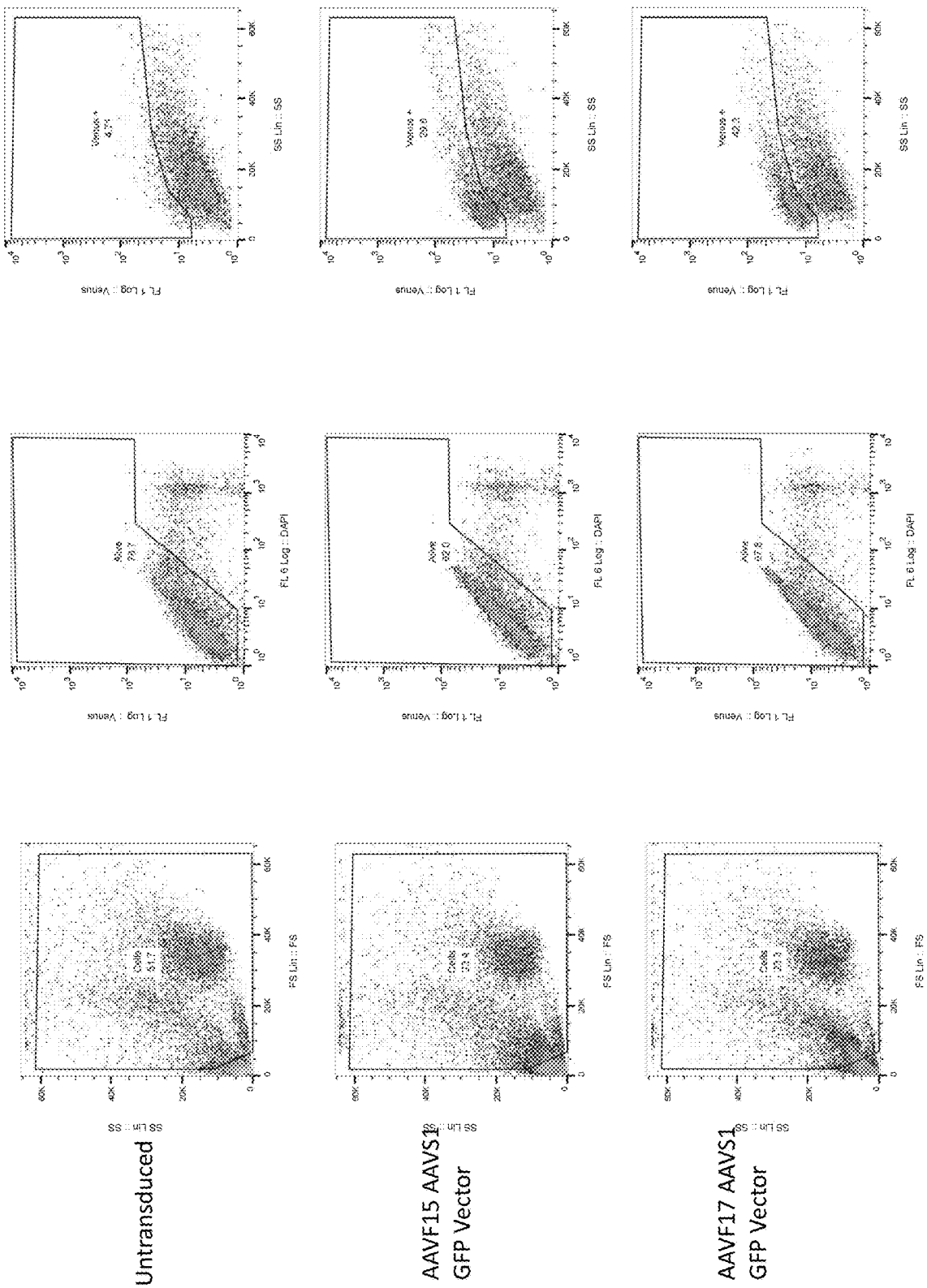

As shown in FIG. 1A, the percentages of FP-positive cells among all live cells transduced by AAVHSC7-AAVS1-FP and AAVHSC17-AAVS1-FP were 24.3% (34.0% minus background level 9.7%) and 7.8% (17.5% minus background level 9.7%), respectively. As shown in FIG. 1B, in another experiment, the percentages of FP-positive cells among all live cells transduced by AAVHSC15-AAVS1-FP and AAVHSC17-AAVS1-FP were 25.1% (29.8% minus background level 4.7%) and 37.6% (42.3% minus background level 4.7%), respectively. This data shows that GM16265 cells can be efficiently transduced by AAVS1-FP packaged in AAVHSC7, AAVHSC15, and AAVHSC17 capsids.

The integration efficiency of this AAVS1-FP vector packaged in an AAVHSC17 capsid was also examined in primary human CD34+ hematopoietic stem cells (HSCs). Primary human CD34+ HSCs were purified from human peripheral blood cells from donors with SCD by enriching with the Miltenyi CD34 MicroBeads twice, or were obtained from ReachBio Inc. that followed a similar double enrichment procedure. The cells were cultured in Iscove's Modified Dulbecco's Medium (IMDM) supplemented with 20% Fetal Calf Serum (FCS), 100 µg/mL streptomycin, 100 U/mL penicillin, 2 mmol/L L-glutamine, 10 ng/mL human IL-3, 10 ng/mL human IL-6, and 1 ng/mL human SCF. About 200,000 cells were plated in a 500 µl medium. AAV particles were added directly to the medium. The cells were harvested 48 hours after the transduction.

The editing efficiency was measured by digital droplet PCR (ddPCR) using the BioRad QX200™ Droplet Digital™ PCR System. Two sets of primers and probes, as shown in Table 1, were designed for quantifying the integration by ddPCR. The AAVS1_Genomic set detected a sequence at the AAVS1 locus that was present outside the homology arm in the unedited genome and the edited genome after the targeted integration of the FP coding sequence into the AAVS1 locus of the genome. The AAVS1_FP set detected a sequence in the FP coding region, which was present only in the edited genome after the targeted integration of the FP coding sequence into the AAVS1 locus of the genome. The two probes were conjugated to fluorescent moieties of different wavelengths.

TABLE 1

Primers for ddPCR analysis

| Primer Name | SEQ ID NO: | Nucleotide Sequence |
| --- | --- | --- |
| AAVS1_Genomic, forward primer | 90 | GCGTTAGAGGGCAGAGTTC |
| AAVS1_Genomic, reverse primer | 91 | AGCTCCCATAGCTCAGTCT |
| AAVS1_Genomic, probe | 92 | CATTGTCACTTTGCGCTGCCCTC |
| AAVS1_FP forward primer | 93 | GCAATAGCATCACAAATTTCAC |
| AAVS1_FP, reverse primer | 94 | GATCCAGACATGATAAGATACATTG |
| AAVS1_ FP, probe | 95 | TCACTGCATTCTAGTTGTGGTTTGTCCA |

Samples having 100 pg/µl of DNA were partitioned into oil droplets. Most of the oil droplets contained no DNA molecule or a single DNA molecule—an unedited genome, positive for only the AAVS1_Genomic set; an unintegrated vector, positive for only the AAVS1_FP set; or an edited genome, positive for both primer/probe sets. The chance of co-partitioning was determined by a number of standard samples (see Regan et al., A rapid molecular approach for chromosomal phasing, PLoS One. (2015) 10(3):e0118270, incorporated herein by reference in its entirety). The standard samples contained 100 unedited genomes per µl, 1000 episomal vector per µl, and a range of cloned positive alleles at 1, 5, 10, 15, 20, and 25 edited alleles per µl, respectively. A standard curve of co-partitioning against the ratio of unedited to edited allele was plotted ($R2=0.972$, Pearson correlation $p<0.001$).

Figure 1C:
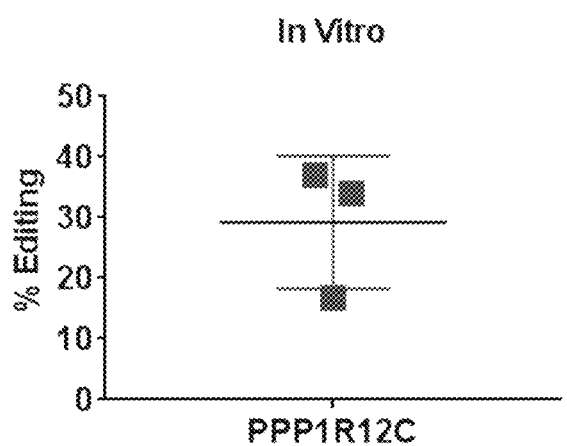
FIG. 1C is a graph showing the percentage of alleles having integration of the FP coding sequence in primary human CD34+ hematopoietic stem cells (HSCs) transduced with the AAVS1-FP vector packaged in AAVHSC17 capsid.

Each sample was analyzed by ddPCR in at least three experiments, and the amounts of AAVS1_Genomic positive, AAVS1_FP positive, and double positive droplets in each sample were measured and plotted against the known ratio of unedited to edited allele in each sample. As shown in FIG. 1C, integration of the FP coding sequence into the genome was detected in about 30% of all alleles from the primary human CD34+ HSCs. Accordingly, AAVS1-FP packaged in the AAVHSC17 capsid efficiently transduced primary human CD34+ HSCs.

Example 2: In Vitro Correction of an HBB Mutation

Figure 2:
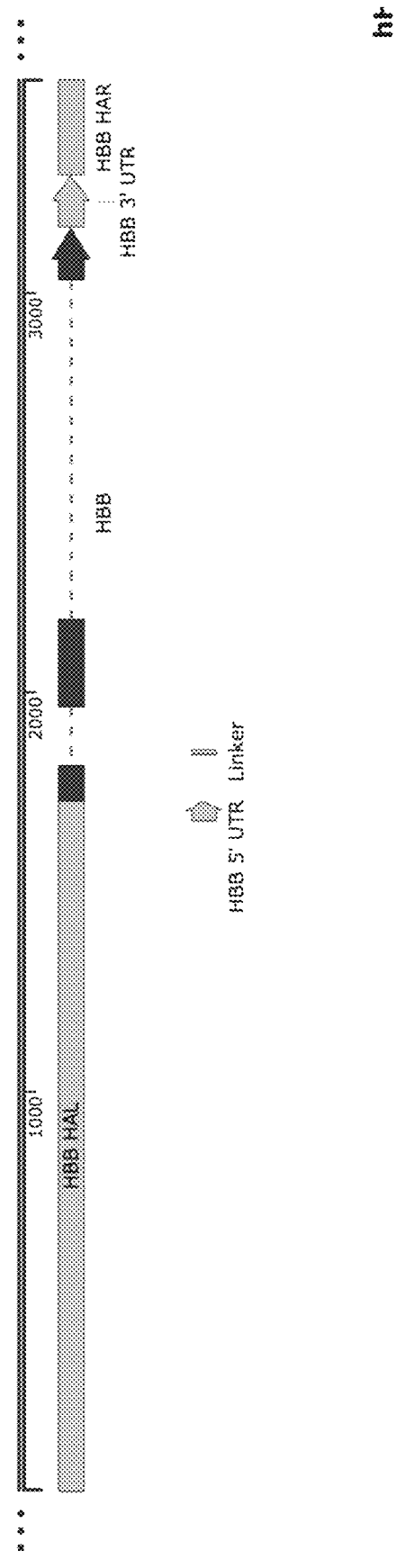
FIG. 2 depicts the plasmid map of the HBB correction vector hHBB-hL-014 containing a 12 bp linker. In this figure, the black regions of HBB denote nucleotide sequences in the exons encoding a human HBB protein, and the dashed lines between the black regions denote introns between the exons.

An AAV-based HBB correction vector named hHBB-hL-014, as shown in FIG. 2, was generated. This correction vector was designed to correct an HBB mutation, e.g., the A to T mutation at nucleotide 20 in the coding region of exon 1 (starting from the start codon) of the HBB gene in sickle cell disease. The hHBB-hL-014 vector included 5' and 3' AAV2 ITRs, flanking a portion of HBB and its neighboring genomic sequence, wherein the A to T mutation at nucleotide 20 in exon 1 was reversed. The portion of HBB genomic sequence was obtained from the wild type HBB and its neighboring loci using the amplification primers as shown in Table 2, which were designed using NCBI Primer Blast (www.ncbi.nlm.nih.gov/tools/primer-blast/). The PCR product covered all exons and introns of HBB, and further included 1678 nucleotides upstream from the HBB transcription initiation site and 234 nucleotides downstream from the HBB polyadenylation sequence. Relative to the HBB mutation in sickle cell disease, this vector contained homology arms (the genomic sequences 5' and 3' to the mutation reversion site) of about 1.7 kb in length each. Integrity of the ITRs was confirmed by restriction digest screening using BglII, MscI, and SmaI and sequencing using an ITR specific sequencing protocol (Mroske et al., Hum Gene Ther Methods (2012) 23(2): 128-36). The insert was verified by restriction digest and Sanger sequencing using the primers shown in Table 3 herein. This vector was able to correct not only mutations in the HBB exons and introns, but mutations in the 5' and 3' untranslated regions that affect HBB expression as observed in beta thalassemia.

TABLE 2

Human beta globin genomic region amplification primers

| Primer Name | SEQ ID NO: | Nucleotide Sequence |
| --- | --- | --- |
| HBB2M Gib 5' fwd | 50 | AGGGGTGGAGTCGTGACGTGCCAAATCAAGCCTCTACTTGAATCC |
| HBB2M Gib 3' rev | 51 | AATGATTAACCCGCCATGCTACTTATCTACGTAAACCTAGGCTCCAGATAGCCA |

TABLE 3

Human beta globin sequencing primers

| Primer Name | SEQ ID NO: | Nucleotide Sequence |
| --- | --- | --- |
| Fwd3 seq HBB2 | 52 | GGAAGCAGAACTCTGCAC |
| Fwd4 seq HBB2 | 53 | GCATTAAGAGGTCTCTAGTTTTTTATC |
| Fwd5 seq HBB2 | 54 | GATGGTATGGGGCCAAGAGATATATC |
| Fwd6 seq HBB2 | 55 | GTCTACCCTTGGACCCAGAG |
| Fwd7 seq HBB2 | 56 | CAGTCTGCCTAGTACATTACTATTTG |
| Fwd8 seq HBB2 | 57 | CATGTTCATACCTCTTATCTTCC |
| Fwd9 seq HBB2 | 58 | GCAAACAGCTAATGCACATTGG |
| Rev3 seq HBB2 | 59 | CAGAATCCAGATGCTCAAGGCC |
| Rev4 seq HBB2 | 60 | CCCTGATTTGGTCAATATGT |
| Rev5 seq HBB2 | 61 | CATCAAGCGTCCCATAGACTCAC |
| Rev6 seq HBB2 | 62 | GCAGACTTCTCCTCAGGAGTC |
| Rev7 seq HBB2 | 63 | CTTACAGGACAGAATGGATGAAAAC |
| Rev8 seq HBB2 | 64 | GAAAAGGTCTTCTACTTGGCTC |
| Rev9 seq HBB2 | 65 | GGTTAACCAAAAGAAACTGG |

To facilitate detection of the corrected gene, a 12-bp Linker having the sequence of ACTAGTATCGAT (SEQ ID NO: 80), containing a ClaI restriction site and an SpeI restriction site, was inserted in the HBB gene. This Linker sequence was located in intron 1, 117 bp from the start codon and 97 bp from the mutation reversion site, established a strong genetic linkage between the Linker and the desired gene correction. Disruption of key donor and acceptor sites in intron 1 was avoided to maintain mRNA splicing of corrected HBB.

The hHBB-hL-014 vector was packaged into AAVHSC15 or AAVHSC17 capsid proteins using the packaging method described in Chatterjee et al., (1993) Methods 5:51-59, which is incorporated by reference herein in its entirety. The titer of the packaged virus was determined by qPCR using the primers and probes shown in Table 4.

TABLE 4

HBB correction vector qPCR primers and probe

| Primer Name | SEQ ID NO: | Nucleotide Sequence |
| --- | --- | --- |
| qHBB2M Forward Primer | 66 | TGCAGATTAGTCCAGGCAGAAA |
| qHBB2M Reverse Primer | 67 | GGGTAATCAGTGGTGTCAAATAGGA |
| qHBB2M Probe | 68 | AGTTAGATGTCCCCAGTTAA |

The AAVHSC15-hHBB-hL-014 and AAVHSC17-hHBB-hL-014 viruses were tested for their ability to edit the HBB gene in GM16265 cells using a targeted integration (TI) assay. In this assay, cells were centrifuged at 4000 RPM for 10 minutes, washed with 1×PBS, and the pellets were frozen at 80° C. for subsequent use. Frozen cell pellets were re-suspended in 200 µl for 100,000 cells. 1 µl of DNase-free RNase was added and incubated at 37° C. for 1 hour. 10 µl of 10% SDS and 1.2 µl of proteinase K was added and incubated at 56° C. overnight. High molecular weight DNA was extracted by standard phenol and chloroform extraction. For a high DNA yield, back extraction was performed with a 0.5× volume of Tris-EDTA buffer (TE) (pH 8.0) and added to the final tube. DNA was precipitated with 10M ammonium acetate at a final concentration of 2.5M. An approximately 4× volume of ice cold 100% ethanol was added. DNA was allowed to precipitate at −80° C. for at least an hour. DNA was washed with 70% ethanol, dried, re-suspended in approximately 30 to 50µ of TE, and quantified by Nanodrop. After quantification, the DNA was subject to a PCR-based "targeted integration" (TI) assay using appropriate primers to confirm the correct recombination between the hHBB-hL-014 vector and the HBB gene.

The primers having the sequences set forth in Table 5 were used for the TI assay in this Example. The HBB2MTI100 primer targeted the Linker and its neighboring region, and the HBB350 primer targeted a genomic sequence outside the homology arm. The PCR reaction would generate a 2,219 bp amplicon from DNA isolated from edited genomes, but would not substantially amplify from DNA isolated from untransduced cells or from the hHBB-hL-014 vector alone.

The PCR reaction was set up as follows: up to 50 µl of PCR water; 10 µl of 5×Q5 Buffer; 5 µl of betaine; 1 µl of 10 mM dNTPs; 1 µl of HBB2MTI100 Forward Primer (25 µM concentration); 1 µl of HBB 350 Reverse Primer (25 µM concentration); 100 ng to 1 µg of genomic DNA; 1 µl of NEB Q5 High Fidelity Polymerase. The PCR machine was set up as follows: initial denature at 95° C. for 5 minutes; 15 cycles of denature at 95° C. for 10 seconds, anneal at 70° C. for 30 seconds, decreasing 0.5 degrees every cycle, and extension at 72° C. for 2 minutes; 20 cycles of denature at 95° C. for 10 seconds; anneal at 65° C. for 30 seconds, and extension at 72° C. for 2 minutes; and a final extension at 72° C. for 5 minutes. The PCR products were analyzed by gel electrophoresis.

Amplicons of with the apparent size of 2.2 kb were isolated and blunt-end ligated into a pUC118 backbone. The resultant plasmids were analyzed by restriction digestion using ClaI or SpeI endonucleases to identify clones with correct insertion of the linker. Positive clones identified by restriction digestion were further analyzed by DNA sequencing using M13F and M13R oligonucleotide primers.

TABLE 5

Primers for HBB targeted integration assay

| Primer Name | SEQ ID NO: | Nucleotide Sequence |
|---|---|---|
| HBB2MTI100 Forward Primer (TM 54.1° C.) | 69 | CTATTGGTCTCCTTAAAATCGATACTAGT |
| HBB350 Reverse Primer (TM 54.8° C.) | 70 | ATATTCAAACTTCCGCAGAACACT |

Figure 3A:
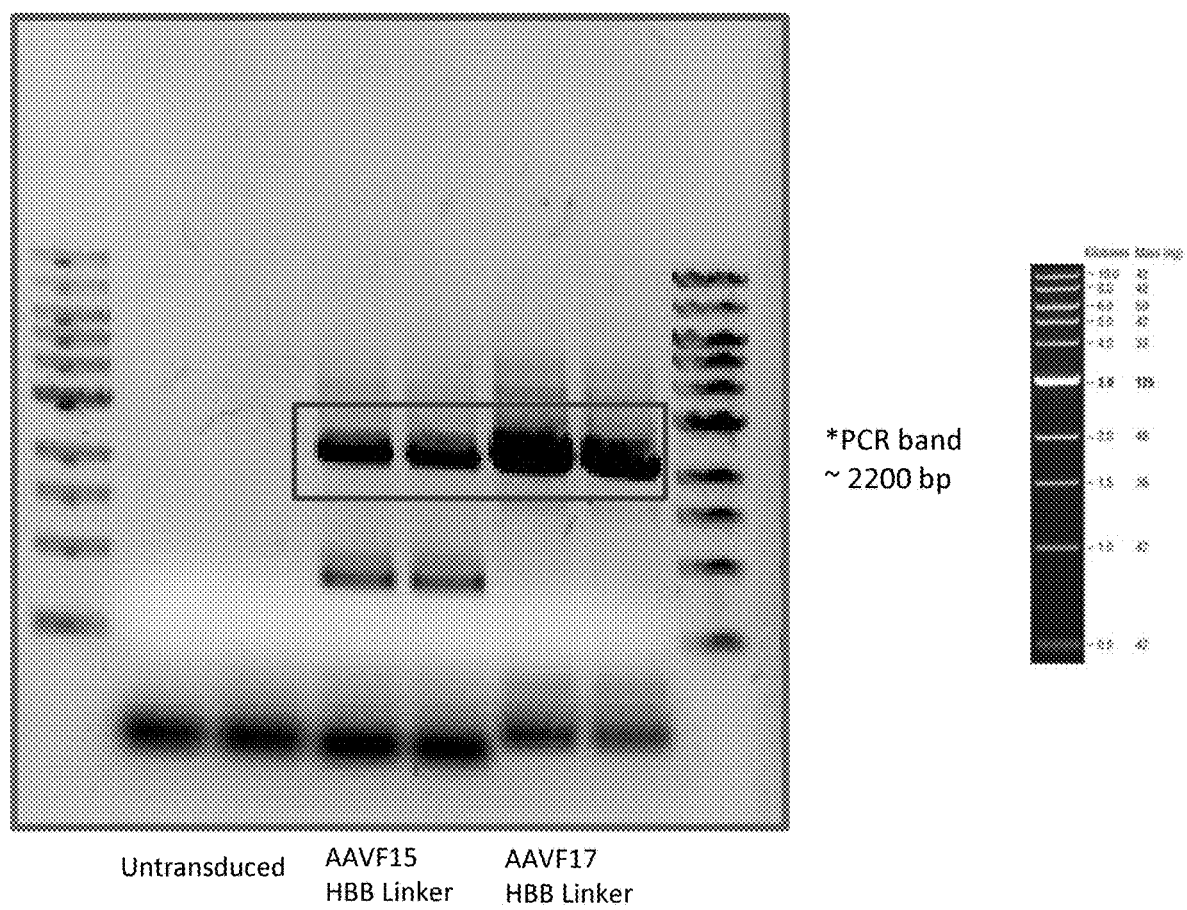
FIG. 3A is an image of DNA electrophoresis showing editing-specific size of DNA amplified from the genomic DNA of GM16265 cells transduced with the hHBB-hL-014 vector packaged in AAVHSC15 and AAVHSC17 capsids.

As shown in FIG. 3A, a 2.2 kb PCR band (indicative of correct editing by the hHBB-hL-014 vector) was detected in the TI assay in GM16265 cells transduced with AAVHSC15-hHBB-hL-014 and AAVHSC17-hHBB-hL-014 viruses, whereas this PCR product was not detected in untransduced GM16265 cells.

Correction of the A to T mutation at position 20 of the HBB gene in GM16265 cells was verified by sequencing of positive clones identified in the TI assay. Sequence analysis showed that after transduction with AAVHSC15-hHBB-hL-014 or AAVHSC17-hHBB-hL-014 virus, the T mutation was corrected to A, and asymptomatic mutations nearby were also corrected to wild-type. Sequencing of the opposite PCR strand confirmed correction of the mutations. Insertion of the linker into the HBB locus was detected in all clones. Moreover, none of the examined clones showed any undesired mutations (e.g., additional insertion, deletion, or inversion) in the genomic regions corresponding to the termini of the homology arms.

To further confirm the ability of the hHBB-hL-014 vector to edit the HBB gene, two additional LCLs, GM16266 and GM16267, were used. These LCLs were also obtained from the Coriell Institute for Medical Research (Camden, NJ), and were collected from different donors from that of GM16265. Both LCLs had the A to T mutation at position 20 in intron 1 of HBB. Following the same methods for culture and transduction of GM16265, the cells were transduced with hHBB-hL-014 packaged in an AAVHSC17 capsid.

Figure 3B:
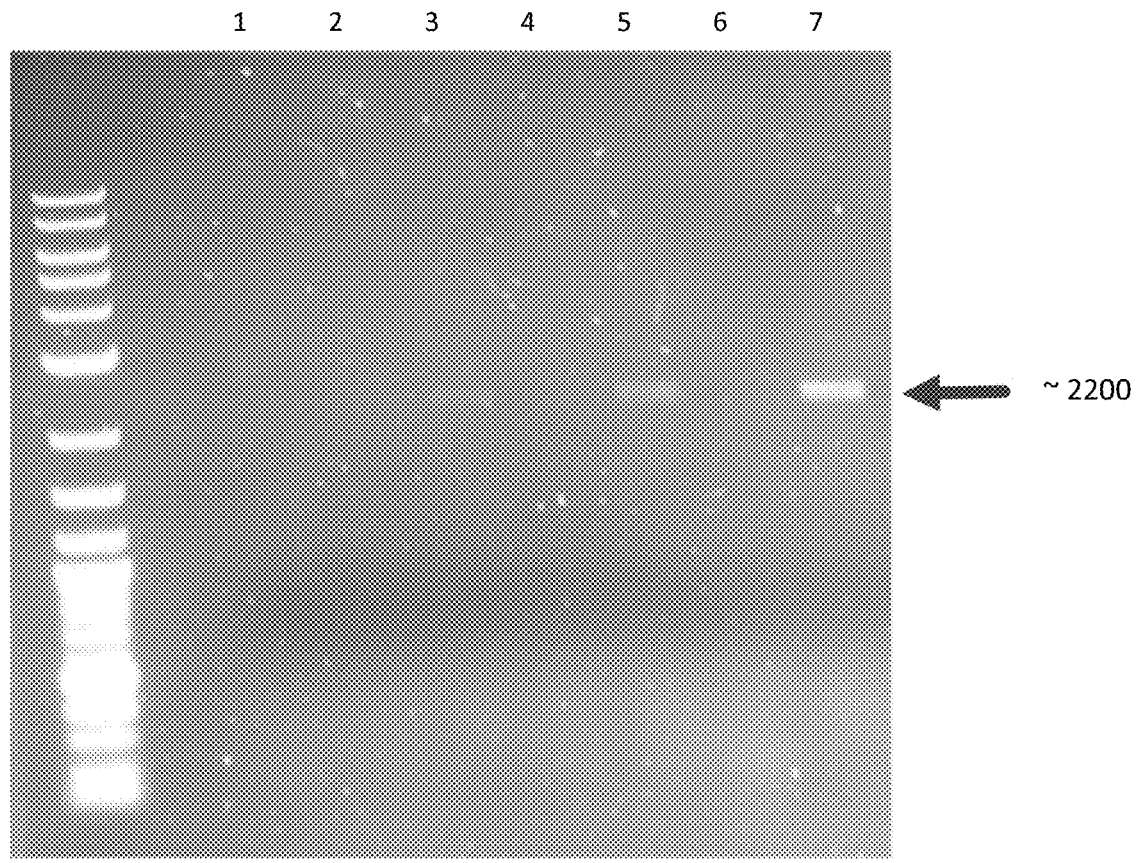
FIG. 3B is an image of DNA electrophoresis showing editing-specific size of DNA amplified from the genomic DNA of GM16265, GM16266, and GM16267 LCLs transduced with the hHBB-hL-014 vector packaged in AAVHSC17 capsid.

As shown in FIG. 3B, a PCR amplicon of about 2.2 kb was detected from cells transduced with AAVHSC17-hHBB-hL-014, but not from the untransduced cells. Sequencing results showed that the SCD mutation was corrected in the transduced cells from all three LCLs (including the GM16265 cells), and no undesired mutations (e.g., additional insertion, deletion, or inversion) were detected in the genomic regions corresponding to the termini of the homology arms. Sequencing results also confirmed appropriate linker insertion and seamless transition from the homology arm to the genome.

The above results show that the hHBB-hL-014 vector is able to revert a mutant HBB gene to the wild-type sequence in multiple SCD cell lines. Accordingly, mutations in the exons, introns, or regulatory sequences of the HBB gene in other genetic diseases, such as beta thalassemia, should also be correctable using the hHBB-hL-014 vector.

Example 3: HBB Correction Vectors Comprising a Genomic Sequence of HBB

This example provides AAV-based HBB correction vectors comprising a genomic sequence of HBB capable of correcting mutations in the HBB gene.

a) HBB Correction Vector hHBB-hL-001

Figure 4A:
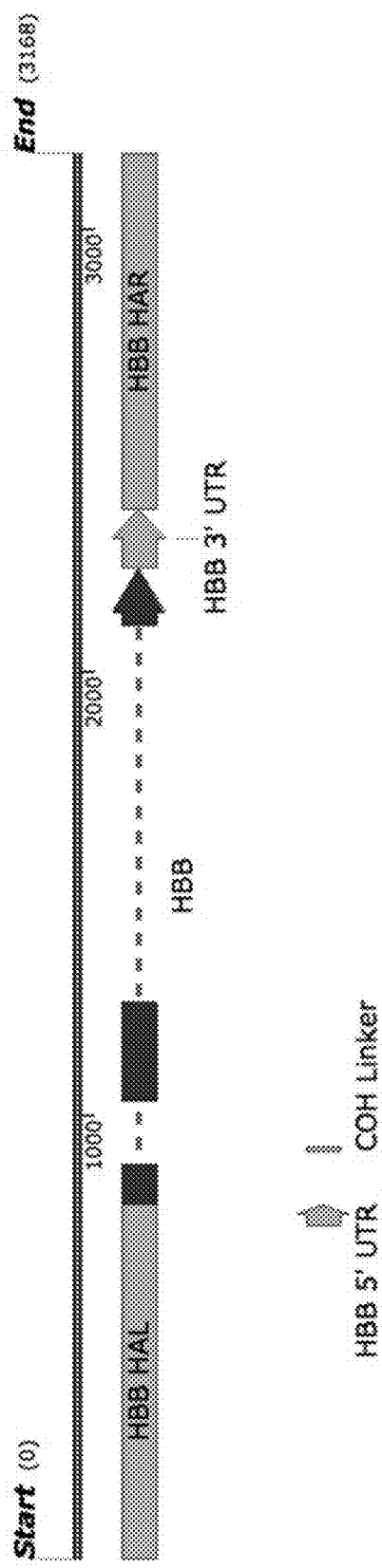

HBB correction vector hHBB-hL-001, as shown in FIG. 4A, contains HBB genomic sequence including all exons, all introns, and the polyadenylation sequence. This vector additionally contains a 5' region encompassing 800 bp upstream from the HBB transcription initiation site (referred to as "HBB HAL" in FIG. 4A), and a 3' region encompassing 800 bp downstream from the HBB polyadenylation sequence ("HBB HAR" in FIG. 4A). The hHBB-hL-001 vector comprises the nucleotide sequence set forth in SEQ ID NO: 31 (with a TI RE Linker) or SEQ ID NO:32 (without an TI RE Linker), and further comprises a 5' ITR (e.g., having the sequence of SEQ ID NO: 18) and a 3' ITR (e.g., having the sequence of SEQ ID NO: 19). This vector corrects not only mutations in the HBB exons and introns, but mutations in the 5' and 3' untranslated regions that affect HBB expression as observed in beta thalassemia.

b) HBB Correction Vector hHBB-hLW-013

Figure 4B:
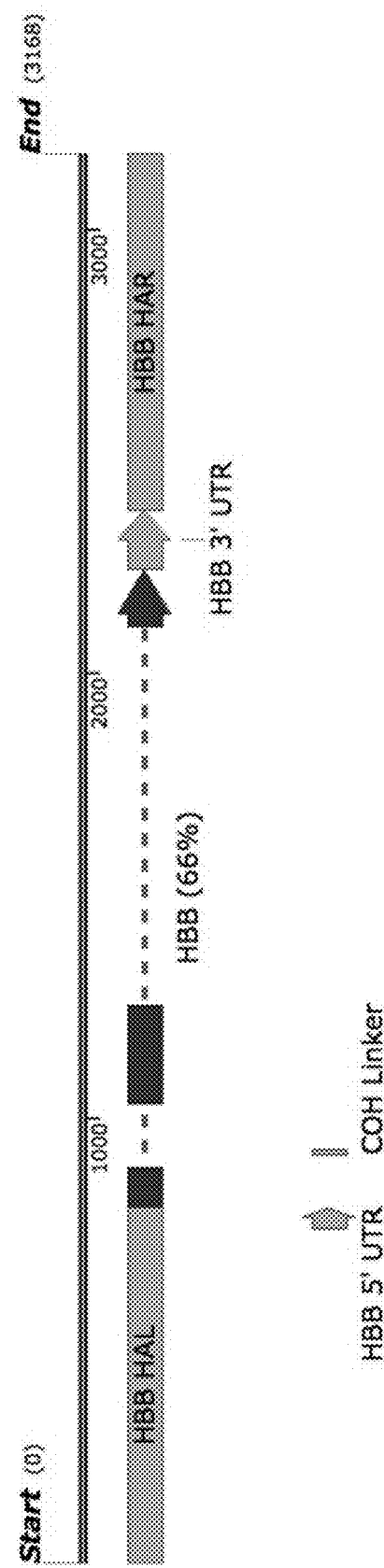

HBB correction vector hHBB-hLW-013, as shown in FIG. 4B, contains the same genetic elements as in HBB correction vector hHBB-hL-001 except that the DNA sequences of the coding regions of exons 1, 2 and 3 are silently altered to be about 67% identical, rather than fully identical, to the corresponding wild-type sequences. The reduced sequence identity results from codon alteration, wherein degenerate codons are substituted for original codons without changing the encoded amino acids. This silent codon alteration is not expected to significantly alter the expression level of HBB. Instead, it reduces the homology of HBB exons with other globin genes or pseudogenes, such as epsilon globin (HBE), delta globin (HBD), gamma globin 1 (HBG1), gamma globin 2 (HBG2), and HBB pseudogene HBBP, thereby reducing the possibility of undesired recombination of this vector at other genomic loci. In a specific example, the silently altered sequence of the coding region of exon 1, exon 2, and exon 3 are set forth in SEQ ID NOs: 43, 44 and 45, respectively. The hHBB-hLW-013 vector comprises the nucleotide sequence set forth in SEQ ID NO: 33 (with a TI RE Linker) or SEQ ID NO: 34 (without a TI RE Linker), and further comprises a 5' ITR (e.g., having the sequence of SEQ ID NO: 18) and a 3' ITR (e.g., having the sequence of SEQ ID NO: 19).

c) HBB Correction Vector hHBB-hL-011

HBB correction vector hHBB-hL-011, as shown in FIG. 4C, contains the same genetic elements as in HBB correction vector hHBB-hL-001 except that the 3' region downstream from the HBB polyadenylation sequence (referred to as "HBB HAR" in FIG. 4C) is about 100 bp in length. This modification is made to minimize inclusion of transcription promoter sequences of other genes (e.g., GATA1, MYC, etc.), which are located about 100 bp downstream from HBB polyadenylation sequence, because the promoter sequences may recruit transcriptional factors and co-factors, thereby reducing the efficiency of homologous recombination. Additionally, inclusion of transcription promoter sequences may increase aberrant expression of HBB from the vector. The hHBB-hL-011 vector comprises the nucleotide sequence set forth in SEQ ID NO: 35 (with a TI RE Linker) or SEQ ID NO: 36 (without a TI RE Linker), and further comprises a 5' ITR (e.g., having the sequence of SEQ ID NO: 18) and a 3' ITR (e.g., having the sequence of SEQ ID NO: 19).

d) HBB Correction Vector hHBB-hLW-012

HBB correction vector hHBB-hLW-012, as shown in FIG. 4D, contains the same genetic elements as in HBB correction vector hHBB-hL-011 except that the DNA sequences of the coding regions of exons 1, 2 and 3 are silently altered to be 67% identical to the corresponding wild-type sequences. In a specific example, the silently altered sequence of the coding region of exon 1, exon 2, and exon 3 are set forth in SEQ ID NOs: 43, 44 and 45, respectively. The hHBB-hLW-012 vector comprises the nucleotide sequence set forth in SEQ ID NO: 37 (with a TI RE Linker) or 38 (without a TI RE Linker), and further comprises a 5' ITR (e.g., having the sequence of SEQ ID NO: 18) and a 3' ITR (e.g., having the sequence of SEQ ID NO: 19).

Each of the four HBB correction vectors in this example contains a Linker sequence, which comprises recognition and cleavage sites for unique restriction endonucleases, to facilitate detection of the corrected gene. This Linker sequence is located in intron 1, 117 bp from the start codon. Disruption of key donor and acceptor sites in intron 1 is avoided to maintain mRNA splicing of corrected HBB.

Figure 5A:
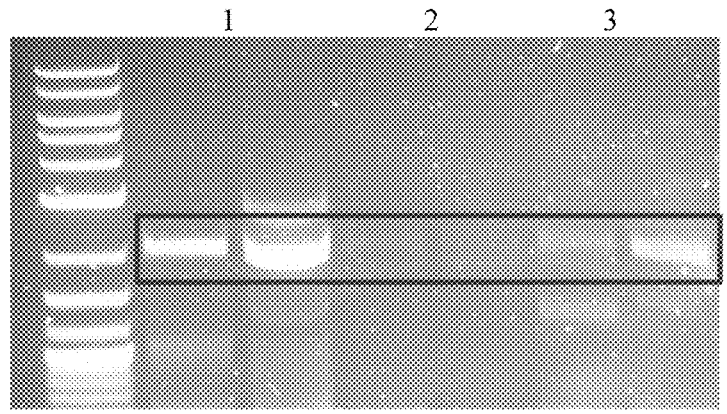
FIGS. 5A, 5B, and 5C are images of DNA electrophoresis showing editing-specific size of DNA amplified from the genomic DNA of primary human CD34+ HSCs transduced with the vectors indicated in the figures packaged in AAVHSC17 capsid.
Figure 5B:
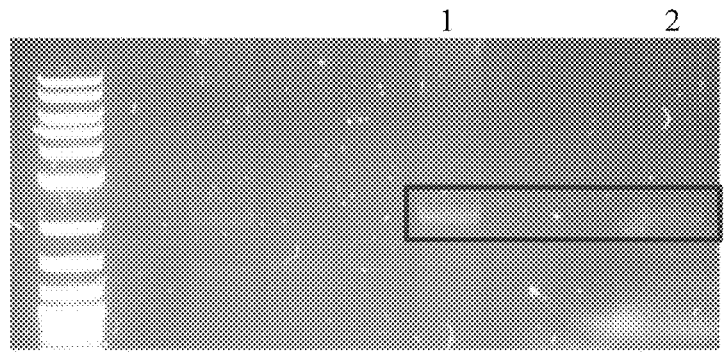
Figure 5C:
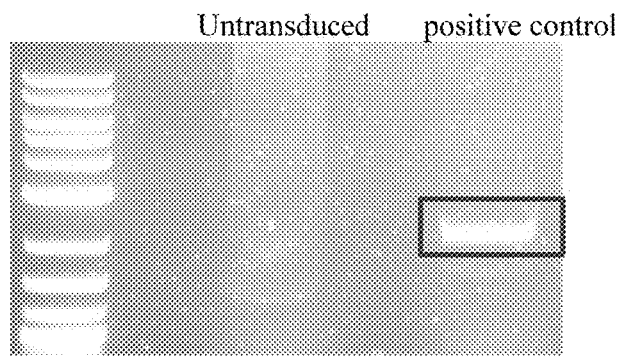

Each of the four HBB correction vectors described above was generated and packaged in AAVHSC17. Primary human CD34+ HSCs were transduced with the viruses using the method as described in Example 1, and integration was assessed by the TI assay as described in Example 2. As shown in FIGS. 5A and 5B, hHBB-hL-001, hHBB-hL-011, and hHBB-hLW-012 were all capable of editing the HBB gene.

The efficiency of genome editing was measured quantitatively by next-generation sequencing (NGS). PCR reactions were performed using primers specific to a region of the genome outside the homology arms, as shown in Table 6. These primers will amplify a product of 2,342 bp from unedited and edited alleles, but will not amplify the AAV vector.

TABLE 6

Primers for NGS sample preparation

| Primer Name | SEQ ID NO: | Nucleotide Sequence |
|---|---|---|
| HBB350 Reverse Primer | 70 | ATATTCAAACTTCCGCAGAACACT |
| HBB L NGS S1 | 81 | CCTCTGGGTCCAAGGGTAGA |

The PCR reaction was set up as follows: up to 50 µl of PCR water; 10 µl of 5×Q5 Buffer; 5 µl of Betaine; 1 µl of 10 mM dNTPs; 1 µl of HBB350 Reverse Primer (25 µM); 1 µl of HBB L NGS S1 primer (25 µM); 200 ng of genomic DNA; and 1 µl of Q5 Hifidelity Polymerase. The PCR machine was set up as follows: initial denature at 98° C. for 30 minutes; 30 cycles of denature at 95° C. for 10 seconds, anneal at 65° C. for 30 seconds, and extension at 72° C. for 2 minutes; and a final extension at 72° C. for 5 minutes.

The PCR product of the correct size was isolated by gel electrophoresis, and was extracted using Qiagen Qiaquick Gel Extraction Kit according to standard protocol. The absence of vector genomes in the gel extracted amplicons was confirmed by PCR using vector specific primers and a known number of vector specific genome template as positive control. To confirm absence of vector genomes, the following PCR conditions were used: initial denature at 98° C. for 30 minutes; 30 cycles of denature at 98° C. for 10 seconds, anneal at 66° C. for 30 seconds, and extension at 72° C. for 1 minute; and a final extension at 72° C. for 2 minutes. The forward primer used was AAAGTCAGGGCAGAGCCATC (SEQ ID NO: 108) and the reverse primer used was AATGATTAACCCGCCATGCT (SEQ ID NO: 109), and will amplify an amplicon of 1,797 base pairs.

The extracted PCR product was used for NGS sequencing, and/or digital PCR quantitation as described below. In the case of NGS sequencing, the extracted PCR product was subjected to a nested round of PCR using the primers shown in Table 7. Each sample had a unique combination of forward and reverse primers, and the size of each correct PCR product was about 388 bp. The PCR machine was set up as follows: initial denature at 98° C. for 30 minutes; 30 cycles of denature at 98° C. for 10 seconds, anneal at 72° C. for 30 seconds, and extension at 72° C. for 30 seconds; and a final extension at 72° C. for 2 minutes.

TABLE 7

Primers for NGS sample preparation

| Primer Name | SEQ ID NO: | Nucleotide Sequence |
|---|---|---|
| HBB NGS Nest 5 Forward Adapter 1 | 82 | AATGATACGGCGACCACCGAGATCTACACAAGTAGA GTCTTTCCCTACACGACGCTCTTCCGATCTGGGCATA AAAGTCAGGGCAGA |

TABLE 7-continued

Primers for NGS sample preparation

| Primer Name | SEQ ID NO: | Nucleotide Sequence |
|---|---|---|
| HBB NGS Nest 5 Forward Adapter 2 | 83 | AATGATACGGCGACCACCGAGATCTACACCATGCTTA TCTTTCCCTACACGACGCTCTTCCGATCTtGGGCATAA AAGTCAGGGCAGA |
| HBB NGS Nest 5 Forward Adapter 3 | 84 | AATGATACGGCGACCACCGAGATCTACACGCACATCT TCTTTCCCTACACGACGCTCTTCCGATCTatGGGCATA AAAGTCAGGGCAGA |
| HBB NGS Nest 5 Forward Adapter 4 | 85 | AATGATACGGCGACCACCGAGATCTACACTGCTCGAC TCTTTCCCTACACGACGCTCTTCCGATCTgatGGGCATA AAAGTCAGGGCAGA |
| HBB NGS Nest 5 Reverse Adapter 1 | 86 | CAAGCAGAAGACGGCATACGAGATCATGATCGGTGA CTGGAGTTCAGACGTGTGCTCTTCCGATCTGTCTCCA CATGCCCAGTTTCTA |
| HBB NGS Nest 5 Reverse Adapter 2 | 87 | CAAGCAGAAGACGGCATACGAGATAGGATCTAGTGA CTGGAGTTCAGACGTGTGCTCTTCCGATCTtGTCTCCA CATGCCCAGTTTCTA |
| HBB NGS Nest 5 Reverse Adapter 3 | 88 | CAAGCAGAAGACGGCATACGAGATGACAGTAAGTGA CTGGAGTTCAGACGTGTGCTCTTCCGATCTatGTCTCC ACATGCCCAGTTTCTA |
| HBB NGS Nest 5 Reverse Adapter 4 | 89 | CAAGCAGAAGACGGCATACGAGATCCTATGCCGTGA CTGGAGTTCAGACGTGTGCTCTTCCGATCTgaGTCTCC ACATGCCCAGTTTCTA |

Amplicon sizes were confirmed by gel electrophoresis, and the PCR products were purified using Qiagen Qiaquick PCR Purification Kit according to standard protocol. Amplicons from all tested samples were mixed at equal molarities, and the concentration was confirmed by an Advanced Analytical bioanalyzer. The samples were sequenced using a MiSeq V2 300 cycle kit.

Table 8 shows the number of acceptable reads with and without the linker sequence present as well as the number of reads with HBB sequences, as determined from the NGS analysis. Because the presence of the linker sequence indicated AAV vector integration, the percentages of alleles with linker represented the allelic frequencies of integration of these vectors, which are generally between 0.1% and 1%.

TABLE 8

Allelic frequency of integration of HBB correction vectors

| Sample | # linkers | # no linkers | #linker adjacent sequence | % with linker | % reads captured* |
|---|---|---|---|---|---|
| HBB-hL-014 #1 | 4 | 2703 | 2710 | 0.14 | 99.88 |
| HBB-hL-011 #1 | 3101 | 475533 | 479142 | 0.64 | 99.89 |
| HBB-hL-011 #2 | 5 | 1917 | 1925 | 0.26 | 99.84 |
| HBB-hL-001 #1 | 3 | 449 | 455 | 0.66 | 99.34 |
| HBB-hL-011 #3 | 2 | 235 | 235 | 0.84 | 100.85 |
| Negative control | 0 | 1 | 1 | 0 | 1 |
| Untransduced | 0 | 0 | 0 | 0 | 0 |

*% reads captured is a quality control metric that indicates the percentage quality passing reads containing the sequence adjacent to the linker sequence divided by the sum on the reads containing the linker sequence and no linker sequence.

In the case of digital PCR, the extracted PCR product was subjected to digital PCR analysis using the BioRad QX200™ Droplet Digital™ PCR System. Editing was determined by calculating the linkage between the genomic target and the inserted vector payload (linker) and was measured by detecting the amount of partitioned droplets that contain both the vector and the genome in relation to expectation of coincidence by chance employing the methods used for genetic linkage between variants (see, e.g., Regan et al., A rapid molecular approach for chromosomal phasing, PLoS One. (2015) 10(3):e0118270, incorporated herein by reference in its entirety). A concentration of 0.1 ng/ul of genomic DNA was analyzed across a minimum of three experiments per sample for linkage and measured using multiplexed ddPCR with a vector specific probe set and a genomic specific probe set. The primer and probe set is as follows:

TABLE 9

Primer and probe set used for digital PCR

| | SEQ ID NO: | Nucleotide sequence |
|---|---|---|
| Linker specific primer and probe set | | |
| HBB Probe | 110 | AACTGGGCATGTGGAGACAGAGAA |
| HBB Linker F | 111 | GTTACAAGACAGGACTAGTATCGAT |
| HBB R | 112 | TAGACCAATAGGCAGAGAGAGT |
| Genomer specific primer and probe set | | |
| HBB0101GDNA F | 113 | CTGAGCCAAGTAGAAGACCTTT |
| HBB0101GDNA R | 114 | CTGTTTCTGCCTGGACTAATCT |
| HBB0101GDNA Probe | 115 | CCCTACTTTCTAAGTCACAGAGGCT |

In order to measure genome editing/linkage as per the method above against a known quantity of edited material, a standard DNA series was created. The standard consisted of 100 unedited genomes per ul, 1000 episomal vector per ul and a range of cloned positive alleles at 1 per ul, 5 per ul, 10 per ul, 15 per ul, 20 per ul, and 25 edited alleles per ul, respectively. The amount of genetic linkage in each sample was measured and plotted against the known ratio of unedited to edited allele in each sample (R2=0.972, pearson correlation p<0.001).

Figure 6:
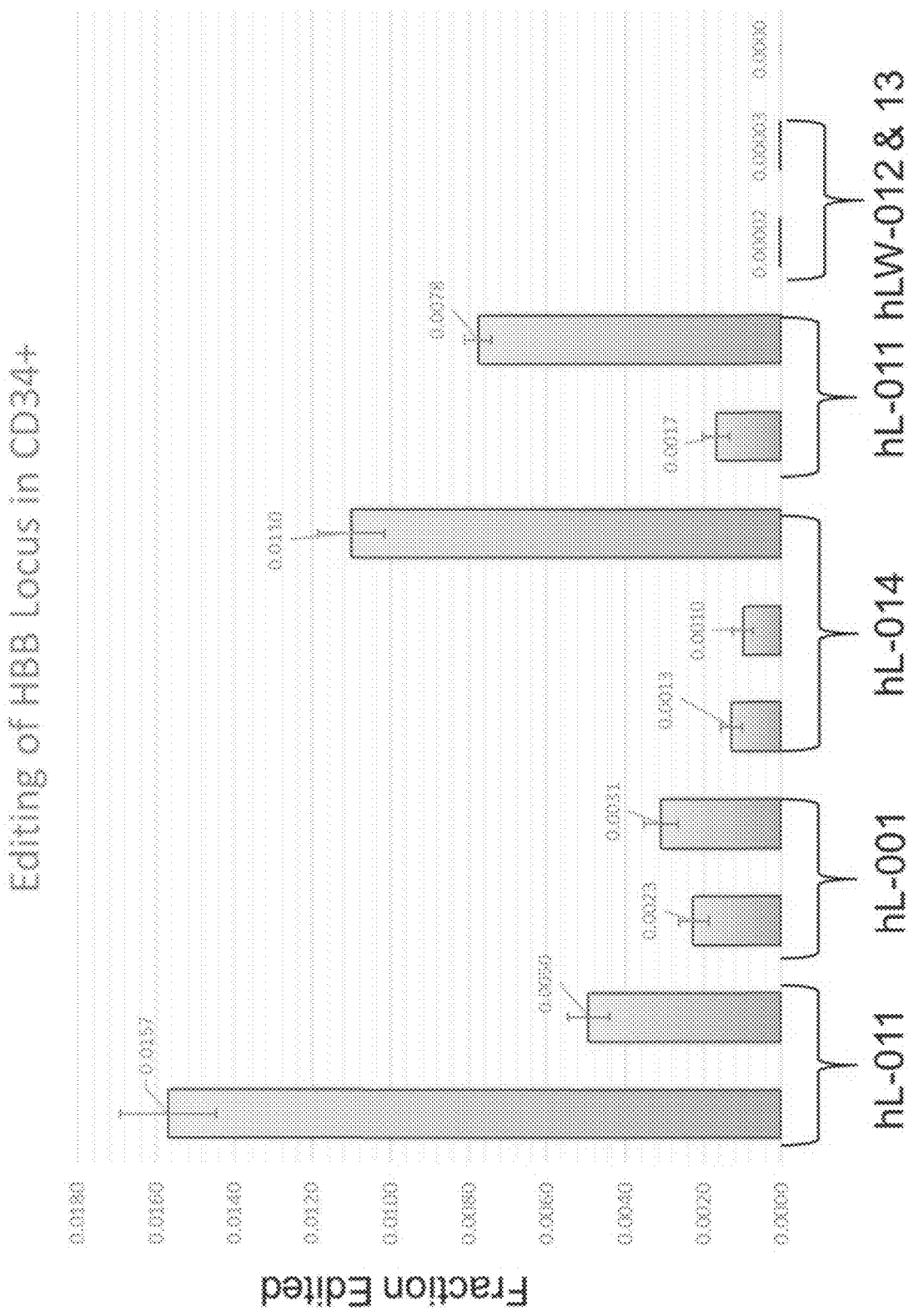
FIG. 6 is a graph showing the fraction of edited CD34+ cells across samples as indicated.

Editing of the HBB locus in primary CD34+ mixed cord blood cells transduced with various AAVHSC7 HBB editing vectors at a MOI of 1.5×10$^5$ were measured by digital PCR. Cells were harvested at 48 hours post-transduction and assayed for percentage of alleles edited by an out/out PCR and digital PCR analysis of PCR products. FIG. 6 shows the fraction of edited loci across the samples as indicated.

Example 4: HBB Correction Vectors Comprising an HBB Coding Sequence or a Portion Thereof This example provides HBB correction vectors that are capable of inserting an HBB coding sequence or a portion thereof into the HBB gene, e.g., after the start codon or into intron 1. The inserted sequence can be transcribed and translated from the native locus under the control of the native transcription regulatory elements, thereby restoring the expression of a functional HBB protein.

Each of the HBB correction vectors contained an HBB coding sequence or a portion thereof from the second codon to the stop codon. The HBB coding sequence or portion thereof is followed by an SV40 polyadenylation sequence, which is strong enough to support proper expression and significantly reduce further transcription of the rest of the endogenous HBB gene. A targeted integration restriction cassette ("TI RE cassette") comprising recognition and cleavage sites for a unique restriction endonuclease is optionally inserted downstream from the polyadenylation sequence, facilitating detection of the desired homologous recombination.

a) HBB Correction Vector hHBB-hA-009

Figure 7A:
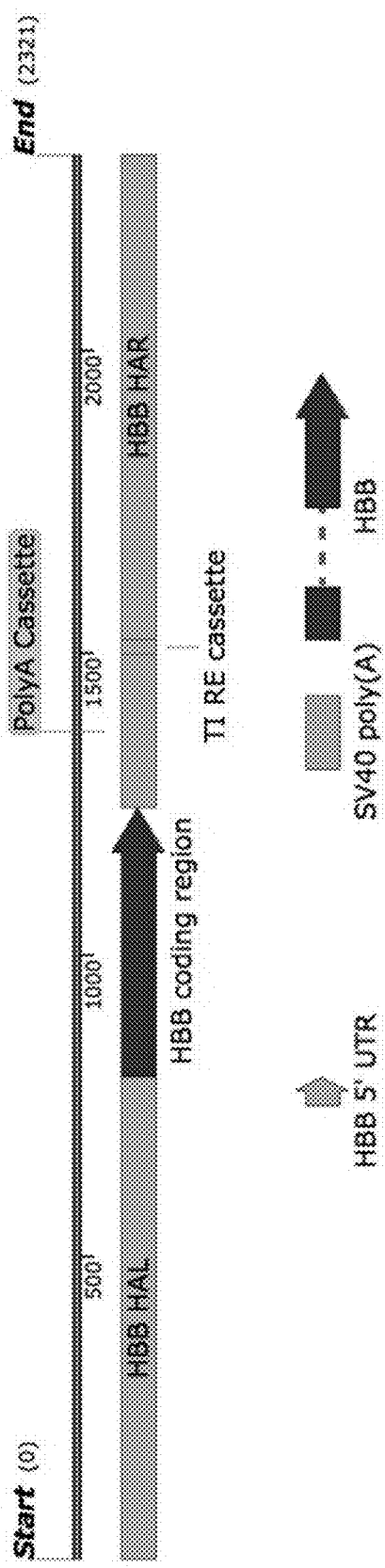
FIGS. 7A, 7B, 7C, 7D, and 7E are vector maps showing the genetic elements between the two AAV ITRs of HBB correction vectors hHBB-hA-009, hHBB-hAW-002, hHBB-h1-010, hHBB-h1W-008, and hHBB-hE3C-001, respectively.

HBB correction vector hHBB-hA-009, as shown in FIG. 7A, contains a portion of a wild-type HBB coding sequence from the second codon to the stop codon (nucleotides 4-444 of SEQ ID NO: 27), followed by an SV40 polyadenylation sequence as described above. The vector further contains a 5' homology arm (referred to as "HBB HAL" in FIG. 7A) comprising the wild-type genomic sequence upstream from and including the HBB start codon, and a 3' homology arm (referred to as "HBB HAR" in FIG. 7A) comprising the wild-type genomic sequence downstream from but not including the HBB start codon. Each of the 5' homology arm and the 3' homology arm is about 800 bp in length. The hHBB-hA-009 vector comprises the nucleotide sequence set forth in SEQ ID NO: 39, and further comprises a 5' ITR (e.g., having the sequence of SEQ ID NO: 18) and a 3' ITR (e.g., having the sequence of SEQ ID NO: 19). The 5' homology arm has the ability to correct mutations in the start codon and/or 5' untranslated region (UTR) that affect HBB expression as observed in some beta thalassemia patients. As a result, the integration of HBB correction vector hHBB-hA-009 can restore the expression of wild-type HBB that has been impaired by mutations in 5' UTR, coding sequence, or 3' UTR.

b) HBB Correction Vector hHBB-hAW-002

Figure 7B:
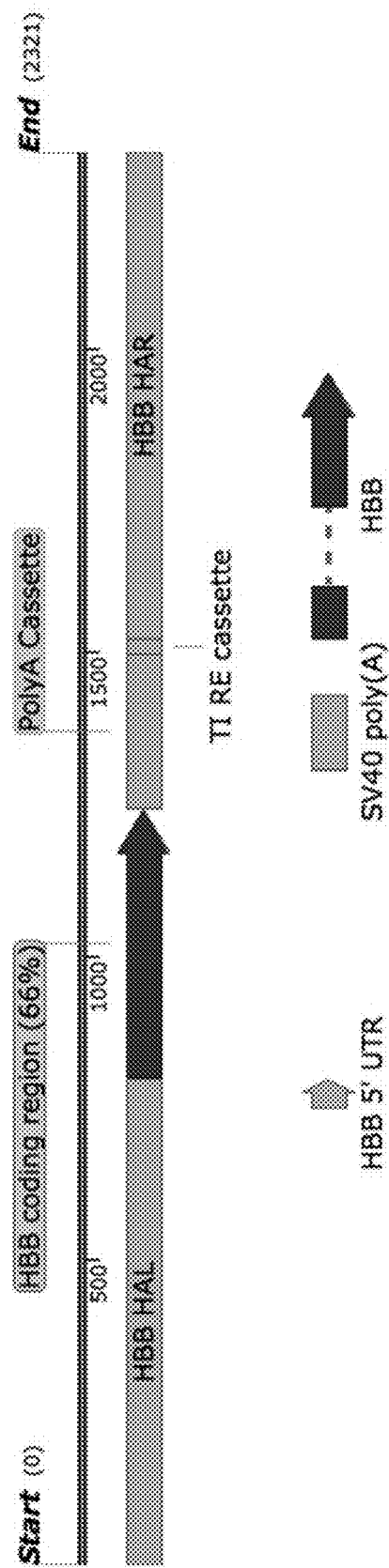

HBB correction vector hHBB-hAW-002, as shown in FIG. 7B, contains the same genetic elements as in HBB correction vector hHBB-hA-009, except that the portion of HBB coding sequence is silently altered to SEQ ID NO: 47, 67% identical to the corresponding region of wild-type cDNA sequence. As described in Example 3, this codon alteration is not expected to significantly alter the expression level of HBB. Instead, it reduces the homology of HBB exons with other globin genes and pseudogenes, thereby reducing undesired recombination of this vector at other genomic loci. The hHBB-hAW-002 vector comprises the nucleotide sequence set forth in SEQ ID NO: 40, and further comprises a 5' ITR (e.g., having the sequence of SEQ ID NO: 18) and a 3' ITR (e.g., having the sequence of SEQ ID NO: 19).

c) HBB Correction Vector hHBB-h1-010

Figure 7C:
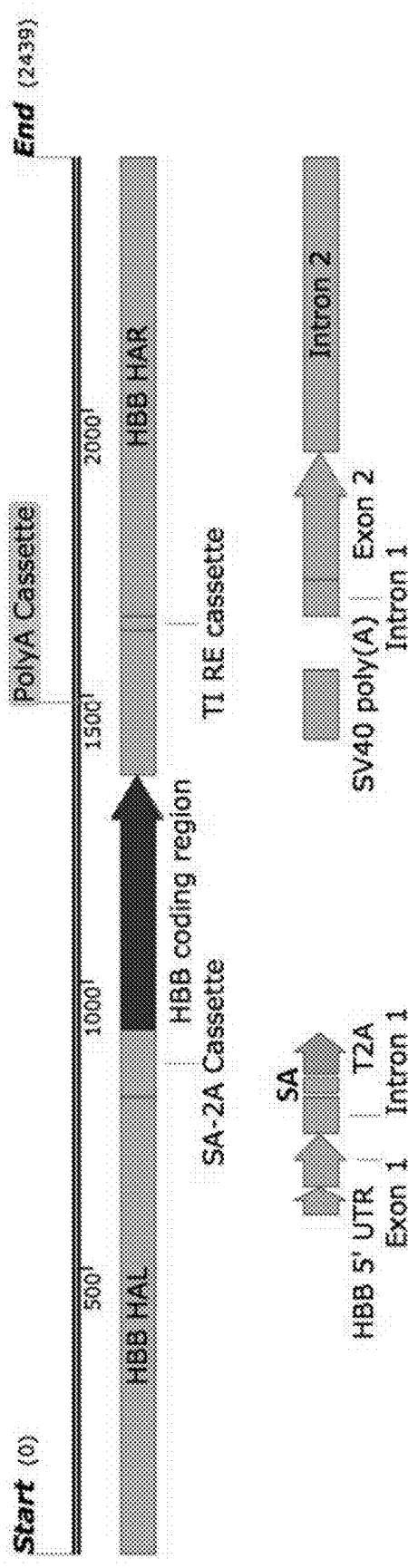

HBB correction vector hHBB-h1-010, as shown in FIG. 7C, is designed to insert a wild-type HBB coding sequence into intron 1 by homologous recombination. Specifically, the insertion site is between nucleotides 160 and 161 of the HBB gene, and the insertion avoids disruption of key splice donor sites in intron 1. The editing element (inserted region) of this vector contains from 5' to 3' a splice acceptor site ("SA" in FIG. 7C, e.g., SEQ ID NO: 14), a ribosomal skipping element ("T2A" in FIG. 7C, e.g., SEQ ID NO: 72) in-frame with the HBB start codon upon integration, a wild-type HBB coding sequence (SEQ ID NO: 27), and an SV40 polyadenylation sequence. Upon integration, the pre-mRNA transcribed from the HBB locus contains from 5' to 3': exon 1 of endogenous HBB; the first 68 nucleotides of intron 1, including the endogenous splice donor at the 5' end of intron 1; the splice acceptor introduced by the hHBB-h1-010 vector; the ribosomal skipping element; the HBB coding sequence; and a poly(A) tail. After splicing, the mRNA contains from 5' to 3': exon 1 of endogenous HBB; the in-frame ribosomal skipping element; the HBB coding sequence; and a poly(A) tail. The ribosomal skipping element leads to generation of two polypeptides: a truncated HBB peptide terminated at the end of exon 1 fused with a partial ribosomal skipping peptide, and a proline from the ribosomal skipping peptide fused to the N-terminus of a full-length HBB polypeptide.

The hHBB-h1-010 vector further comprises a 5' homology arm (referred to as "HBB HAL" in FIG. 7C) comprising the wild-type genomic sequence upstream from the insertion site, and a 3' homology arm (referred to as "HBB HAR" in FIG. 7C) comprising the wild-type genomic sequence downstream from the insertion site. Each of the 5' homology arm and the 3' homology arm is about 800 bp in length. The hHBB-h1-010 vector comprises the nucleotide sequence set forth in SEQ ID NO: 41, and further comprises a 5' ITR (e.g., having the sequence of SEQ ID NO: 18) and a 3' ITR (e.g., having the sequence of SEQ ID NO: 19). The 5' homology arm has the ability to correct mutations in the 5' UTR that affect HBB expression as observed in some beta thalassemia patients, and restore expression of wild-type HBB that has been impaired by mutations in 5' UTR, coding sequence, or 3' UTR.

d) HBB Correction Vector hHBB-h1W-008

Figure 7D:
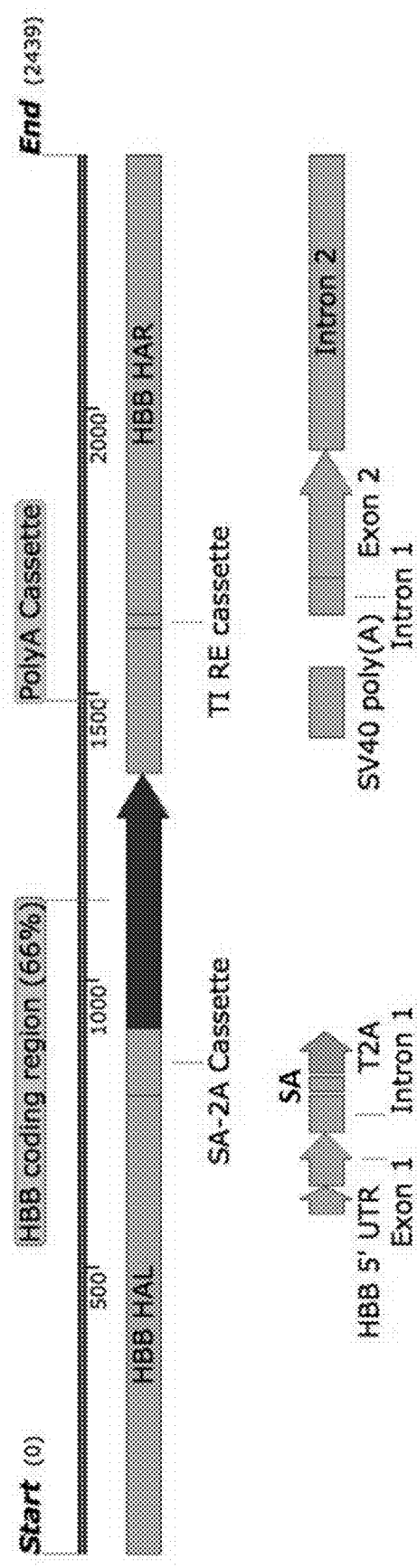

HBB correction vector hHBB-h1W-008, as shown in FIG. 7D, contains the same genetic elements as in HBB correction vector hHBB-h1-010, except that the HBB coding sequence is silently altered to be 67% identical to the corresponding region of wild-type cDNA sequence. As described in Example 3, this sequence modification is not expected to significantly alter the expression level of HBB. Instead, it reduces the homology of HBB exons with other globin genes and pseudogenes, thereby reducing undesired of this vector to other genomic loci. In a specific example, the silently altered HBB coding sequence is set forth in SEQ ID NO: 47. The hHBB-h1W-008 vector comprises the nucleotide sequence set forth in SEQ ID NO: 42, and further comprises a 5' ITR (e.g., having the sequence of SEQ ID NO: 18) and a 3' ITR (e.g., having the sequence of SEQ ID NO: 19).

e) HBB Correction Vector hHBB-hE3C-001

Figure 7E:
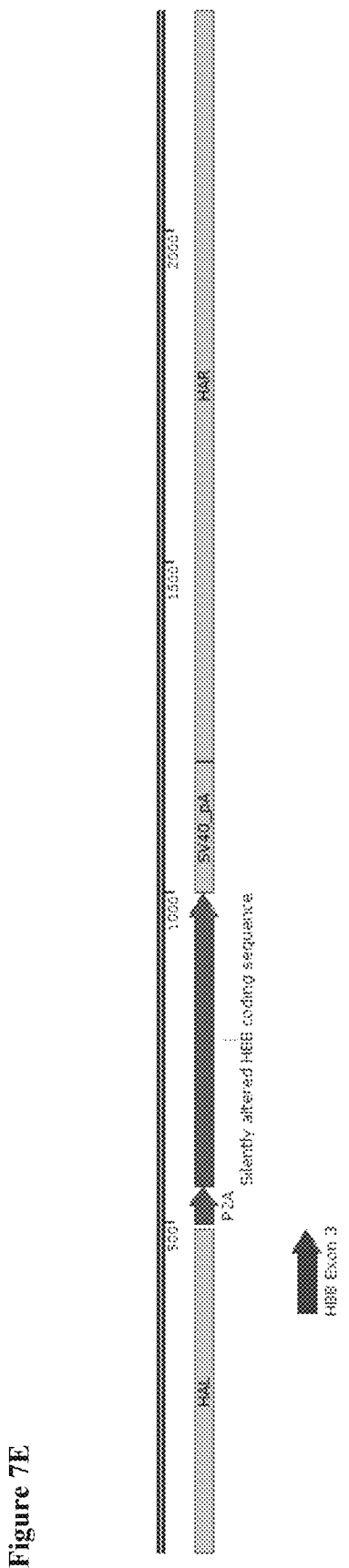

HBB correction vector hHBB-hE3C-001, as shown in FIG. 7E, is designed to insert an HBB coding sequence into exon 3 of the HBB gene, directly after the stop codon, by homologous recombination. The editing element (inserted region) of this vector contains from 5' to 3' a ribosomal skipping element ("P2A" in FIG. 7E, e.g., SEQ ID NO: 74) in frame with a silently altered HBB coding sequence (SEQ ID NO: 99, 85% identical to the wild-type HBB coding sequence), and an SV40 polyadenylation sequence (SEQ ID NO: 77). The silent alteration of the HBB coding sequence is designed to increase the level of protein expressed from the coding sequence, remove low-complexity sequences that could lead to off-targeting of the vector to undesired genomic loci, and/or reduce the homology between the editing element and the genome, thereby reducing undesired integration mediated by the editing element rather than by a homology arm.

Upon integration, the mRNA transcribed from the HBB locus contains from 5' to 3': a portion of the native HBB mRNA adjacently 5' to the stop codon, the ribosomal skipping element, the silently altered HBB coding sequence, and the SV40 polyadenylation sequence. The ribosomal skipping element leads to generation of two polypeptides: a native full-length HBB peptide fused with an N-terminal part of the ribosomal skipping peptide, and a proline residue from the ribosomal skipping peptide fused to the N-terminus of a full-length wild-type HBB polypeptide.

The hHBB-hE3C-001 vector further comprises a 5' homology arm (referred to as "HAL" in FIG. 7E) comprising the sequence of SEQ ID NO: 101, a wild-type genomic sequence upstream from the insertion site, and a 3' homology arm (referred to as "HAR" in FIG. 7E) comprising the sequence of SEQ ID NO: 102, a wild-type genomic sequence downstream from the insertion site.

The nucleotide sequence of hHBB-hE3C-001 is set forth in SEQ ID NO: 104. The vector further comprises a 5' ITR (e.g., having the sequence of SEQ ID NO: 18) and a 3' ITR (e.g., having the sequence of SEQ ID NO: 19).

The integration efficiency of hHBB-h1-010 and hHBB-h1W-008 was assessed in RKO and LCL cells. GM16265 LCL cells were transduced with HBB correction vectors packaged in AAVHSC7 using the method described in Example 1.

RKO cells were obtained from ATCC. The cells were cultured in DMEM supplemented with 10% FCS and 2 mM L-glutamine. They were plated at a density of 750,000 cells per well in a 6 well plate. The cells were transfected using the following method: 24 hours after plating, the cells were transfected in OptiMEM media by adding a transfection mixture, which was prepared by mixing and incubating (a) 2 µg of HBB editing plasmid diluted in 250 µl OptiMEM and (b) 5 µl Lipofectamine 2000 diluted in 250 µl OptiMEM for 15 minutes. The cells were harvested 24 hours after the transfection.

Integration was assessed by a TI assay using the primers having the sequences set forth in Table 9. The SA-2A-FM1 and SA-2A-FM2 primers were specific to the splice acceptor and T2A element inserted into the genome by the hHBB-h1-010 or hHBB-h1W-008 vector, and the HBB-Out-RM2 primer was specific to a region of the genome downstream from the 3' homology arm. The primer pairs of HBB-Out-RM2 with SA-2A-FM1 or SA-2A-FM2 do not amplify a product in untransduced cells or a product from the correction vector alone. PCR reaction using SA-2A-FM1 and HBB-Out-RM2 would generate a 1,881 bp amplicon if the hHBB-h1-010 or hHBB-h1W-008 vector is integrated by homologous recombination through the 5' and 3' homology arms, and would generate a 1,188 bp amplicon if the vector is integrated by homologous recombination through the 5' homology arm and the exon 2 sequence in the editing element. PCR reaction using SA-2A-FM2 and HBB-Out-RM2 would also generate different sizes of amplicon from these two manners of integration.

The PCR reaction was set up as follows: up to 50 µl of PCR water; 5 µl of 10×PCR Buffer; 1 µl of 10 mM dNTPs; 1 µl of 50 mM $MgCl_2$; 10 µl of 5×Q Reagent; 2.5 µl of TI Forward Primer (5 µM concentration); 2.5 µl of TI Reverse Primer (5 µM concentration); 100 ng genomic DNA; and 0.5 µl of HotStarTaq Polymerase. The PCR machine was set up as follows: initial denature at 95° C. for 15 minutes; 40 cycles of denature at 94° C. for 10 seconds, anneal at 58° C. for 30 seconds, and extension at 72° C. for 3 minutes; and a final extension at 68° C. for 10 minutes. The PCR products were analyzed by gel electrophoresis.

TABLE 9

Primers for HBB targeted integration assay

| Primer Name | SEQ ID NO: | Nucleotide Sequence |
| --- | --- | --- |
| SA-2A-FM1 | 96 | GCTTCTGACCTCTTCTCTTCCTCCC |
| SA-2A-FM2 | 97 | GCGGTGACGTGGAGGAGAATC |
| HBB-Out-RM2 | 98 | GCAGAATGGTAGCTGGATTGTAGC |

Figure 8:
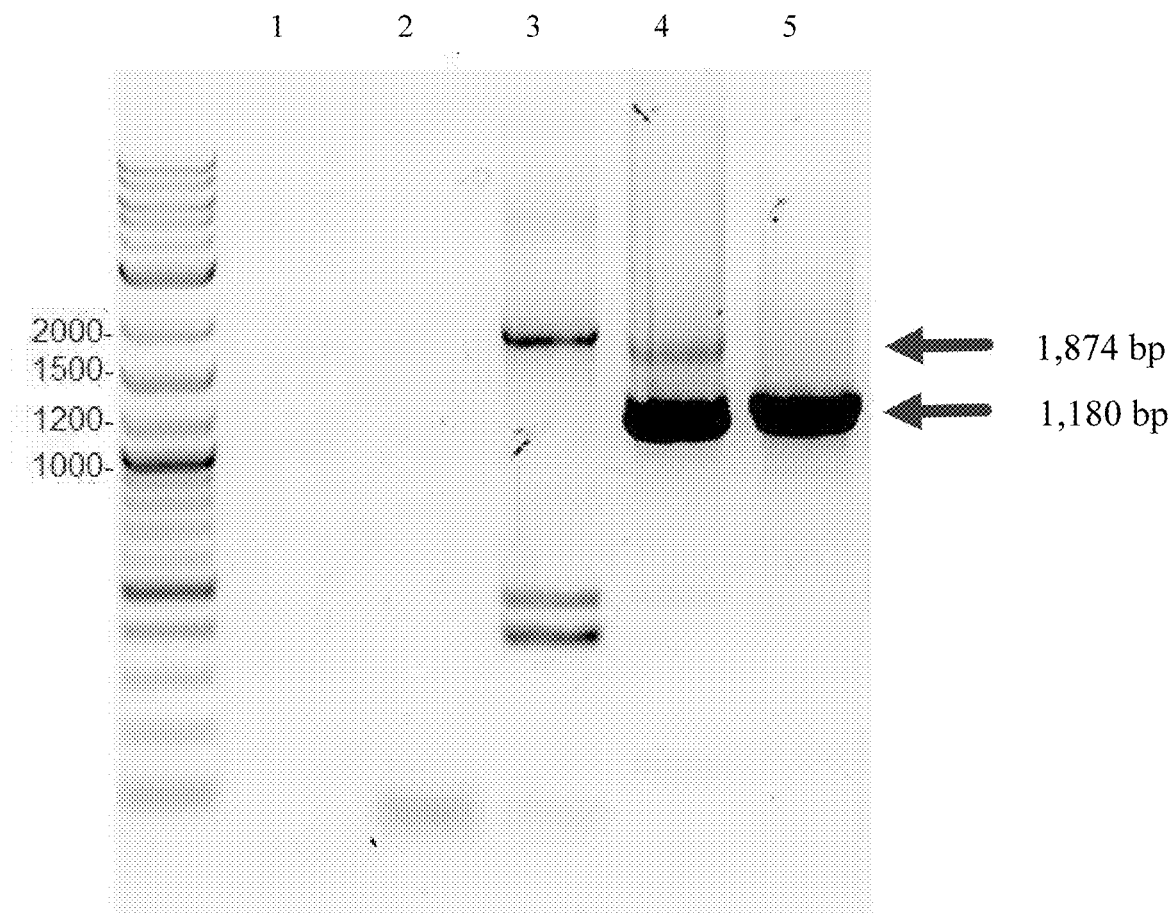
FIG. 8 is an image of DNA electrophoresis showing editing-specific size (1,874 bp) and non-specific size (1,180 bp) of DNA amplified from genomic DNA of RKO and GM16265 LCL cells transduced with the vectors indicated in the figures packaged in AAVHSC7 capsid.

As shown in FIG. 8, using the SA-2A-FM1 and HBB-Out-RM2 primers, targeted integration PCR product having a length of 1,874 nucleotides was detected in RKO cells transduced with hHBB-h1W-002, indicating successful integration of the vector in the desired manner. By contrast, a shortened PCR product, generated by recombination of exon 2 in the editing element (rather than in the 3' homology arm) with the HBB locus, was detected in RKO and LCL cells transduced with hHBB-h1-010. Similar results were obtained from PCR using the SA-2A-FM2 and HBB-Out-RM2 primers. This result indicates that silent codon alteration in the editing element reduces or eliminates undesired recombination, thereby assuring accurate editing of the HBB gene.

Example 5: In Vivo Correction of HBB Mutations

This example provides an animal model for examining HBB correction vectors, such as those described in the previous examples. An NSG mouse having the genotype of NOD.Cg-Prkdc$^{scid}$ Il2rg$^{tm1Wjl}$/SzJ was sublethally irradiated and underwent hematopoietic reconstitution by transplantation with primary human wild-type CD34$^+$ HSCs. Engraftment levels of human CD34$^+$ HSCs in the NSG mice were determined 12 weeks after transplantation by assaying peripheral blood for the presence of human and murine CD45$^+$ cells by flow cytometry. Mice having greater than 25% circulating human cells in the peripheral blood were used for assessing the integration efficiency of specific AAV vectors to transduce primary human CD34$^+$ HSCs in vivo.

The AAVS1-FP vector was packaged in AAVHSC7 and AAVHSC17, and the viral particles were administered to the reconstituted NSG mice intravenously at a dose between 1.22×10$^{13}$ and 1.54×10$^{13}$ vector genomes per kg. Blood, bone marrow, and spleen samples were collected 4 weeks after the administration. DNA was purified from the samples by the phenol/chloroform extraction method known in the art, and the extracted DNA was analyzed by ddPCR using the method as described in Example 1.

Figure 9:
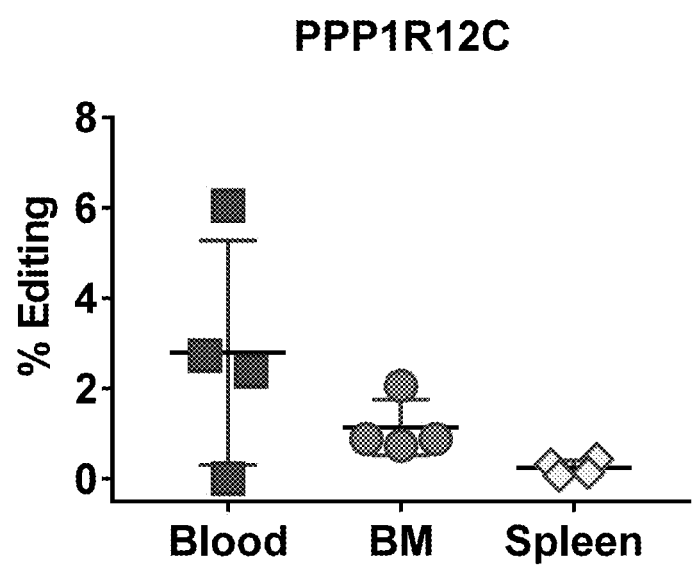
FIG. 9 is a graph showing the percentage of alleles having integration of the FP coding sequence in blood, bone marrow ("BM"), and spleen cells from NSG mice xenografted with human HSCs following administration of the AAVS1-FP vector packaged in AAVHSC7 and AAVHSC17 capsids.

Data from the AAVHSC7 and AAVHSC17 groups were pooled. As shown in FIG. 9, in the transplanted NSG mice administered with AAVS1-FP vector, the allelic frequency of integration was about 3% in the blood, and about 1% in the bone marrow. This result suggested that the AAVHSC7 and AAVHSC17 capsids efficiently delivered a vector for integration into the AAVS1 locus, and can potentially be used for delivering HBB editing therapeutic vectors.

A modified animal model reconstituted with HBB defective primary human CD34$^+$ HSCs is useful for testing correction of HBB mutations using a correction vector or correction vector as described in the foregoing examples. For example, the correction vector packaged in an AAV clade F capsid, such as an AAVHSC7, AAVHSC15 or AAVHSC17 capsid, can be administered to the reconstituted animal. The integration efficiency can be measured by collecting blood or bone marrow samples and quantifying the percentage of cells in which desired homologous recombination has occurred either in a broad population or in a specific type of cells, such as progenitors of erythrocytes.

The animal reconstituted with HBB defective primary human CD34$^+$ HSCs are expected to manifest hemoglobinopathy due to lack of an HBB gene, and can be used to determine the efficacy and safety of HBB correction vectors packaged in various AAV capsids. Efficacy is assessed by measuring reticulocyte count, complete blood counts (CBCs), blood smears and targeted integration of the vector sequence. Safety is assessed by measuring the levels of hepatic transaminases such as aspartate transaminase (AST) and alanine transaminase (ALT).

This model can also be used to assess the longevity of HBB correction after each administration, thereby optimizing the dosing regimen.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

We claim:

1. A replication-defective adeno-associated virus (AAV) comprising:
   a) an AAV capsid comprising an AAV Clade F capsid protein; and
   b) a correction genome comprising from 5' to 3':
      (i) a 5' AAV ITR nucleotide sequence as set forth in SEQ ID NO: 18;
      (ii) a 5' homology arm nucleotide sequence;
      (iii) an editing element for editing a target locus in an HBB gene;
      (iv) a 3' homology arm nucleotide sequence;
      wherein the 5' homology arm, the editing element and the 3' homology arm of (ii), (iii) and (iv) consists of the nucleotide sequence as set forth in SEQ ID NO: 34 and
      (v) a 3' AAV ITR nucleotide sequence as set forth in SEQ ID NO: 19.

2. A replication-defective adeno-associated virus (AAV) comprising:
   a) an AAV capsid comprising an AAV Clade F capsid protein; and
   b) a correction genome comprising from 5' to 3':
      (i) a 5' AAV ITR nucleotide sequence as set forth in SEQ ID NO: 18;
      (ii) a 5' homology arm nucleotide sequence;
      (iii) an editing element for editing a target locus in an HBB gene;
      (iv) a 3' homology arm nucleotide sequence;
      wherein the 5' homology arm, the editing element and the 3' homology arm of (ii), (iii) and (iv) consists of the nucleotide sequence as set forth in SEQ ID NO: 38, and
      (v) a 3' AAV ITR nucleotide sequence as set forth in SEQ ID NO: 19.

3. A composition comprising the AAV of claim 1 or claim 2, and a pharmaceutically acceptable carrier.

* * * * *

```
                        SEQUENCE LISTING

<160> NUMBER OF SEQ ID NOS: 115

<210> SEQ ID NO 1
<211> LENGTH: 736
<212> TYPE: PRT
<213> ORGANISM: Artificial Sequence
<220> FEATURE:
<223> OTHER INFORMATION: adeno-associated AAV9

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175
```

```
Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590
```

```
Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 2
<211> LENGTH: 736
<212> TYPE: PRT
<213> ORGANISM: Artificial Sequence
<220> FEATURE:
<223> OTHER INFORMATION: novel AAV isolate

<400> SEQUENCE: 2

Met Thr Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Glu Gly Ala Asp Gly Val Gly Ser Ser
    210                 215                 220
```

```
Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
        290                 295                 300

Asn Trp Gly Phe Arg Pro Lys Gln Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
```

```
                      645                 650                 655
Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 3
<211> LENGTH: 736
<212> TYPE: PRT
<213> ORGANISM: Artificial Sequence
<220> FEATURE:
<223> OTHER INFORMATION: novel AAV isolate

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
```

```
                275                 280                 285
Phe His Cys His Phe Ser Pro Arg Asp Trp Gln Arg Leu Ile Asn Asn
290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Pro Phe Pro
                355                 360                 365
Ala Asp Val Phe Met Ile Pro Gln Tyr Gly Tyr Leu Thr Leu Asn Asp
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Lys Thr Ile Asn Gly Ser Gly Gln Asn Gln Gln Thr Leu Lys Phe Ser
450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
                500                 505                 510
Gly Arg Asn Ser Leu Met Asn Pro Gly Pro Ala Met Ala Ser His Lys
                515                 520                 525
Glu Gly Glu Asp Arg Phe Phe Pro Leu Ser Gly Ser Leu Ile Phe Gly
                530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
                580                 585                 590
Thr Gly Trp Val Gln Asn Gln Gly Ile Leu Pro Gly Met Val Trp Gln
                595                 600                 605
Asp Arg Asp Val Tyr Leu Gln Gly Pro Ile Trp Ala Lys Ile Pro His
                610                 615                 620
Thr Gly Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
                660                 665                 670
Gln Tyr Ser Thr Gly Gln Val Ser Val Glu Ile Glu Trp Glu Leu Gln
                675                 680                 685
Lys Glu Asn Ser Lys Arg Trp Asn Pro Glu Ile Gln Tyr Thr Ser Asn
                690                 695                 700
```

-continued

Tyr Tyr Lys Ser Asn Asn Val Glu Phe Ala Val Asn Thr Gly Gly Val
705                 710                 715                 720

Tyr Ser Glu Pro Arg Pro Ile Gly Thr Arg Tyr Leu Thr Arg Asn Leu
                725                 730                 735

<210> SEQ ID NO 4
<211> LENGTH: 736
<212> TYPE: PRT
<213> ORGANISM: Artificial Sequence
<220> FEATURE:
<223> OTHER INFORMATION: novel AAV isolate

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Ile Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Tyr Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 5
<211> LENGTH: 736

<212> TYPE: PRT
<213> ORGANISM: Artificial Sequence
<220> FEATURE:
<223> OTHER INFORMATION: novel AAV isolate

<400> SEQUENCE: 5

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Asp
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380
```

```
Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
        420                 425                 430

Asp Arg Leu Met Asn Pro Leu Ile Asp Gln Tyr Leu Tyr Tyr Leu Ser
    435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
        500                 505                 510

Gly Arg Asn Ser Leu Met Asn Pro Gly Pro Ala Met Ala Ser His Lys
    515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
        580                 585                 590

Thr Gly Trp Val Gln Asn Gln Gly Ile Leu Pro Gly Met Val Trp Gln
    595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
        660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 6
<211> LENGTH: 736
<212> TYPE: PRT
<213> ORGANISM: Artificial Sequence
<220> FEATURE:
<223> OTHER INFORMATION: novel AAV isolate

<400> SEQUENCE: 6

Met Ala Ala Asp Gly Tyr Leu Pro Asp Trp Leu Glu Asp Asn Leu Ser
1               5                   10                  15
```

-continued

```
Glu Gly Ile Arg Glu Trp Trp Ala Leu Lys Pro Gly Ala Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Leu Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
```

|   |   |   |   |   | 435 |   |   |   |   | 440 |   |   |   |   | 445 |   |   |
|---|---|---|---|---|---|---|---|---|---|---|---|---|---|---|---|---|---|

Lys Thr Ile Asn Gly Ser Gly Gln Asn Gln Gln Thr Leu Lys Phe Ser
          450                    455                    460

Val Ala Gly Ser Ser Asn Met Ala Val Gln Gly Arg Asn Tyr Ile Pro
465                   470                    475                    480

Gly Pro Ser Tyr Arg Gln Gln Arg Val Ser Thr Thr Val Thr Gln Asn
                    485                    490                    495

Asn Asn Ser Glu Phe Ala Trp Pro Gly Ala Ser Ser Trp Ala Leu Asn
          500                    505                    510

Gly Arg Asn Ser Leu Met Asn Pro Gly Pro Ala Met Ala Ser His Lys
                    515                    520                    525

Glu Gly Glu Asp Arg Phe Phe Pro Leu Ser Gly Ser Leu Ile Phe Gly
          530                    535                    540

Lys Gln Gly Thr Gly Arg Asp Asn Val Asp Ala Asp Lys Val Met Ile
545                   550                    555                    560

Thr Asn Glu Glu Glu Ile Lys Thr Thr Asn Pro Val Ala Thr Glu Ser
                    565                    570                    575

Tyr Gly Gln Val Ala Thr Asn His Gln Ser Ala Gln Ala Gln Ala Gln
          580                    585                    590

Thr Gly Trp Val Gln Asn Gln Gly Ile Leu Pro Gly Met Val Trp Gln
                    595                    600                    605

Asp Arg Asp Val Tyr Leu Gln Gly Pro Ile Trp Ala Lys Ile Pro His
610                   615                    620

Thr Asp Gly Asn Phe His Pro Ser Pro Leu Met Gly Gly Phe Gly Met
625                   630                    635                    640

Lys His Pro Pro Pro Gln Ile Leu Ile Lys Asn Thr Pro Val Pro Ala
                    645                    650                    655

Asp Pro Pro Thr Ala Phe Asn Lys Asp Lys Leu Asn Ser Phe Ile Thr
          660                    665                    670

Gln Tyr Ser Thr Gly Gln Val Ser Val Glu Ile Glu Trp Glu Leu Gln
                    675                    680                    685

Lys Glu Asn Ser Lys Arg Trp Asn Pro Glu Ile Gln Tyr Thr Ser Asn
          690                    695                    700

Tyr Tyr Lys Ser Asn Asn Val Glu Phe Ala Val Asn Thr Glu Gly Val
705                   710                    715                    720

Tyr Ser Glu Pro Arg Pro Ile Gly Thr Arg Tyr Leu Thr Arg Asn Leu
                    725                    730                    735

<210> SEQ ID NO 7
<211> LENGTH: 736
<212> TYPE: PRT
<213> ORGANISM: Artificial Sequence
<220> FEATURE:
<223> OTHER INFORMATION: novel AAV isolate

<400> SEQUENCE: 7

Met Ala Ala Asp Gly Tyr Leu Pro Asp Trp Leu Glu Asp Asn Leu Ser
1                      5                    10                    15

Glu Gly Ile Arg Glu Trp Trp Ala Leu Lys Pro Gly Ala Pro Gln Pro
                    20                    25                    30

Lys Ala Asn Gln Gln His Gln Asp Asn Ala Arg Gly Leu Val Leu Pro
                        35                    40                    45

Gly Tyr Lys Tyr Leu Gly Pro Gly Asn Gly Leu Asp Lys Gly Glu Pro
          50                    55                    60

Val Asn Ala Ala Asp Ala Ala Ala Leu Glu His Asp Lys Ala Tyr Asp

```
            65                  70                  75                  80
Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
                115                 120                 125

Leu Gly Leu Val Glu Glu Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
                195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
                290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
                370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
                450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495
```

```
Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Arg Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 8
<211> LENGTH: 736
<212> TYPE: PRT
<213> ORGANISM: Artificial Sequence
<220> FEATURE:
<223> OTHER INFORMATION: novel AAV isolate

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Val Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125
```

```
Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
                195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
                370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
530                 535                 540
```

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 9
<211> LENGTH: 736
<212> TYPE: PRT
<213> ORGANISM: Artificial Sequence
<220> FEATURE:
<223> OTHER INFORMATION: novel AAV isolate

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
    130                 135                 140

Pro Val Glu Gln Ser Pro Arg Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

```
Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
```

```
            595                 600                 605
Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Phe Gly Met
625                 630                 635                 640

Lys His Pro Pro Pro Gln Ile Leu Ile Lys Asn Thr Pro Val Pro Ala
                        645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                    725                 730                 735
```

<210> SEQ ID NO 10
<211> LENGTH: 736
<212> TYPE: PRT
<213> ORGANISM: Artificial Sequence
<220> FEATURE:
<223> OTHER INFORMATION: novel AAV isolate

<400> SEQUENCE: 10

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
                35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Cys Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
```

```
            225                 230                 235                 240
        Thr Thr Ser Thr Arg Thr Trp Ala Leu Pro Thr Tyr Asn Asn His Leu
                        245                 250                 255
        Tyr Lys Gln Ile Ser Asn Ser Thr Ser Gly Ser Ser Asn Asp Asn
                        260                 265                 270
        Ala Tyr Phe Gly Tyr Ser Thr Pro Trp Gly Tyr Phe Asp Phe Asn Arg
                        275                 280                 285
        Phe His Cys His Phe Ser Pro Arg Asp Trp Gln Arg Leu Ile Asn Asn
                    290                 295                 300
        Asn Trp Gly Phe Arg Pro Lys Arg Leu Asn Phe Lys Leu Phe Asn Ile
        305                 310                 315                 320
        Gln Val Lys Glu Val Thr Asp Asn Asn Gly Val Lys Thr Ile Ala Asn
                            325                 330                 335
        Asn Leu Thr Ser Thr Val Gln Val Phe Thr Asp Ser Asp Tyr Gln Leu
                        340                 345                 350
        Pro Tyr Val Leu Gly Ser Ala His Glu Gly Cys Leu Pro Pro Phe Pro
                    355                 360                 365
        Ala Asp Val Phe Met Ile Pro Gln Tyr Gly Tyr Leu Thr Leu Asn Asp
        370                 375                 380
        Gly Ser Gln Ala Val Gly Arg Ser Ser Phe Tyr Cys Leu Glu Tyr Phe
        385                 390                 395                 400
        Pro Ser Gln Met Leu Arg Thr Gly Asn Asn Phe Gln Phe Ser Tyr Glu
                        405                 410                 415
        Phe Glu Asn Val Pro Phe His Ser Ser Tyr Ala His Ser Gln Ser Leu
                    420                 425                 430
        Asp Arg Leu Met Asn Pro Leu Ile Asp Gln Tyr Leu Tyr Tyr Leu Ser
                435                 440                 445
        Lys Thr Ile Asn Gly Ser Gly Gln Asn Gln Gln Thr Leu Lys Phe Ser
        450                 455                 460
        Val Ala Gly Pro Ser Asn Met Ala Val Gln Gly Arg Asn Tyr Ile Pro
        465                 470                 475                 480
        Gly Pro Ser Tyr Arg Gln Gln Arg Val Ser Thr Thr Val Thr Gln Asn
                        485                 490                 495
        Asn Asn Ser Glu Phe Ala Trp Pro Gly Ala Ser Ser Trp Ala Leu Asn
                    500                 505                 510
        Gly Arg Asn Ser Leu Met Asn Pro Gly Pro Ala Met Ala Ser His Lys
                515                 520                 525
        Glu Gly Glu Asp Arg Phe Phe Pro Leu Ser Gly Ser Leu Ile Phe Gly
            530                 535                 540
        Lys Gln Gly Thr Gly Arg Asp Asn Val Asp Ala Asp Lys Val Met Ile
        545                 550                 555                 560
        Thr Asn Glu Glu Glu Ile Lys Thr Thr Asn Pro Val Ala Thr Glu Ser
                        565                 570                 575
        Tyr Gly Gln Val Ala Thr Asn His Gln Ser Ala Gln Ala Gln Ala Gln
                    580                 585                 590
        Thr Gly Trp Val Gln Asn Gln Gly Ile Leu Pro Gly Met Val Trp Gln
                595                 600                 605
        Asp Arg Asp Val Tyr Leu Gln Gly Pro Ile Trp Ala Lys Ile Pro His
            610                 615                 620
        Thr Asp Gly Asn Phe His Pro Ser Pro Leu Met Gly Gly Phe Gly Met
        625                 630                 635                 640
        Lys His Pro Pro Pro Gln Ile Leu Ile Lys Asn Thr Pro Val Pro Ala
                        645                 650                 655
```

```
Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 11
<211> LENGTH: 736
<212> TYPE: PRT
<213> ORGANISM: Artificial Sequence
<220> FEATURE:
<223> OTHER INFORMATION: novel AAV isolate

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Arg Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

```
Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Lys Asn Ser Lys Arg Trp Asn Pro Glu Ile Gln Tyr Thr Ser Asn
    690                 695                 700
```

```
Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735
```

<210> SEQ ID NO 12
<211> LENGTH: 736
<212> TYPE: PRT
<213> ORGANISM: Artificial Sequence
<220> FEATURE:
<223> OTHER INFORMATION: novel AAV isolate

<400> SEQUENCE: 12

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro His Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335
```

```
Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Asn
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Met Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 13
<211> LENGTH: 736
<212> TYPE: PRT

<213> ORGANISM: Artificial Sequence
<220> FEATURE:
<223> OTHER INFORMATION: novel AAV isolate

<400> SEQUENCE: 13

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
```

-continued

```
                385                 390                 395                 400
        Pro Ser Gln Met Leu Arg Thr Gly Asn Asn Phe Gln Phe Ser Tyr Glu
                        405                 410                 415

Phe Glu Asn Val Pro Phe His Ser Ser Tyr Ala His Ser Gln Ser Leu
                        420                 425                 430

Asp Arg Leu Met Asn Pro Leu Ile Asp Gln Tyr Leu Tyr Tyr Leu Ser
                        435                 440                 445

Lys Thr Ile Asn Gly Ser Gly Gln Asn Gln Gln Thr Leu Lys Phe Ser
                        450                 455                 460

Val Ala Gly Pro Ser Asn Met Ala Val Gln Gly Arg Asn Tyr Ile Pro
        465                 470                 475                 480

Gly Pro Ser Tyr Arg Gln Gln Arg Val Ser Thr Thr Val Thr Gln Asn
                        485                 490                 495

Asn Asn Ser Glu Phe Ala Trp Pro Arg Ala Ser Ser Trp Ala Leu Asn
                        500                 505                 510

Gly Arg Asn Ser Leu Met Asn Pro Gly Pro Ala Met Ala Ser His Lys
                        515                 520                 525

Glu Gly Glu Asp Arg Phe Phe Pro Leu Ser Gly Ser Leu Ile Phe Gly
                        530                 535                 540

Lys Gln Gly Thr Gly Arg Asp Asn Val Asp Ala Asp Lys Val Met Ile
        545                 550                 555                 560

Thr Asn Glu Glu Glu Ile Lys Thr Thr Asn Pro Val Ala Thr Glu Ser
                        565                 570                 575

Tyr Gly Gln Val Ala Thr Asn His Gln Ser Ala Gln Ala Gln Ala Gln
                        580                 585                 590

Thr Gly Trp Val Gln Asn Gln Gly Ile Leu Pro Gly Met Val Trp Gln
                        595                 600                 605

Asp Arg Asp Val Tyr Leu Gln Gly Pro Ile Trp Ala Lys Ile Pro His
                        610                 615                 620

Thr Asp Gly Asn Phe His Pro Ser Pro Leu Met Gly Gly Phe Gly Met
        625                 630                 635                 640

Lys His Pro Pro Pro Gln Ile Leu Ile Lys Asn Thr Pro Val Pro Ala
                        645                 650                 655

Asp Pro Pro Thr Ala Phe Asn Lys Asp Lys Leu Asn Ser Phe Ile Thr
                        660                 665                 670

Gln Tyr Ser Thr Gly Gln Val Ser Val Glu Ile Glu Trp Glu Leu Gln
                        675                 680                 685

Lys Glu Asn Ser Lys Arg Trp Asn Pro Glu Ile Gln Tyr Thr Ser Asn
                        690                 695                 700

Tyr Tyr Lys Ser Asn Asn Val Glu Phe Ala Val Asn Thr Glu Gly Val
        705                 710                 715                 720

Tyr Ser Glu Pro Arg Pro Ile Gly Thr Arg Tyr Leu Thr Arg Asn Leu
                        725                 730                 735

<210> SEQ ID NO 14
<211> LENGTH: 26
<212> TYPE: DNA
<213> ORGANISM: Artificial Sequence
<220> FEATURE:
<223> OTHER INFORMATION: Splice acceptor

<400> SEQUENCE: 14
ctgacctctt ctcttcctcc cacagg                                          26

<210> SEQ ID NO 15
```

```
<211> LENGTH: 736
<212> TYPE: PRT
<213> ORGANISM: Artificial Sequence
<220> FEATURE:
<223> OTHER INFORMATION: novel AAV isolate

<400> SEQUENCE: 15
```

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

-continued

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
        420                 425                 430

Asp Arg Leu Met Asn Pro Leu Ile Asp Gln Tyr Leu Tyr Tyr Leu Ser
    435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Arg Ala Ser Ser Trp Ala Leu Asn
        500                 505                 510

Gly Arg Asn Ser Leu Met Asn Pro Gly Pro Ala Met Ala Ser His Lys
    515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
        580                 585                 590

Thr Gly Trp Val Gln Asn Gln Gly Ile Leu Pro Gly Met Val Trp Gln
    595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
        660                 665                 670

Gln Tyr Ser Thr Gly Gln Val Ser Val Glu Ile Glu Trp Glu Arg Gln
    675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 16
<211> LENGTH: 736
<212> TYPE: PRT
<213> ORGANISM: Artificial Sequence
<220> FEATURE:
<223> OTHER INFORMATION: novel AAV isolate

<400> SEQUENCE: 16

Met Ala Ala Asp Gly Tyr Leu Pro Asp Trp Leu Glu Asp Asn Leu Ser
1               5                   10                  15

```
Glu Gly Ile Arg Glu Trp Trp Ala Leu Lys Pro Gly Ala Pro Gln Pro
             20                  25                  30

Lys Ala Asn Gln Gln His Gln Asp Asn Ala Arg Gly Leu Val Leu Pro
         35                  40                  45

Gly Tyr Lys Tyr Leu Gly Pro Gly Asn Gly Leu Asp Lys Gly Glu Pro
 50                  55                  60

Val Asn Ala Ala Asp Ala Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Ala Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430
```

Asp Arg Leu Met Asn Pro Leu Ile Asp Gln Tyr Leu Tyr Leu Ser
            435                 440                 445

Lys Thr Ile Asn Gly Ser Gly Gln Asn Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 17
<211> LENGTH: 736
<212> TYPE: PRT
<213> ORGANISM: Artificial Sequence
<220> FEATURE:
<223> OTHER INFORMATION: novel AAV isolate

<400> SEQUENCE: 17

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
50                  55                  60

```
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
```

```
                    485                 490                 495
Asn Asn Ser Glu Ile Ala Trp Pro Arg Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Cys Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 18
<211> LENGTH: 145
<212> TYPE: DNA
<213> ORGANISM: Artificial Sequence
<220> FEATURE:
<223> OTHER INFORMATION: AAV2 5' ITR

<400> SEQUENCE: 18
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcct                                          145

<210> SEQ ID NO 19
<211> LENGTH: 145
<212> TYPE: DNA
<213> ORGANISM: Artificial Sequence
<220> FEATURE:
<223> OTHER INFORMATION: AAV2 3' ITR

<400> SEQUENCE: 19
aggaacccct agtgatggag ttggccactc cctctctgcg cgctcgctcg ctcactgagg     60
ccgggcgacc aaaggtcgcc cgacgcccgg gctttgcccg ggcggcctca gtgagcgagc    120
gagcgcgcag agagggagtg gccaa                                          145
```

<210> SEQ ID NO 20
<211> LENGTH: 167
<212> TYPE: DNA
<213> ORGANISM: Artificial Sequence
<220> FEATURE:
<223> OTHER INFORMATION: AAV5 5' ITR

<400> SEQUENCE: 20

```
ctctccccccc tgtcgcgttc gctcgctcgc tggctcgttt ggggggtgg cagctcaaag    60 agctgccaga cgacggccct ctggccgtcg ccccccaaa cgagccagcg agcgagcgaa   120
cgcgacaggg gggagagtgc cacactctca agcaaggggg ttttgta                167
```

<210> SEQ ID NO 21
<211> LENGTH: 167
<212> TYPE: DNA
<213> ORGANISM: Artificial Sequence
<220> FEATURE:
<223> OTHER INFORMATION: AAV5 3' ITR

<400> SEQUENCE: 21

```
tacaaaacct ccttgcttga gagtgtggca ctctcccccc tgtcgcgttc gctcgctcgc    60
tggctcgttt ggggggtgg cagctcaaag agctgccaga cgacggccct ctggccgtcg   120 ccccccaaa cgagccagcg agcgagcgaa cgcgacaggg gggagag                 167
```

<210> SEQ ID NO 22
<211> LENGTH: 621
<212> TYPE: PRT
<213> ORGANISM: Artificial Sequence
<220> FEATURE:
<223> OTHER INFORMATION: AAV2 Rep

<400> SEQUENCE: 22

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
```

```
            195                 200                 205
Pro Asn Ser Asp Ala Pro Val Ile Arg Ser Lys Thr Ser Ala Arg Tyr
210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
                260                 265                 270

Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
                340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
                500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
                580                 585                 590

Ile His His Ile Met Gly Lys Val Pro Asp Ala Cys Thr Ala Cys Asp
            595                 600                 605

Leu Val Asn Val Asp Leu Asp Asp Cys Ile Phe Glu Gln
610                 615                 620
```

<210> SEQ ID NO 23
<211> LENGTH: 1833
<212> TYPE: DNA
<213> ORGANISM: Homo sapiens

<400> SEQUENCE: 23

| | | | | | |
|---|---|---|---|---|---|
| cggctgtcat | cacttagacc | tcaccctgtg | gagccacacc | ctaggggttgg | ccaatctact | 60 |
| cccaggagca | gggagggcag | gagccagggc | tgggcataaa | agtcagggca | gagccatcta | 120 |
| ttgcttacat | ttgcttctga | cacaactgtg | ttcactagca | acctcaaaca | gacaccatgg | 180 |
| tgcatctgac | tcctgaggag | aagtctgccg | ttactgccct | gtggggcaag | gtgaacgtgg | 240 |
| atgaagttgg | tggtgaggcc | ctgggcaggt | tggtatcaag | gttacaagac | aggtttaagg | 300 |
| agaccaatag | aaactgggca | tgtggagaca | gagaagactc | ttgggtttct | gataggcact | 360 |
| gactctctct | gcctattggt | ctattttccc | acccttaggc | tgctggtggt | ctacccttgg | 420 |
| acccagaggt | tctttgagtc | ctttggggat | ctgtccactc | ctgatgctgt | tatgggcaac | 480 |
| cctaaggtga | aggctcatgg | caagaaagtg | ctcggtgcct | ttagtgatgg | cctggctcac | 540 |
| ctggacaacc | tcaagggcac | ctttgccaca | ctgagtgagc | tgcactgtga | caagctgcac | 600 |
| gtggatcctg | agaacttcag | ggtgagtcta | tgggacgctt | gatgttttct | ttccccttct | 660 |
| tttctatggt | taagttcatg | tcataggaag | gggataagta | acagggtaca | gtttagaatg | 720 |
| ggaaacagac | gaatgattgc | atcagtgtgg | aagtctcagg | atcgttttag | tttcttttat | 780 |
| ttgctgttca | taacaattgt | tttcttttgt | ttaattcttg | ctttcttttt | ttttcttctc | 840 |
| cgcaatttttt | actattatac | ttaatgcctt | aacattgtgt | ataacaaaag | gaaatatctc | 900 |
| tgagatacat | taagtaactt | aaaaaaaaac | tttacacagt | ctgcctagta | cattactatt | 960 |
| tggaatatat | gtgtgcttat | ttgcatattc | ataatctccc | tactttatttt | tcttttatt | 1020 |
| ttaattgata | cataatcatt | atacatattt | atgggttaaa | gtgtaatgtt | ttaatatgtg | 1080 |
| tacacatatt | gaccaaatca | gggtaatttt | gcatttgtaa | ttttaaaaaa | tgctttcttc | 1140 |
| ttttaatata | cttttttgtt | tatcttattt | ctaatacttt | ccctaatctc | tttctttcag | 1200 |
| ggcaataatg | atacaatgta | tcatgcctct | ttgcaccatt | ctaaagaata | acagtgataa | 1260 |
| tttctgggtt | aaggcaatag | caatatctct | gcatataaat | atttctgcat | ataaattgta | 1320 |
| actgatgtaa | gaggtttcat | attgctaata | gcagctacaa | tccagctacc | attctgcttt | 1380 |
| tattttatgg | ttgggataag | gctggattat | tctgagtcca | agctaggccc | ttttgctaat | 1440 |
| catgttcata | cctcttatct | tcctcccaca | gctcctgggc | aacgtgctgg | tctgtgtgct | 1500 |
| ggcccatcac | tttggcaaag | aattcacccc | accagtgcag | gctgcctatc | agaaagtggt | 1560 |
| ggctggtgtg | gctaatgccc | tggcccacaa | gtatcactaa | gctcgctttc | ttgctgtcca | 1620 |
| atttctatta | aaggttcctt | tgttccctaa | gtccaactac | taaactgggg | gatattatga | 1680 |
| agggccttga | gcatctggat | tctgcctaat | aaaaaacatt | tattttcatt | gcaatgatgt | 1740 |
| atttaaatta | tttctgaata | ttttactaaa | aagggaatgt | gggaggtcag | tgcatttaaa | 1800 |
| acataaagaa | atgaagagct | agttcaaacc | ttg | | | 1833 |

<210> SEQ ID NO 24
<211> LENGTH: 1833
<212> TYPE: DNA
<213> ORGANISM: Artificial Sequence
<220> FEATURE:
<223> OTHER INFORMATION: HBB sequence from 5' mutation to 3' mutation
  with silent codon alterations

<400> SEQUENCE: 24

```
cggctgtcat cacttagacc tcaccctgtg gagccacacc ctagggttgg ccaatctact      60
cccaggagca gggagggcag gagccagggc tgggcataaa agtcagggca gagccatcta    120
ttgcttacat ttgcttctga cacaactgtg ttcactagca acctcaaaca gacaccatgg    180
tccacctcac accagaagaa aaaagtgctg taacagctct ctggggaaaa gtcaatgtcg    240
acgaggtagg gggggaagct ctcggaaggt tggtatcaag gttacaagac aggtttaagg    300
agaccaatag aaactgggca tgtggagaca gagaagactc ttgggtttct gataggcact    360
gactctctct gcctattggt ctattttccc acccttagac tcctcgtcgt gtatccatgg    420
acacaaagat ttttcgaaag cttcggagac ctcagcacac cagacgcagt aatgggaaat    480
ccaaaagtca agcacacgg aaaaaaggtc ctgggggctt tctctgacgg actcgcacat    540
ctcgataatc tgaaaggaac attcgctacc ctctctgaac tccattgcga taaactccat    600
gtcgacccag aaaattttag agtgagtcta tgggacgctt gatgttttct ttccccttct    660
tttctatggt taagttcatg tcataggaag gggataagta acagggtaca gtttagaatg    720
ggaaacagac gaatgattgc atcagtgtgg aagtctcagg atcgttttag tttcttttat    780
ttgctgttca taacaattgt tttcttttgt ttaattcttg ctttcttttt ttttcttctc    840
cgcaattttt actattatac ttaatgcctt aacattgtgt ataacaaaag gaaatatctc    900
tgagatacat taagtaactt aaaaaaaaac tttacacagt ctgcctagta cattactatt    960
tggaatatat gtgtgcttat ttgcatattc ataatctccc tactttattt tcttttattt   1020
ttaattgata cataatcatt atacatattt atgggttaaa gtgtaatgtt ttaatatgtg   1080
tacacatatt gaccaaatca gggtaatttt gcatttgtaa ttttaaaaaa tgctttcttc   1140
ttttaatata ctttttttgtt tatcttattt ctaatacttt ccctaatctc tttctttcag   1200
ggcaataatg atacaatgta tcatgcctct ttgcaccatt ctaaagaata acagtgataa   1260
tttctgggtt aaggcaatag caatatctct gcatataaat atttctgcat ataaattgta   1320
actgatgtaa gaggtttcat attgctaata gcagctacaa tccagctacc attctgcttt   1380
tattttatgg ttgggataag gctggattat tctgagtcca agctaggccc ttttgctaat   1440
catgttcata cctcttatct tcctcccaca gctgctcgga aatgtcctcg tgtgcgtcct   1500
cgctcaccat ttcggaaagg agtttacacc tcctgtccaa gcagcttacc aaaaggtcgt   1560
cgcagggggtc gcaaacgctc tcgctcataa ataccattag gctcgctttc ttgctgtcca   1620
atttctatta aaggttcctt tgttcccctaa gtccaactac taaactgggg gatattatga   1680
agggccttga gcatctggat tctgcctaat aaaaaacatt tattttcatt gcaatgatgt   1740
atttaaatta tttctgaata ttttactaaa agggaatgt gggaggtcag tgcatttaaa   1800
acataaagaa atgaagagct agttcaaacc ttg                                1833
```

<210> SEQ ID NO 25
<211> LENGTH: 1845
<212> TYPE: DNA
<213> ORGANISM: Artificial Sequence
<220> FEATURE:
<223> OTHER INFORMATION: HBB sequence from 5' mutation to 3' mutation
with Linker

<400> SEQUENCE: 25

```
cggctgtcat cacttagacc tcaccctgtg gagccacacc ctagggttgg ccaatctact      60
cccaggagca gggagggcag gagccagggc tgggcataaa agtcagggca gagccatcta    120
```

```
ttgcttacat ttgcttctga cacaactgtg ttcactagca acctcaaaca gacaccatgg      180
tgcatctgac tcctgaggag aagtctgccg ttactgccct gtggggcaag gtgaacgtgg      240
atgaagttgg tggtgaggcc ctgggcaggt tggtatcaag gttacaagac aggactagta      300
tcgattttaa ggagaccaat agaaactggg catgtggaga cagagaagac tcttgggttt      360
ctgataggca ctgactctct ctgcctattg gtctattttc ccaccettag ctgctggtg       420 gtctacccTT ggacccagag gttctttgag tcctttgggg atctgtccac tcctgatgct      480
gttatgggca accctaaggt gaaggctcat ggcaagaaag tgctcggtgc ctttagtgat      540
ggcctggctc acctggacaa cctcaagggc acctttgcca cactgagtga gctgcactgt      600
gacaagctgc acgtggatcc tgagaacttc agggtgagtc tatgggacgc ttgatgtttt      660
cttTccccTT ctTttctatg gttaagttca tgtcatagga aggggataag taacagggta      720
cagtttagaa tgggaaacag acgaatgatt gcatcagtgt ggaagtctca ggatcgtttt      780
agttTctttt atttgctgtt cataacaatt gttttctttt gtttaattct tgctttcttt      840
ttttttcttc tccgcaattt ttactattat acttaatgcc ttaacattgt gtataacaaa      900
aggaaatatc tctgagatac attaagtaac ttaaaaaaaa actttacaca gtctgcctag      960
tacattacta tttggaatat atgtgtgctt atttgcatat tcataatctc cctactttat     1020
tttcttttat ttttaattga tacataatca ttatacatat ttatgggtta aagtgtaatg     1080
ttttaatatg tgtacacata ttgaccaaat cagggtaatt ttgcatttgt aattttaaaa     1140
aatgctttct tctttTaata tacttTTttg tttatcttat ttctaatact ttccctaatc     1200
tcttTctttc agggcaataa tgatacaatg tatcatgcct ctttgcacca ttctaaagaa     1260
taacagtgat aatttctggg ttaaggcaat agcaatatct ctgcatataa atatttctgc     1320
atataaattg taactgatgt aagaggtttc atattgctaa tagcagctac aatccagcta     1380
ccattctgct tttatttTat ggttgggata aggctggatt attctgagtc caagctaggc     1440
ccttttgcta atcatgttca tacctcttat cttcctccca cagctcctgg gcaacgtgct     1500
ggtctgtgtg ctggcccatc actttggcaa agaattcacc ccaccagtgc aggctgccta     1560
tcagaaagtg gtggctggtg tggctaatgc cctggcccac aagtatcact aagctcgctt     1620
tcttgctgtc caatttctat taaaggttcc tttgttccct aagtccaact actaaactgg     1680
gggatattat gaagggcctt gagcatctgg attctgccta taaaaaaaca tttatTttca     1740
ttgcaatgat gtatttaaat tatttctgaa tatTttacta aaagggaat gtgggaggtc      1800 agtgcattta aaacataaag aaatgaagag ctagttcaaa ccttg                     1845
```

<210> SEQ ID NO 26
<211> LENGTH: 1845
<212> TYPE: DNA
<213> ORGANISM: Artificial Sequence
<220> FEATURE:
<223> OTHER INFORMATION: HBB sequence from 5' mutation to 3' mutation
      with silent codon alterations, with Linker

<400> SEQUENCE: 26

```
cggctgtcat cacttagacc tcaccctgtg gagccacacc ctagggttgg ccaatctact       60
cccaggagca gggagggcag gagccagggc tgggcataaa agtcagggca gagccatcta      120
ttgcttacat ttgcttctga cacaactgtg ttcactagca acctcaaaca gacaccatgg      180
tccacctcac accagaagaa aaagtgctg taacagctct ctgggaaaa gtcaatgtcg       240 acgaggtagg gggggaagct ctcggaaggt tggtatcaag gttacaagac aggactagta      300
```

```
tcgattttaa ggagaccaat agaaactggg catgtggaga cagagaagac tcttgggttt      360
ctgataggca ctgactctct ctgcctattg gtctatttc ccaccttag actcctcgtc      420
gtgtatccat ggacacaaag attttcgaa agcttcggag acctcagcac accagacgca      480
gtaatgggaa atccaaaagt caaagcacac ggaaaaaagg tcctggggc tttctctgac      540
ggactcgcac atctcgataa tctgaaagga acattcgcta ccctctctga actccattgc      600
gataaactcc atgtcgaccc agaaaatttt agagtgagtc tatgggacgc ttgatgtttt      660
ctttccccctt cttttctatg gttaagttca tgtcatagga aggggataag taacagggta      720
cagtttagaa tggaaacag acgaatgatt gcatcagtgt ggaagtctca ggatcgtttt      780
agtttctttt atttgctgtt cataacaatt gttttctttt gtttaattct tgctttcttt      840
tttttcttc tccgcaattt ttactattat acttaatgcc ttaacattgt gtataacaaa      900
aggaaatatc tctgagatac attaagtaac ttaaaaaaaa actttacaca gtctgcctag      960
tacattacta tttggaatat atgtgtgctt atttgcatat tcataatctc cctactttat     1020
tttcttttat ttttaattga tacataatca ttatacatat ttatgggtta aagtgtaatg     1080
ttttaatatg tgtacacata ttgaccaaat cagggtaatt ttgcatttgt aattttaaaa     1140
aatgctttct tcttttaata acttttttg tttatcttat ttctaatact ttccctaatc     1200
tctttctttc agggcaataa tgatacaatg tatcatgcct ctttgcacca ttctaaagaa     1260
taacagtgat aatttctggg ttaaggcaat agcaatatct ctgcatataa atatttctgc     1320
atataaattg taactgatgt aagaggtttc atattgctaa tagcagctac aatccagcta     1380
ccattctgct tttatttat ggttgggata aggctggatt attctgagtc caagctaggc     1440
ccttttgcta atcatgttca tacctcttat cttcctccca cagctgctcg gaaatgtcct     1500
cgtgtgcgtc ctcgctcacc atttcggaaa ggagtttaca cctcctgtcc aagcagctta     1560
ccaaaaggtc gtcgcagggg tcgcaaacgc tctcgctcat aaataccatt aggctcgctt     1620
tcttgctgtc caatttctat taaaggttcc tttgttccct aagtccaact actaaactgg     1680
gggatattat gaagggcctt gagcatctgg attctgccta ataaaaaaca tttattttca     1740
ttgcaatgat gtatttaaat tatttctgaa tattttacta aaagggaat gtgggaggtc     1800
agtgcattta aaacataaag aaatgaagag ctagttcaaa ccttg                    1845
```

<210> SEQ ID NO 27
<211> LENGTH: 444
<212> TYPE: DNA
<213> ORGANISM: Homo sapiens

<400> SEQUENCE: 27

```
atggtgcatc tgactcctga ggagaagtct gccgttactg ccctgtgggg caaggtgaac       60
gtggatgaag ttggtggtga ggccctgggc aggctgctgg tggtctaccc ttggacccag      120
aggttctttg agtcctttgg ggatctgtcc actcctgatg ctgttatggg caaccctaag      180
gtgaaggctc atggcaagaa agtgctcggt gcctttagtg atggcctggc tcacctggac      240
aacctcaagg gcacctttgc cacactgagt gagctgcact gtgacaagct gcacgtggat      300
cctgagaact tcaggctcct gggcaacgtg ctggtctgtg ctgccca tcactttggc      360
aaagaattca ccccaccagt gcaggctgcc tatcagaaag tggtggctgg tgtggctaat      420
gccctggccc acaagtatca ctaa                                            444
```

<210> SEQ ID NO 28

```
<211> LENGTH: 444
<212> TYPE: DNA
<213> ORGANISM: Artificial Sequence
<220> FEATURE:
<223> OTHER INFORMATION: cDNA sequences with silent codon alterations

<400> SEQUENCE: 28
atggtccacc tcacaccaga agaaaaaagt gctgtaacag ctctctgggg aaaagtcaat      60
gtcgacgagg taggggggga agctctcgga agactcctcg tcgtgtatcc atggacacaa     120 agattttctcg aaagcttcgg agacctcagc acaccagacg cagtaatggg aaatccaaaa    180
gtcaaagcac acggaaaaaa ggtcctgggg gctttctctg acggactcgc acatctcgat     240
aatctgaaag gaacattcgc taccctctct gaactccatt gcgataaact ccatgtcgac     300
ccagaaaatt ttagactgct cggaaatgtc ctcgtgtgcg tcctcgctca ccatttcgga     360
aaggagttta cacctcctgt ccaagcagct taccaaaagg tcgtcgcagg ggtcgcaaac    420
gctctcgctc ataaatacca ttag                                            444

<210> SEQ ID NO 29
<211> LENGTH: 3533
<212> TYPE: DNA
<213> ORGANISM: Artificial Sequence
<220> FEATURE:
<223> OTHER INFORMATION: hHBB-hL-014 vector, ITRs not included

<400> SEQUENCE: 29
atcaacctag gctccagata gccatagaag aaccaaacac tttctgcgtg tgtgagaata      60
atcagagtga gatttttttca caagtacctg atgagggttg agacaggtag aaaaagtgag    120
agatctctat ttatttagca ataatagaga aagcatttaa gagaataaag caatggaaat     180
aagaaatttg taaatttcct tctgataact agaaatagag gatccagttt cttttggtta     240
acctaaattt tatttcattt tattgtttta ttttatttta ttttatttta ttttgtgtaa     300
tcgtagtttc agagtgttag agctgaaagg aagaagtagg agaaacatgc aaagtaaaag     360
tataacactt tccttactaa accgacatgg gtttccaggt aggggcagga ttcaggatga     420
ctgacagggc ccttagggaa cactgagacc ctacgctgac ctcataaatg cttgctacct     480
ttgctgtttt aattacatct tttaatagca ggaagcagaa ctctgcactt caaaagtttt     540
tcctcacctg aggagttaat ttagtacaag gggaaaaagt acaggggat gggagaaagg      600 cgatcacgtt gggaagctat agagaaagaa gagtaaattt tagtaaagga ggtttaaaca    660
aacaaaatat aaagagaaat aggaacttga atcaaggaaa tgatttttaaa acgcagtatt   720 cttagtggac tagaggaaaa aaataatctg agccaagtag aagacctttt cccctcctac    780
ccctactttc taagtcacag aggcttttttg ttcccccaga cactcttgca gattagtcca    840
ggcagaaaca gttagatgtc cccagttaac ctcctatttg acaccactga ttaccccatt    900
gatagtcaca ctttgggttg taagtgactt tttattttatt tgtattttttg actgcattaa    960 gaggtctcta gttttttatc tcttgtttcc caaaacctaa taagtaacta atgcacagag   1020
cacattgatt tgtatttatt ctattttttag acataattta ttagcatgca tgagcaaatt   1080
aagaaaaaca acaacaaatg aatgcatata tatgtatatg tatgtgtgta tatatacaca   1140
catatatata tatatttttt cttttcttac cagaaggttt taatccaaat aaggagaaga   1200
tatgcttaga accgaggtag agttttcatc cattctgtcc tgtaagtatt ttgcatattc   1260
tggagacgca ggaagagatc catctacata tcccaaagct gaattatggt agacaaaact   1320
cttccacttt tagtgcatca acttcttatt tgtgtaataa gaaaattggg aaaacgatct   1380
```

```
tcaatatgct taccaagctg tgattccaaa tattacgtaa atacacttgc aaaggaggat    1440
gtttttagta gcaatttgta ctgatggtat ggggccaaga gatatatctt agagggaggg    1500
ctgagggttt gaagtccaac tcctaagcca gtgccagaag agccaaggac aggtacggct    1560
gtcatcactt agacctcacc ctgtggagcc acaccctagg gttggccaat ctactcccag    1620
gagcagggag ggcaggagcc agggctgggc ataaaagtca gggcagagcc atctattgct    1680
tacatttgct tctgacacaa ctgtgttcac tagcaacctc aaacagacac catggtgcat    1740
ctgactcctg aggagaagtc tgccgttact gccctgtggg gcaaggtgaa cgtggatgaa    1800
gttggtggtg aggccctggg caggttggta tcaaggttac aagacaggac tagtatcgat    1860
tttaaggaga ccaatagaaa ctgggcatgt ggagacagag aagactcttg ggtttctgat    1920
aggcactgac tctctctgcc tattggtcta tttttcccacc cttaggctgc tggtggtcta    1980
cccttggacc cagaggttct ttgagtcctt tggggatctg tccactcctg atgctgttat    2040
gggcaaccct aaggtgaagg ctcatggcaa gaaagtgctc ggtgccttta gtgatggcct    2100
ggctcacctg gacaacctca agggcacctt tgccacactg agtgagctgc actgtgacaa    2160
gctgcacgtg gatcctgaga acttcagggt gagtctatgg gacgcttgat gttttctttc    2220
cccttctttt ctatggttaa gttcatgtca taggaagggg ataagtaaca gggtacagtt    2280
tagaatggga aacagacgaa tgattgcatc agtgtggaag tctcaggatc gttttagttt    2340 ctttatttg ctgttcataa caattgtttt cttttgttta attcttgctt tctttttttt    2400
tcttctccgc aattttttact attatactta atgccttaac attgtgtata acaaaaggaa    2460
atatctctga gatacattaa gtaacttaaa aaaaaacttt acacagtctg cctagtacat    2520
tactatttgg aatatatgtg tgcttatttg catattcata atctccctac tttatttcct    2580
tttattttta attgatacat aatcattata catatttatg ggttaaagtg taatgttta    2640 atatgtgtac acatattgac caaatcaggg taattttgca tttgtaattt taaaaaatgc    2700
tttcttcttt taatatactt ttttgtttat cttatttcta atactttccc taatctcttt    2760
ctttcagggc aataatgata caatgtatca tgcctctttg caccattcta aagaataaca    2820
gtgataattt ctgggttaag gcaatagcaa tatctctgca tataaatatt tctgcatata    2880
aattgtaact gatgtaagag gtttcatatt gctaatagca gctacaatcc agctaccatt    2940
ctgcttttat tttatggttg ggataaggct ggattattct gagtccaagc tagggccctt    3000
tgctaatcat gttcataccct cttatcttcc tcccacagct cctgggcaac gtgctggtct    3060
gtgtgctggc ccatcacttt ggcaaagaat tcaccccacc agtgcaggct gcctatcaga    3120
aagtggtggc tggtgtggct aatgccctgg cccacaagta tcactaagct cgctttcttg    3180
ctgtccaatt tctattaaag gttcctttgt tccctaagtc caactactaa actggggat    3240 attatgaagg gccttgagca tctggattct gcctaataaa aaacatttat tttcattgca    3300
atgatgtatt taaattattt ctgaatattt tactaaaaag ggaatgtggg aggtcagtgc    3360
atttaaaaca taagaaatg aagagctagt tcaaaccttg ggaaaataca ctatatctta    3420
aactccatga agaaggtgaa ggctgcaaac agctaatgca cattggcaac agcccctgat    3480
gcatatgcct tattcatccc tcagaaaagg attcaagtag aggcttgatt tgg           3533
```

<210> SEQ ID NO 30
<211> LENGTH: 3521
<212> TYPE: DNA
<213> ORGANISM: Artificial Sequence
<220> FEATURE:

<223> OTHER INFORMATION: hHBB-hL-014 vector, ITRs not included, Linker removed

<400> SEQUENCE: 30

```
atcaacctag gctccagata gccatagaag aaccaaacac tttctgcgtg tgtgagaata    60
atcagagtga gatttttca  caagtacctg atgagggttg agacaggtag aaaaagtgag   120
agatctctat ttatttagca ataatagaga aagcatttaa gagaataaag caatggaaat   180
aagaaatttg taaatttcct tctgataact agaaatagag gatccagttt cttttggtta   240
acctaaattt tatttcattt tattgtttta ttttatttta ttttatttta ttttgtgtaa   300
tcgtagtttc agagtgttag agctgaaagg aagaagtagg agaaacatgc aaagtaaaag   360
tataacactt tccttactaa accgacatgg gtttccaggt aggggcagga ttcaggatga   420
ctgacagggc ccttagggaa cactgagacc ctacgctgac ctcataaatg cttgctacct   480
ttgctgtttt aattacatct tttaatagca ggaagcagaa ctctgcactt caaaagtttt   540
tcctcacctg aggagttaat ttagtacaag gggaaaaagt acaggggat  gggagaaagg   600
cgatcacgtt gggaagctat agagaaagaa gagtaaattt tagtaaagga ggtttaaaca   660
aacaaaatat aaagagaaat aggaacttga atcaaggaaa tgattttaaa acgcagtatt   720
cttagtggac tagaggaaaa aaataatctg agccaagtag aagacctttt cccctcctac   780
ccctactttc taagtcacag aggctttttg ttcccccaga cactcttgca gattagtcca   840
ggcagaaaca gttagatgtc cccagttaac ctcctatttg acaccactga ttaccccatt   900
gatagtcaca ctttgggttg taagtgactt tttatttatt tgtattttg  actgcattaa   960
gaggtctcta gttttttatc tcttgtttcc caaaacctaa taagtaacta atgcacagag  1020
cacattgatt tgtatttatt ctatttttag acataattta ttagcatgca tgagcaaatt  1080
aagaaaaaca acaacaaatg aatgcatata tatgtatatg tatgtgtgta tatatacaca  1140
catatatata tatatttttt cttttcttac cagaaggttt taatccaaat aaggagaaga  1200
tatgcttaga accgaggtag agttttcatc cattctgtcc tgtaagtatt ttgcatattc  1260
tggagacgca ggaagagatc catctacata tcccaaagct gaattatggt agacaaaact  1320
cttccacttt tagtgcatca acttcttatt tgtgtaataa gaaaattggg aaaacgatct  1380
tcaatatgct taccaagctg tgattccaaa tattacgtaa atacacttgc aaaggaggat  1440
gttttttagta gcaatttgta ctgatggtat ggggccaaga gatatatctt agagggaggg  1500
ctgagggttt gaagtccaac tcctaagcca gtgccagaag agccaaggac aggtacggct  1560
gtcatcactt agacctcacc ctgtggagcc acacccctagg gttggccaat ctactcccag  1620
gagcagggag ggcaggagcc agggctgggc ataaaagtca gggcagagcc atctattgct  1680
tacatttgct tctgacacaa ctgtgttcac tagcaacctc aaacagacac catggtgcat  1740
ctgactcctg aggagaagtc tgccgttact gccctgtggg gcaaggtgaa cgtggatgaa  1800
gttggtggtg aggccctggg caggttggta tcaaggttac aagacaggtt taaggagacc  1860
aatagaaact gggcatgtgg agacagagaa gactcttggg tttctgatag cactgactc   1920
tctctgccta ttggtctatt ttcccaccct taggctgctg gtggtctacc cttggaccca  1980
gaggttcttt gagtcctttg gggatctgtc cactcctgat gctgttatgg gcaaccctaa  2040
ggtgaaggct catggcaaga aagtgctcgg tgcctttagt gatggcctgg ctcacctgga  2100
caacctcaag ggcaccttg  ccacactgag tgagctgcac tgtgacaagc tgcacgtgga  2160
tcctgagaac ttcagggtga gtctatggga cgcttgatgt tttctttccc cttctttct   2220
```

```
atggttaagt tcatgtcata ggaaggggat aagtaacagg gtacagttta gaatgggaaa    2280
cagacgaatg attgcatcag tgtggaagtc tcaggatcgt tttagtttct tttatttgct    2340
gttcataaca attgttttct tttgtttaat tcttgctttc ttttttttc ttctccgcaa    2400 tttttactat tatacttaat gccttaacat tgtgtataac aaaaggaaat atctctgaga    2460
tacattaagt aacttaaaaa aaaactttac acagtctgcc tagtacatta ctatttggaa    2520
tatatgtgtg cttatttgca tattcataat ctccctactt tatttctttt attttttaat    2580
tgatacataa tcattataca tatttatggg ttaaagtgta atgttttaat atgtgtacac    2640
atattgacca atcagggta attttgcatt tgtaatttta aaaatgctt tcttcttta     2700 atatactttt ttgtttatct tatttctaat actttcccta atctctttct ttcagggcaa    2760
taatgataca atgtatcatg cctctttgca ccattctaaa gaataacagt gataatttct    2820
gggttaaggc aatagcaata tctctgcata taaatatttc tgcatataaa ttgtaactga    2880
tgtaagaggt ttcatattgc taatagcagc tacaatccag ctaccattct gcttttattt    2940
tatggttggg ataaggctgg attattctga gtccaagcta ggcccttttg ctaatcatgt    3000
tcatacctct tatcttcctc ccacagctcc tgggcaacgt gctggtctgt gtgctggccc    3060
atcactttgg caaagaattc accccaccag tgcaggctgc ctatcagaaa gtggtggctg    3120
gtgtggctaa tgccctggcc cacaagtatc actaagctcg ctttcttgct gtccaatttc    3180
tattaaaggt tcctttgttc cctaagtcca actactaaac tgggggatat tatgaagggc    3240
cttgagcatc tggattctgc ctaataaaaa acatttattt tcattgcaat gatgtattta    3300
aattatttct gaatatttta ctaaaaaggg aatgtgggag gtcagtgcat ttaaaacata    3360
aagaaatgaa gagctagttc aaaccttggg aaaatacact atatcttaaa ctccatgaaa    3420
gaaggtgagc tgcaaacag ctaatgcaca ttggcaacag cccctgatgc atatgcctta    3480
ttcatccctc agaaaaggat tcaagtagag gcttgatttg g                        3521
```

<210> SEQ ID NO 31
<211> LENGTH: 3168
<212> TYPE: DNA
<213> ORGANISM: Artificial Sequence
<220> FEATURE:
<223> OTHER INFORMATION: hHBB-hL-001 vector, ITRs not included

<400> SEQUENCE: 31

```
ttatttattt gtattttga ctgcattaag aggtctctag tttttatct cttgtttccc     60 aaaacctaat aagtaactaa tgcacagagc acattgattt gtattattc tattttaga    120 cataatttat tagcatgcat gagcaaatta agaaaaacaa caacaaatga atgcatatat   180
atgtatatgt atgtgtgtat atatacacac atatatatat atattttttc ttttcttacc   240
agaaggtttt aatccaaata aggagaagat atgcttagaa ccgaggtaga gttttcatcc   300
attctgtcct gtaagtattt tgcatattct ggagacgcag gaagagatcc atctacatat   360
cccaaagctg aattatggta gacaaaactc ttccactttt agtgcatcaa cttcttattt   420
gtgtaataag aaaattggga aaacgatctt caatatgctt accaagctgt gattccaaat   480
attacgtaaa tacacttgca aaggaggatg tttttagtag caatttgtac tgatggtatg   540
gggccaagag atatatctta gagggagggc tgagggtttg aagtccaact cctaagccag   600
tgccagaaga gccaaggaca ggtacggctg tcatcactta gacctcaccc tgtggagcca   660 cacccctaggg ttggcaatc tactcccagg agcaggagg caggagcca gggctgggca    720 taaaagtcag ggcagagcca tctattgctt acatttgctt ctgacacaac tgtgttcact   780
```

```
agcaacctca aacagacacc atggtgcatc tgactcctga ggagaagtct gccgttactg     840
ccctgtgggg caaggtgaac gtggatgaag ttggtggtga ggccctgggc aggttggtat     900
caaggttaca agacaggact agtatcgatt ttaaggagac aatagaaac tgggcatgtg      960
gagacagaga agactcttgg gtttctgata ggcactgact ctctctgcct attggtctat    1020
tttcccaccc ttaggctgct ggtggtctac ccttggaccc agaggttctt tgagtccttt    1080
ggggatctgt ccactcctga tgctgttatg gcaaccctaa aggtgaaggc tcatggcaag    1140
aaagtgctcg gtgcctttag tgatggcctg gctcacctgg acaacctcaa gggcaccttt    1200
gccacactga gtgagctgca ctgtgacaag ctgcacgtgg atcctgagaa cttcaggtg     1260
agtctatggg acgcttgatg ttttcttcc ccttcttttc tatggttaag ttcatgtcat     1320
aggaagggga taagtaacag ggtacagttt agaatgggaa acagacgaat gattgcatca    1380
gtgtggaagt ctcaggatcg ttttagtttc ttttatttgc tgttcataac aattgttttc    1440
ttttgtttaa ttcttgcttt ctttttttt cttctccgca atttttacta ttatacttaa    1500
tgccttaaca ttgtgtataa caaaaggaaa tatctctgag atacattaag taacttaaaa    1560
aaaaacttta cacagtctgc ctagtacatt actatttgga atatatgtgt gcttatttgc    1620
atattcataa tctccctact ttatttctt ttatttttaa ttgatacata atcattatac    1680
atatttatgg gttaaagtgt aatgttttaa tatgtgtaca catattgacc aaatcagggt    1740
aattttgcat ttgtaatttt aaaaaatgct ttcttcttt aatatacttt tttgtttatc     1800
ttatttctaa tactttccct aatctctttc tttcagggca ataatgatac aatgtatcat    1860
gcctctttgc accattctaa agaataacag tgataatttc tgggttaagg caatagcaat    1920
atctctgcat ataaatattt ctgcatataa attgtaactg atgtaagagg tttcatattg    1980
ctaatagcag ctacaatcca gctaccattc tgcttttatt ttatggttgg gataaggctg    2040
gattattctg agtccaagct aggccctttt gctaatcatg ttcataccte ttatcttcct    2100
cccacagctc ctgggcaacg tgctggtctg tgtgctggcc catcactttg gcaaagaatt    2160
caccccacca gtgcaggctg cctatcagaa agtggtggct ggtgtggcta atgccctggc    2220
ccacaagtat cactaagctc gctttcttgc tgtccaattt ctattaaagg ttcctttgtt    2280
ccctaagtcc aactactaaa ctgggggata ttatgaaggg ccttgagcat ctggattctg    2340
cctaataaaa aacatttatt ttcattgcaa tgatgtattt aaattatttc tgaatatttt    2400
actaaaaagg gaatgtggga ggtcagtgca tttaaaacat aaagaaatga agagctagtt    2460
caaaccttgg gaaaatacac tatatcttaa actccatgaa agaaggtgag gctgcaaaca    2520
gctaatgcac attggcaaca gccctgatg catatgcctt attcatccct cagaaaagga    2580
ttcaagtaga ggcttgattt ggaggttaaa gttttgctat gctgtatttt acattactta    2640
ttgttttagc tgtcctcatg aatgtctttt cactacccat ttgcttatcc tgcatctctc    2700
agccttgact ccactcagtt ctcttgctta gagataccac cttcccctg aagtgttcct     2760
tccatgtttt acggcgagat ggtttctcct cgcctggcca ctcagcctta gttgtctctg    2820
ttgtcttata gaggtctact tgaagaagga aaaacagggg tcatggtttg actgtccctgt   2880
gagcccttct tccctgcctc ccccactcac agtgacccgg aatctgcagt gctagtctcc    2940
cggaactatc actctttcac agtctgcttt ggaaggactg ggcttagtat gaaaagttag    3000
gactgagaag aatttgaaag gcggcttttt gtagcttgat attcactact gtcttattac    3060
cctgtcatag gcccacccca aatggaagtc ccattcttcc tcaggatgtt taagattagc    3120
```
attcaggaag agatcagagg tctgctggct cccttatcat gtcccctta                3168

<210> SEQ ID NO 32
<211> LENGTH: 3156
<212> TYPE: DNA
<213> ORGANISM: Artificial Sequence
<220> FEATURE:
<223> OTHER INFORMATION: hHBB-hL-001 vector, ITRs not included, Linker
      removed

<400> SEQUENCE: 32

```
ttatttattt gtatttttga ctgcattaag aggtctctag ttttttatct cttgtttccc      60
aaaacctaat aagtaactaa tgcacagagc acattgattt gtatttattc tattttaga     120
cataatttat tagcatgcat gagcaaatta agaaaaacaa caacaaatga atgcatatat    180
atgtatatgt atgtgtgtat atatacacac atatatatat atatttttc ttttcttacc     240
agaaggtttt aatccaaata aggagaagat atgcttagaa ccgaggtaga gttttcatcc    300
attctgtcct gtaagtattt tgcatattct ggagacgcag gaagagatcc atctacatat    360
cccaaagctg aattatggta gacaaaactc ttccactttt agtgcatcaa cttcttattt    420
gtgtaataag aaaattggga aaacgatctt caatatgctt accaagctgt gattccaaat    480
attacgtaaa tacacttgca aaggaggatg ttttttagtag caatttgtac tgatggtatg    540
gggccaagag atatatctta gagggagggc tgagggtttg aagtccaact cctaagccag    600
tgccagaaga gccaaggaca ggtacggctg tcatcactta gacctcaccc tgtggagcca    660
caccctaggg ttggccaatc tactcccagg agcaggagg gcaggagcca gggctgggca    720
taaaagtcag ggcagagcca tctattgctt acatttgctt ctgacacaac tgtgttcact    780
agcaacctca aacagacacc atggtgcatc tgactcctga ggagaagtct gccgttactg    840
ccctgtgggg caaggtgaac gtggatgaag ttggtggtga ggccctgggc aggttggtat    900
caaggttaca agacaggttt aaggagacca ataGaaactg ggcatgtgga gacagagaag    960
actcttgggt ttctgatagg cactgactct ctctgcctat tggtctattt tcccaccctt    1020
aggctgctgg tggtctaccc ttggacccag aggttctttg agtcctttgg ggatctgtcc    1080
actcctgatg ctgttatggg caaccctaag gtgaaggctc atggcaagaa agtgctcggt    1140
gcctttagtg atggcctggc tcacctggac aacctcaagg gcacctttgc cacactgagt    1200
gagctgcact gtgacaagct gcacgtggat cctgagaact tcagggtgag tctatgggac    1260
gcttgatgtt tcttttcccc ttcttttcta tggttaagtt catgtcatag gaaggggata    1320
agtaacaggg tacagtttag aatgggaaac agacgaatga ttgcatcagt gtggaagtct    1380
caggatcgtt ttagtttctt ttatttgctg ttcataacaa ttgttttctt tgtttaatt    1440
cttgctttct ttttttttct tctccgcaat ttttactatt atacttaatg ccttaacatt    1500
gtgtataaca aaaggaaata tctctgagat acattaagta acttaaaaaa aaactttaca    1560
cagtctgcct agtacattac tatttggaat atatgtgtgc ttatttgcat attcataatc    1620
tccctacttt atttttctttt attttaatt gatacataat cattatacat atttatgggt    1680
taaagtgtaa tgtttaata tgtgtacaca tattgaccaa atcagggtaa ttttgcattt    1740
gtaattttaa aaaatgcttt cttcttttaa tatacttttt tgtttatctt atttctaata    1800
ctttccctaa tctctttctt tcagggcaat aatgatacaa tgtatcatgc ctctttgcac    1860
cattctaaag aataacagtg ataatttctg ggttaaggca atagcaatat ctctgcatat    1920
aaatatttct gcatataaat tgtaactgat gtaagaggtt tcatattgct aatagcagct    1980
```

| | | |
|---|---|---|
| acaatccagc taccattctg cttttatttt atggttggga taaggctgga ttattctgag | 2040 |
| tccaagctag gcccttttgc taatcatgtt catacctctt atcttcctcc cacagctcct | 2100 |
| gggcaacgtg ctggtctgtg tgctggccca tcactttggc aaagaattca ccccaccagt | 2160 |
| gcaggctgcc tatcagaaag tggtggctgg tgtggctaat gccctggccc acaagtatca | 2220 |
| ctaagctcgc tttcttgctg tccaatttct attaaaggtt cctttgttcc ctaagtccaa | 2280 |
| ctactaaact gggggatatt atgaagggcc ttgagcatct ggattctgcc taataaaaaa | 2340 |
| catttatttt cattgcaatg atgtatttaa attatttctg aatattttac taaaaaggga | 2400 |
| atgtgggagg tcagtgcatt taaaacataa agaaatgaag agctagttca aaccttggga | 2460 |
| aaatacacta tatcttaaac tccatgaaag aaggtgaggc tgcaaacagc taatgcacat | 2520 |
| tggcaacagc ccctgatgca tatgccttat tcatccctca gaaaaggatt caagtagagg | 2580 |
| cttgatttgg aggttaaagt tttgctatgc tgtattttac attacttatt gttttagctg | 2640 |
| tcctcatgaa tgtcttttca ctacccattt gcttatcctg catctctcag ccttgactcc | 2700 |
| actcagttct cttgcttaga gataccacct ttcccctgaa gtgttccttc catgttttac | 2760 |
| ggcgagatgg tttctcctcg cctggccact cagccttagt tgtctctgtt gtcttataga | 2820 |
| ggtctacttg aagaaggaaa acaggggtc atggtttgac tgtcctgtga gcccttcttc | 2880 |
| cctgcctccc ccactcacag tgacccggaa tctgcagtgc tagtctcccg gaactatcac | 2940 |
| tctttcacag tctgctttgg aaggactggg cttagtatga aaagttagga ctgagaagaa | 3000 |
| tttgaaaggc ggcttttttgt agcttgatat tcactactgt cttattaccc tgtcataggc | 3060 |
| ccaccccaaa tggaagtccc attcttcctc aggatgttta agattagcat tcaggaagag | 3120 |
| atcagaggtc tgctggctcc cttatcatgt cccttta | 3156 |

<210> SEQ ID NO 33
<211> LENGTH: 3168
<212> TYPE: DNA
<213> ORGANISM: Artificial Sequence
<220> FEATURE:
<223> OTHER INFORMATION: hHBB-hLW-013 vector, ITRs not included

<400> SEQUENCE: 33

| | | |
|---|---|---|
| ttatttattt gtattttttga ctgcattaag aggtctctag ttttttatct cttgtttccc | 60 |
| aaaacctaat aagtaactaa tgcacagagc acattgattt gtatttattc tattttaga | 120 |
| cataatttat tagcatgcat gagcaaatta agaaaaacaa caacaaatga atgcatatat | 180 |
| atgtatatgt atgtgtgtat atatacacac atatatatat atattttttc ttttcttacc | 240 |
| agaaggtttt aatccaaata aggagaagat atgcttagaa ccgaggtaga gttttcatcc | 300 |
| attctgtcct gtaagtattt tgcatattct ggagacgcag gaagagatcc atctacatat | 360 |
| cccaaagctg aattatggta gacaaaactc ttccactttt agtgcatcaa cttcttattt | 420 |
| gtgtaataag aaaattggga aaacgatctt caatatgctt accaagctgt gattccaaat | 480 |
| attacgtaaa tacacttgca aaggaggatg ttttagtag caatttgtac tgatggtatg | 540 |
| gggccaagag atatatctta gagggagggc tgagggtttg aagtccaact cctaagccag | 600 |
| tgccagaaga gccaaggaca ggtacggctg tcatcactta gacctcaccc tgtgagcca | 660 |
| caccctaggg ttggccaatc tactcccagg agcagggagg caggagcca gggctgggca | 720 |
| taaaagtcag ggcagagcca tctattgctt acatttgctt ctgacacaac tgtgttcact | 780 |
| agcaacctca aacagacacc atggtccacc tcacaccaga agaaaaaagt gctgtaacag | 840 |
| ctctctgggg aaaagtcaat gtcgacgagg taggggggga agctctcgga aggttggtat | 900 |

```
caaggttaca agacaggact agtatcgatt ttaaggagac caatagaaac tgggcatgtg    960
gagacagaga agactcttgg gtttctgata ggcactgact ctctctgcct attggtctat   1020
tttcccaccc ttagactcct cgtcgtgtat ccatggacac aaagattttt cgaaagcttc   1080
ggagacctca gcacaccaga cgcagtaatg ggaaatccaa aagtcaaagc acacggaaaa   1140
aaggtcctgg gggctttctc tgacggactc gcacatctcg ataatctgaa aggaacattc   1200
gctaccctct ctgaactcca ttgcgataaa ctccatgtcg acccagaaaa ttttagagtg   1260
agtctatggg acgcttgatg ttttctttcc ccttcttttc tatggttaag ttcatgtcat   1320
aggaagggga taagtaacag ggtacagttt agaatgggaa acagacgaat gattgcatca   1380
gtgtggaagt ctcaggatcg ttttagtttc ttttatttgc tgttcataac aattgttttc   1440
ttttgtttaa ttcttgcttt ctttttttt cttctccgca atttttacta ttatacttaa    1500
tgccttaaca ttgtgtataa caaaaggaaa tatctctgag atacattaag taacttaaaa   1560
aaaaactta cacagtctgc ctagtacatt actatttgga atatatgtgt gcttatttgc    1620
atattcataa tctccctact ttattttctt ttattttaa ttgatacata atcattatac    1680
atatttatgg gttaaagtgt aatgttttaa tatgtgtaca catattgacc aaatcagggt   1740
aattttgcat ttgtaatttt aaaaaatgct ttcttctttt aatatacttt tttgtttatc   1800
ttatttctaa tactttccct aatctctttc tttcagggca ataatgatac aatgtatcat   1860
gcctctttgc accattctaa agaataacag tgataatttc tgggttaagg caatagcaat   1920
atctctgcat ataaatattt ctgcatataa attgtaactg atgtaagagg tttcatattg   1980
ctaatagcag ctacaatcca gctaccattc tgcttttatt ttatggttgg gataaggctg   2040
gattattctg agtccaagct aggcccttt gctaatcatg ttcataccct ttatcttcct    2100
cccacagctg ctcggaaatg tcctcgtgtg cgtcctcgct caccatttcg gaaaggagtt   2160
tacacctcct gtccaagcag cttaccaaaa ggtcgtcgca ggggtcgcaa acgctctcgc   2220
tcataaatac cattaggctc gctttcttgc tgtccaattt ctattaaagg ttcctttgtt   2280
ccctaagtcc aactactaaa ctgggggata ttatgaaggg ccttgagcat ctggattctg   2340
cctaataaaa aacatttatt ttcattgcaa tgatgtattt aaattatttc tgaatatttt   2400
actaaaaagg gaatgtggga ggtcagtgca tttaaaacat aaagaaatga agagctagtt   2460
caaaccttgg gaaaatacac tatatcttaa actccatgaa agaaggtgag gctgcaaaca   2520
gctaatgcac attggcaaca gccccgtgatg catatgcctt attcatccct cagaaaagga   2580
ttcaagtaga ggcttgattt ggaggttaaa gttttgctat gctgtatttt acattactta   2640
ttgttttagc tgtcctcatg aatgtctttt cactacccat ttgcttatcc tgcatctctc   2700
agccttgact ccactcagtt ctcttgctta gagataccc cttccctg aagtgttcct     2760
tccatgtttt acggcgagat ggtttctcct cgcctggcca ctcagcctta gttgtctctg   2820
ttgtcttata gaggtctact tgaagaagga aaaacagggg tcatggtttg actgtcctgt   2880
gagcccttct tccctgcctc ccccactcac agtgacccgg aatctgcagt gctagtctcc   2940
cggaactatc actctttcac agtctgcttt ggaaggactg ggcttagtat gaaaagttag   3000
gactgagaag aatttgaaag gcggcttttt gtagcttgat attcactact gtcttattac   3060
cctgtcatag gcccacccca aatggaagtc ccattcttcc tcaggatgtt taagattagc   3120
attcaggaag agatcagagg tctgctggct cccttatcat gtcccctta              3168
```

<210> SEQ ID NO 34

<211> LENGTH: 3156
<212> TYPE: DNA
<213> ORGANISM: Artificial Sequence
<220> FEATURE:
<223> OTHER INFORMATION: hHBB-hLW-013 vector, ITRs not included, Linker removed

<400> SEQUENCE: 34

| | | | | | |
|---|---|---|---|---|---|
| ttatttattt | gtattttga | ctgcattaag | aggtctctag | ttttttatct | cttgtttccc | 60 |
| aaaacctaat | aagtaactaa | tgcacagagc | acattgattt | gtatttattc | tattttaga | 120 |
| cataatttat | tagcatgcat | gagcaaatta | agaaaaacaa | caacaaatga | atgcatatat | 180 |
| atgtatatgt | atgtgtgtat | atatacacac | atatatatat | atatttttc | ttttcttacc | 240 |
| agaaggtttt | aatccaaata | aggagaagat | atgcttagaa | ccgaggtaga | gttttcatcc | 300 |
| attctgtcct | gtaagtattt | tgcatattct | ggagacgcag | gaagagatcc | atctacatat | 360 |
| cccaaagctg | aattatggta | gacaaaactc | ttccactttt | agtgcatcaa | cttcttattt | 420 |
| gtgtaataag | aaaattggga | aaacgatctt | caatatgctt | accaagctgt | gattccaaat | 480 |
| attacgtaaa | tacacttgca | aaggaggatg | ttttagtag | caatttgtac | tgatggtatg | 540 |
| gggccaagag | atatatctta | gagggagggc | tgagggtttg | aagtccaact | cctaagccag | 600 |
| tgccagaaga | gccaaggaca | ggtacggctg | tcatcactta | gacctcaccc | tgtggagcca | 660 |
| caccctaggg | ttggccaatc | tactcccagg | agcaggagg | gcaggagcca | gggctgggca | 720 |
| taaaagtcag | ggcagagcca | tctattgctt | acatttgctt | ctgacacaac | tgtgttcact | 780 |
| agcaaccctca | aacagacacc | atggtccacc | tcacaccaga | agaaaaagt | gctgtaacag | 840 |
| ctctctgggg | aaaagtcaat | gtcgacgagg | tagggggga | agctctcgga | aggttggtat | 900 |
| caaggttaca | agacaggttt | aaggagacca | atagaaactg | ggcatgtgga | gacagagaag | 960 |
| actcttgggt | ttctgatagg | cactgactct | ctctgcctat | tggtctattt | tcccacccctt | 1020 |
| agactcctcg | tcgtgtatcc | atggacacaa | agatttttcg | aaagcttcgg | agacctcagc | 1080 |
| acaccagacg | cagtaatggg | aaatccaaaa | gtcaaagcac | acggaaaaaa | ggtcctgggg | 1140 |
| gctttctctg | acggactcgc | acatctcgat | aatctgaaag | gaacattcgc | taccctctct | 1200 |
| gaactccatt | gcgataaact | ccatgtcgac | ccagaaaatt | ttagagtgag | tctatgggac | 1260 |
| gcttgatgtt | tcttttcccc | ttcttttcta | tggttaagtt | catgtcatag | gaaggggata | 1320 |
| agtaacaggg | tacagtttag | aatgggaaac | agacgaatga | ttgcatcagt | gtggaagtct | 1380 |
| caggatcgtt | ttagtttctt | ttatttgctg | ttcataacaa | ttgttttctt | ttgtttaatt | 1440 |
| cttgctttct | tttttttct | tctccgcaat | ttttactatt | atacttaatg | ccttaacatt | 1500 |
| gtgtataaca | aaaggaaata | tctctgagat | acattaagta | acttaaaaaa | aaactttaca | 1560 |
| cagtctgcct | agtacattac | tatttggaat | atatgtgtgc | ttatttgcat | attcataatc | 1620 |
| tccctacttt | attttctttt | attttttaatt | gatacataat | cattatacat | atttatgggt | 1680 |
| taaagtgtaa | tgtttaaata | tgtgtacaca | tattgaccaa | atcagggtaa | ttttgcattt | 1740 |
| gtaattttaa | aaaatgcttt | cttcttttaa | tatacttttt | tgtttatctt | atttctaata | 1800 |
| cttttccctaa | tctctttctt | tcagggcaat | aatgatacaa | tgtatcatgc | ctctttgcac | 1860 |
| cattctaaag | aataacagtg | ataatttctg | ggttaaggca | atagcaatat | ctctgcatat | 1920 |
| aaatatttct | gcatataaat | tgtaactgat | gtaagaggtt | tcatattgct | aatagcagct | 1980 |
| acaatccagc | taccattctg | cttttatttt | atggttggga | taaggctgga | ttattctgag | 2040 |
| tccaagctag | gcccttttgc | taatcatgtt | catacctctt | atcttcctcc | cacagctgct | 2100 |

| | |
|---|---|
| cggaaatgtc ctcgtgtgcg tcctcgctca ccatttcgga aaggagttta caccctcctgt | 2160 |
| ccaagcagct taccaaaagg tcgtcgcagg ggtcgcaaac gctctcgctc ataaatacca | 2220 |
| ttaggctcgc tttcttgctg tccaatttct attaaaggtt cctttgttcc ctaagtccaa | 2280 |
| ctactaaact gggggatatt atgaagggcc ttgagcatct ggattctgcc taataaaaaa | 2340 |
| catttatttt cattgcaatg atgtatttaa attatttctg aatattttac taaaaaggga | 2400 |
| atgtgggagg tcagtgcatt taaaacataa agaaatgaag agctagttca aaccttggga | 2460 |
| aaatacacta tatcttaaac tccatgaaag aaggtgaggc tgcaaacagc taatgcacat | 2520 |
| tggcaacagc ccctgatgca tatgccttat tcatccctca gaaaaggatt caagtagagg | 2580 |
| cttgatttgg aggttaaagt tttgctatgc tgtattttac attacttatt gttttagctg | 2640 |
| tcctcatgaa tgtcttttca ctacccattt gcttatcctg catctctcag ccttgactcc | 2700 |
| actcagttct cttgcttaga gataccacct ttcccctgaa gtgttccttc catgttttac | 2760 |
| ggcgagatgg tttctcctcg cctggccact cagccttagt tgtctctgtt gtcttataga | 2820 |
| ggtctacttg aagaaggaaa acagggggtc atggtttgac tgtcctgtga gcccttcttc | 2880 |
| cctgcctccc ccactcacag tgaccccggaa tctgcagtgc tagtctcccg gaactatcac | 2940 |
| tctttcacag tctgctttgg aaggactggg cttagtatga aaagttagga ctgagaagaa | 3000 |
| tttgaaaggc ggcttttttgt agcttgatat tcactactgt cttattaccc tgtcataggc | 3060 |
| ccaccccaaa tggaagtccc attcttcctc aggatgttta agattagcat tcaggaagag | 3120 |
| atcagaggtc tgctggctcc cttatcatgt cccctta | 3156 |

<210> SEQ ID NO 35
<211> LENGTH: 2468
<212> TYPE: DNA
<213> ORGANISM: Artificial Sequence
<220> FEATURE:
<223> OTHER INFORMATION: hHBB-hL-011 vector, ITRs not included

<400> SEQUENCE: 35

| | |
|---|---|
| ttatttatttt gtattttttga ctgcattaag aggtctctag tttttttatct cttgtttccc | 60 |
| aaaacctaat aagtaactaa tgcacagagc acattgattt gtatttattc tatttttaga | 120 |
| cataatttat tagcatgcat gagcaaatta agaaaaacaa caacaaatga atgcatatat | 180 |
| atgtatatgt atgtgtgtat atatacacac atatatatat atattttttc ttttcttacc | 240 |
| agaaggtttt aatccaaata aggagaagat atgcttagaa ccgaggtaga gttttcatcc | 300 |
| attctgtcct gtaagtattt tgcatattct ggagacgcag gaagagatcc atctacatat | 360 |
| cccaaagctg aattatggta gacaaaactc ttccactttt agtgcatcaa cttcttattt | 420 |
| gtgtaataag aaaattggga aaacgatctt caatatgctt accaagctgt gattccaaat | 480 |
| attacgtaaa tacacttgca aaggaggatg tttttagtag caatttgtac tgatggtatg | 540 |
| gggccaagag atatatctta gagggagggc tgagggtttg aagtccaact cctaagccag | 600 |
| tgccagaaga gccaaggaca ggtacggctg tcatcactta gacctcaccc tgtggagcca | 660 |
| caccctaggg ttggccaatc tactcccagg agcagggagg gcaggagcca gggctgggca | 720 |
| taaaagtcag ggcagagcca tctattgctt acatttgctt ctgacacaac tgtgttcact | 780 |
| agcaacctca aacagacacc atggtgcatc tgactcctga ggagaagtct gccgttactg | 840 |
| ccctgtgggg caaggtgaac gtggatgaag ttggtggtga ggccctgggc aggttggtat | 900 |
| caaggttaca agacaggact agtatcgatt ttaaggagac caatagaaac tgggcatgtg | 960 |
| gagacagaga agactcttgg gtttctgata ggcactgact ctctctgcct attggtctat | 1020 |

```
tttcccaccc ttaggctgct ggtggtctac ccttggaccc agaggttctt tgagtccttt    1080
ggggatctgt ccactcctga tgctgttatg ggcaacccta aggtgaaggc tcatggcaag    1140
aaagtgctcg gtgcctttag tgatggcctg gctcacctgg acaacctcaa gggcaccttt    1200
gccacactga gtgagctgca ctgtgacaag ctgcacgtgg atcctgagaa cttcagggtg    1260
agtctatggg acgcttgatg ttttctttcc ccttcttttc tatggttaag ttcatgtcat    1320
aggaagggga taagtaacag ggtacagttt agaatgggaa acagacgaat gattgcatca    1380
gtgtggaagt ctcaggatcg ttttagtttc ttttatttgc tgttcataac aattgttttc    1440
ttttgtttaa ttcttgcttt cttttttttt cttctccgca atttttacta ttatacttaa    1500
tgccttaaca ttgtgtataa caaaaggaaa tatctctgag atacattaag taacttaaaa    1560
aaaaacttta cacagtctgc ctagtacatt actatttgga atatatgtgt gcttatttgc    1620
atattcataa tctccctact ttattttctt ttattttaa ttgatacata atcattatac     1680
atatttatgg gttaaagtgt aatgttttaa tatgtgtaca catattgacc aaatcagggt    1740
aattttgcat ttgtaatttt aaaaaatgct ttcttctttt aatatacttt tttgtttatc    1800
ttatttctaa tactttcccct aatctctttc tttcagggca ataatgatac aatgtatcat   1860
gcctctttgc accattctaa agaataacag tgataatttc tgggttaagg caatagcaat    1920
atctctgcat ataaatattt ctgcatataa attgtaactg atgtaagagg tttcatattg    1980
ctaatagcag ctacaatcca gctaccattc tgcttttatt ttatggttgg gataaggctg    2040
gattattctg agtccaagct aggccctttt gctaatcatg ttcataccct ttatcttcct   2100
cccacagctc ctgggcaacg tgctggtctg tgtgctggcc catcactttg gcaaagaatt    2160
caccccacca gtgcaggctg cctatcagaa agtggtggct ggtgtggcta atgccctggc    2220
ccacaagtat cactaagctc gctttcttgc tgtccaattt ctattaaagg ttcctttgtt    2280
ccctaagtcc aactactaaa ctgggggata ttatgaaggg ccttgagcat ctggattctg    2340
cctaataaaa aacatttatt ttcattgcaa tgatgtattt aaattatttc tgaatatttt    2400
actaaaaagg gaatgtggga ggtcagtgca tttaaaacat aaagaaatga agagctagtt    2460
caaacctt                                                             2468
```

<210> SEQ ID NO 36
<211> LENGTH: 2456
<212> TYPE: DNA
<213> ORGANISM: Artificial Sequence
<220> FEATURE:
<223> OTHER INFORMATION: hHBB-hL-011 vector, ITRs not included, Linker removed

<400> SEQUENCE: 36

```
ttatttattt gtattttga ctgcattaag aggtctctag ttttttatct cttgtttccc      60
aaaacctaat aagtaactaa tgcacagagc acattgattt gtatttattc tattttaga    120 cataatttat tagcatgcat gagcaaatta agaaaaacaa caacaaatga atgcatatat    180
atgtatatgt atgtgtgtat atatacacac atatatatat atattttttc ttttcttacc    240
agaaggtttt aatccaaata aggagaagat atgcttagaa ccgaggtaga gttttcatcc    300
attctgtcct gtaagtattt tgcatattct ggagacgcag gaagagatcc atctacatat    360
cccaaagctg aattatggta gacaaaactc ttccactttt agtgcatcaa cttcttattt    420
gtgtaataag aaaattggga aaacgatctt caatatgctt accaagctgt gattccaaat    480
attacgtaaa tacacttgca aaggaggatg tttttagtag caatttgtac tgatggtatg    540
```

```
gggccaagag atatatctta gagggagggc tgagggtttg aagtccaact cctaagccag    600
tgccagaaga gccaaggaca ggtacggctg tcatcactta gacctcaccc tgtggagcca    660
caccctaggg ttggccaatc tactcccagg agcagggagg gcaggagcca gggctgggca    720
taaaagtcag ggcagagcca tctattgctt acatttgctt ctgacacaac tgtgttcact    780
agcaacctca aacagacacc atggtgcatc tgactcctga ggagaagtct gccgttactg    840
ccctgtgggg caaggtgaac gtggatgaag ttggtggtga ggccctgggc aggttggtat    900
caaggttaca agacaggttt aaggagacca atagaaactg ggcatgtgga cagagaaag    960 actcttgggt ttctgatagg cactgactct ctctgcctat tggtctattt tcccaccctt   1020
aggctgctgg tggtctaccc ttggacccag aggttctttg agtcctttgg ggatctgtcc   1080
actcctgatg ctgttatggg caaccctaag gtgaaggctc atggcaagaa agtgctcggt   1140
gcctttagtg atggcctggc tcacctggac aacctcaagg gcacctttgc cacactgagt   1200
gagctgcact gtgacaagct gcacgtggat cctgagaact tcaggg tgag tctatgggac   1260 gcttgatgtt ttctttcccc ttcttttcta tggttaagtt catgtcatag aaggggata   1320 agtaacaggg tacagtttag aatgggaaac agacgaatga ttgcatcagt gtggaagtct   1380
caggatcgtt ttagtttctt ttatttgctg ttcataacaa ttgttttctt ttgtttaatt   1440
cttgctttct ttttttttct tctccgcaat ttttactatt atacttaatg ccttaacatt   1500
gtgtataaca aaaggaaata tctctgagat acattaagta acttaaaaaa aaactttaca   1560
cagtctgcct agtacattac tatttggaat atatgtgtgc ttatttgcat attcataatc   1620
tccctacttt atttttcttt tttttaatt gatacataat cattatacat atttatgggt   1680
taaagtgtaa tgttttaata tgtgtacaca tattgaccaa atcagggtaa ttttgcattt   1740 gtaatttta aaaatgcttt cttcttttaa tatactttt tgtttatctt atttctaata   1800
ctttccctaa tctctttctt tcagggcaat aatgatacaa tgtatcatgc ctctttgcac   1860
cattctaaag aataacagtg ataatttctg ggttaaggca atagcaatat ctctgcatat   1920
aaatatttct gcatataaat tgtaactgat gtaagaggtt tcatattgct aatagcagct   1980
acaatccagc taccattctg cttttatttt atggttggga taaggctgga ttattctgag   2040
tccaagctag gcccttttgc taatcatgtt catacctctt atcttcctcc cacagctcct   2100
gggcaacgtg ctggtctgtg tgctggccca tcactttggc aaagaattca ccccaccagt   2160
gcaggctgcc tatcagaaag tggtggctgg tgtggctaat gccctggccc acaagtatca   2220
ctaagctcgc tttcttgctg tccaatttct attaaaggtt cctttgttcc ctaagtccaa   2280
ctactaaact gggggatatt atgaagggcc ttgagcatct ggattctgcc taataaaaaa   2340
catttatttt cattgcaatg atgtatttaa attattctg aatattttac taaaagga   2400 atgtgggagg tcagtgcatt taaaacataa agaaatgaag agctagttca aacctt       2456
```

<210> SEQ ID NO 37
<211> LENGTH: 2468
<212> TYPE: DNA
<213> ORGANISM: Artificial Sequence
<220> FEATURE:
<223> OTHER INFORMATION: hHBB-hLW-012 vector, ITRs not included

<400> SEQUENCE: 37

```
ttatttattt gtattttga ctgcattaag aggtctctag ttttttatct cttgtttccc     60
aaaacctaat aagtaactaa tgcacagagc acattgattt gtatttattc tattttaga   120
```

```
cataatttat tagcatgcat gagcaaatta agaaaaacaa caacaaatga atgcatatat      180
atgtatatgt atgtgtgtat atatacacac atatatatat atatttttc ttttcttacc      240 agaaggtttt aatccaaata aggagaagat atgcttagaa ccgaggtaga gttttcatcc      300
attctgtcct gtaagtattt tgcatattct ggagacgcag gaagagatcc atctacatat      360
cccaaagctg aattatggta gacaaaactc ttccactttt agtgcatcaa cttcttattt      420
gtgtaataag aaaattggga aaacgatctt caatatgctt accaagctgt gattccaaat      480
attacgtaaa tacacttgca aaggaggatg tttttagtag caatttgtac tgatggtatg      540
gggccaagag atatatctta gagggagggc tgagggtttg aagtccaact cctaagccag      600
tgccagaaga gccaaggaca ggtacggctg tcatcactta gacctcaccc tgtggagcca      660
caccctaggg ttggccaatc tactcccagg agcaggagg gcaggagcca gggctgggca      720
taaaagtcag ggcagagcca tctattgctt acatttgctt ctgacacaac tgtgttcact      780
agcaacctca aacagacacc atggtccacc tcacaccaga agaaaaaagt gctgtaacag      840
ctctctgggg aaaagtcaat gtcgacgagg taggggggga agctctcgga aggttggtat      900
caaggttaca agacaggact agtatcgatt ttaaggagac caatagaaac tgggcatgtg      960
gagacagaga agactcttgg gtttctgata ggcactgact ctctctgcct attggtctat     1020
tttcccaccc ttagactcct cgtcgtgtat ccatggacac aaagattttt cgaaagcttc     1080
ggagacctca gcacaccaga cgcagtaatg ggaaatccaa aagtcaaagc acacggaaaa     1140
aaggtcctgg gggctttctc tgacggactc gcacatctcg ataatctgaa aggaacattc     1200
gctaccctct ctgaactcca ttgcgataaa ctccatgtcg acccagaaaa ttttagagtg     1260
agtctatggg acgcttgatg ttttcttttcc ccttcttttc tatggttaag ttcatgtcat     1320
aggaagggga taagtaacag ggtacagttt agaatgggaa acagacgaat gattgcatca     1380
gtgtggaagt ctcaggatcg ttttagtttc ttttatttgc tgttcataac aattgttttc     1440
ttttgtttaa ttcttgcttt cttttttttt cttctccgca attttactaa ttatacttaa     1500
tgccttaaca ttgtgtataa caaaaggaaa tatctctgag atacattaag taacttaaaa     1560
aaaaacttta cacagtctgc ctagtacatt actatttgga atatatgtgt gcttatttgc     1620
atattcataa tctccctact ttattttctt ttattttttaa ttgatacata atcattatac     1680
atatttatgg gttaaagtgt aatgttttaa tatgtgtaca catattgacc aaatcagggt     1740
aattttgcat ttgtaatttt aaaaaatgct ttcttctttt aatatacttt tttgtttatc     1800
ttatttctaa tactttccct aatctctttc tttcagggca ataatgatac aatgtatcat     1860
gcctctttgc accattctaa agaataacag tgataatttc tgggttaagg caatagcaat     1920
atctctgcat ataaatattt ctgcatataa attgtaactg atgtaagagg tttcatattg     1980
ctaatagcag ctacaatcca gctaccattc tgcttttatt ttatggttgg gataaggctg     2040
gattattctg agtccaagct aggcccttt gctaatcatg ttcataccctc ttatcttcct     2100 cccacagctg ctcggaaatg tcctcgtgtg cgtcctcgct caccatttcg gaaaggagtt     2160
tacacctcct gtccaagcag cttaccaaaa ggtcgtcgca ggggtcgcaa acgctctcgc     2220
tcataaatac cattaggctc gctttcttgc tgtccaattt ctattaaagg ttcctttgtt     2280
ccctaagtcc aactactaaa ctgggggata ttatgaaggg ccttgagcat ctggattctg     2340
cctaataaaa aacatttatt ttcattgcaa tgatgtattt aaattatttc tgaatatttt     2400
actaaaaagg gaatgtggga ggtcagtgca tttaaaacat aaagaaatga agagctagtt     2460
caaacctt                                                             2468
```

<210> SEQ ID NO 38
<211> LENGTH: 2456
<212> TYPE: DNA
<213> ORGANISM: Artificial Sequence
<220> FEATURE:
<223> OTHER INFORMATION: hHBB-hLW-012 vector, ITRs not included, Linker removed

<400> SEQUENCE: 38

```
ttatttattt gtatttttga ctgcattaag aggtctctag tttttttatct cttgtttccc      60
aaaacctaat aagtaactaa tgcacagagc acattgattt gtatttattc tattttttaga    120
cataatttat tagcatgcat gagcaaatta agaaaaacaa caacaaatga atgcatatat    180
atgtatatgt atgtgtgtat atatacacac atatatatat atatttttttc ttttcttacc    240
agaaggtttt aatccaaata aggagaagat atgcttagaa ccgaggtaga gttttcatcc    300
attctgtcct gtaagtattt tgcatattct ggagacgcag gaagagatcc atctacatat    360
cccaaagctg aattatggta gacaaaactc ttccactttt agtgcatcaa cttcttattt    420
gtgtaataag aaaattggga aaacgatctt caatatgctt accaagctgt gattccaaat    480
attacgtaaa tacacttgca aaggaggatg ttttttagtag caatttgtac tgatggtatg    540
gggccaagag atatatctta gagggagggc tgagggtttg aagtccaact cctaagccag    600
tgccagaaga gccaaggaca ggtacggctg tcatcactta gacctcaccc tgtggagcca    660
caccctaggg ttggccaatc tactcccagg agcagggagg gcaggagcca gggctgggca    720
taaaagtcag ggcagagcca tctattgctt acatttgctt ctgacacaac tgtgttcact    780
agcaacctca aacagacacc atggtccacc tcacaccaga gaaaaaagt gctgtaacag    840
ctctctgggg aaaagtcaat gtcgacgagg taggggggga agctctcgga aggttggtat    900
caaggttaca agacaggttt aaggagacca atagaaactg gcatgtggga gacagagaag    960
actcttgggt ttctgatagg cactgactct ctctgcctat tggtctattt tcccacccctt   1020
agactcctcg tcgtgtatcc atggacacaa agatttttcg aaagcttcgg agacctcagc   1080
acaccagacg cagtaatggg aaatccaaaa gtcaaagcac acggaaaaaa ggtcctgggg   1140
gctttctctg acggactcgc acatctcgat aatctgaaag gaacattcgc taccctctct   1200
gaactccatt gcgataaact ccatgtcgac ccagaaaatt ttagagtgag tctatgggac   1260
gcttgatgtt ttcttttcccc ttcttttcta tggttaagtt catgtcatag aaggggata    1320
agtaacaggg tacagtttag aatgggaaac agacgaatga ttgcatcagt gtggaagtct   1380
caggatcgtt ttagtttctt ttatttgctg ttcataacaa ttgtttttctt ttgtttaatt   1440
cttgctttct ttttttttct tctccgcaat ttttactatt atacttaatg ccttaacatt   1500
gtgtataaca aaaggaaata tctctgagat acattaagta acttaaaaaa aaactttaca   1560
cagtctgcct agtacattac tatttggaat atatgtgtgc ttatttgcat attcataatc   1620
tccctacttt attttctttt attttttaatt gatacataat cattatacat atttatgggt   1680
taaagtgtaa tgttttaata tgtgtacaca tattgaccaa atcagggtaa ttttgcattt   1740
gtaattttaa aaaatgcttt cttcttttaa tatacttttt tgtttatctt atttctaata   1800
cttttccctaa tctctttctt tcagggcaat aatgatacaa tgtatcatgc ctctttgcac   1860
cattctaaag aataacagtg ataatttctg ggttaaggca atagcaatat ctctgcatat   1920
aaatatttct gcatataaat tgtaactgat gtaagaggtt tcatattgct aatagcagct   1980
acaatccagc taccattctg cttttatttt atggttggga taaggctgga ttattctgag   2040
```

```
tccaagctag gcccttttgc taatcatgtt catacctctt atcttcctcc cacagctgct    2100
cggaaatgtc ctcgtgtgcg tcctcgctca ccatttcgga aaggagttta cacctcctgt    2160
ccaagcagct taccaaaagg tcgtcgcagg ggtcgcaaac gctctcgctc ataaatacca    2220
ttaggctcgc tttcttgctg tccaatttct attaaaggtt cctttgttcc ctaagtccaa    2280
ctactaaact gggggatatt atgaaggggcc ttgagcatct ggattctgcc taataaaaaa    2340
catttatttt cattgcaatg atgtatttaa attatttctg aatattttac taaaagggga    2400
atgtgggagg tcagtgcatt taaaacataa agaaatgaag agctagttca aaccttt       2456
```

<210> SEQ ID NO 39
<211> LENGTH: 2321
<212> TYPE: DNA
<213> ORGANISM: Artificial Sequence
<220> FEATURE:
<223> OTHER INFORMATION: hHBB-hA-009 vector, ITRs not included

<400> SEQUENCE: 39

```
ttatttatttt gtatttttga ctgcattaag aggtctctag tttttatct cttgtttccc    60 aaaacctaat aagtaactaa tgcacagagc acattgattt gtatttattc tattttaga    120 cataatttat tagcatgcat gagcaaatta agaaaaacaa caacaaatga atgcatatat    180
atgtatatgt atgtgtgtat atatacacac atatatatat atatttttc ttttcttacc    240 agaaggtttt aatccaaata aggagaagat atgcttagaa ccgaggtaga gttttcatcc    300
attctgtcct gtaagtattt tgcatattct ggagacgcag gaagagatcc atctacatat    360
cccaaagctg aattatggta gacaaaactc ttccactttt agtgcatcaa cttcttattt    420
gtgtaataag aaaattggga aaacgatctt caatatgctt accaagctgt gattccaaat    480
attacgtaaa tacacttgca aaggaggatg tttttagtag caatttgtac tgatggtatg    540
gggccaagag atatatctta gagggaggggc tgagggtttg aagtccaact cctaagccag    600
tgccagaaga gccaaggaca ggtacggctg tcatcactta gacctcaccc tgtggagcca    660
caccctaggg ttggccaatc tactcccagg agcagggagg gcaggagcca gggctgggca    720
taaaagtcag ggcagagcca tctattgctt acatttgctt ctgacacaac tgtgttcact    780
agcaacctca aacagacacc atggtgcatc tgactcctga ggagaagtct gccgttactg    840
ccctgtgggg caaggtgaac gtggatgaag ttggtggtga ggccctgggc aggctgctgg    900
tggtctaccc ttggacccag aggttctttg agtcctttgg ggatctgtcc actcctgatg    960
ctgttatggg caaccctaag gtgaaggctc atggcaagaa agtgctcggt gcctttagtg    1020
atggcctggc tcacctggac aacctcaagg gcacctttgc cacactgagt gagctgcact    1080
gtgacaagct gcacgtggat cctgagaact tcaggctcct gggcaacgtg ctggtctgtg    1140
tgctggccca tcactttggc aaagaattca ccccaccagt gcaggctgcc tatcagaaag    1200
tggtggctgt gtggctaat gccctggccc acaagtatca ctaagaattc aaggcctctc    1260
gagcctctag aactatagtg agtcgtatta cgtagatcca gacatgataa gatacattga    1320
tgagtttgga caaaccacaa ctagaatgca gtgaaaaaaa tgctttattt gtgaaatttg    1380
tgatgctatt gctttatttg taaccattat aagctgcaat aaacaagtta acaacaacaa    1440
ttgcattcat tttatgtttc aggttcaggg ggaggtgtgg gaggtttttt aagcttcagc    1500
tgtgatcata acgttgagct cgtgcatctg actcctgagg agaagtctgc cgttactgcc    1560
ctgtggggca aggtgaacgt ggatgaagtt ggtggtgagg ccctgggcag gttggtatca    1620
```

| | |
|---|---|
| aggttacaag acaggtttaa ggagaccaat agaaactggg catgtggaga cagagaagac | 1680 |
| tcttgggttt ctgataggca ctgactctct ctgcctattg gtctatttc ccacccttag | 1740 |
| gctgctggtg gtctacccct ggacccagag gttctttgag tcctttgggg atctgtccac | 1800 |
| tcctgatgct gttatgggca accctaaggt gaaggctcat ggcaagaaag tgctcggtgc | 1860 |
| ctttagtgat ggcctggctc acctggacaa cctcaagggc acctttgcca cactgagtga | 1920 |
| gctgcactgt gacaagctgc acgtggatcc tgagaacttc agggtgagtc tatgggacgc | 1980 |
| ttgatgtttt ctttcccctt cttttctatg gttaagttca tgtcatagga aggggataag | 2040 |
| taacagggta cagtttagaa tgggaaacag acgaatgatt gcatcagtgt ggaagtctca | 2100 |
| ggatcgtttt agtttctttt atttgctgtt cataacaatt gttttctttt gtttaattct | 2160 |
| tgctttcttt ttttttcttc tccgcaattt ttactattat acttaatgcc ttaacattgt | 2220 |
| gtataacaaa aggaaatatc tctgagatac attaagtaac ttaaaaaaaa actttacaca | 2280 |
| gtctgcctag tacattacta tttggaatat atgtgtgctt a | 2321 |

<210> SEQ ID NO 40
<211> LENGTH: 2321
<212> TYPE: DNA
<213> ORGANISM: Artificial Sequence
<220> FEATURE:
<223> OTHER INFORMATION: hHBB-hAW-002 vector, ITRs not included

<400> SEQUENCE: 40

| | |
|---|---|
| ttatttattt gtatttttga ctgcattaag aggtctctag ttttttatct cttgtttccc | 60 |
| aaaacctaat aagtaactaa tgcacagagc acattgattt gtatttattc tatttttaga | 120 |
| cataatttat tagcatgcat gagcaaatta agaaaaacaa caacaaatga atgcatatat | 180 |
| atgtatatgt atgtgtgtat atatacacac atatatatat atatttttc ttttcttacc | 240 |
| agaaggtttt aatccaaata aggagaagat atgcttagaa ccgaggtaga gttttcatcc | 300 |
| attctgtcct gtaagtattt tgcatattct ggagacgcag gaagagatcc atctacatat | 360 |
| cccaaagctg aattatggta gacaaaactc ttccactttt agtgcatcaa cttcttattt | 420 |
| gtgtaataag aaaattggga aaacgatctt caatatgctt accaagctgt gattccaaat | 480 |
| attacgtaaa tacacttgca aaggaggatg ttttagtag caatttgtac tgatggtatg | 540 |
| gggccaagag atatatctta gagggagggc tgagggtttg aagtccaact cctaagccag | 600 |
| tgccagaaga gccaaggaca ggtacggctg tcatcactta gacctcaccc tgtggagcca | 660 |
| caccctaggg ttggccaatc tactcccagg agcaggagg gcaggagcca gggctgggca | 720 |
| taaaagtcag ggcagagcca tctattgctt acatttgctt ctgacacaac tgtgttcact | 780 |
| agcaaccctca aacagacacc atggtccacc tcacaccaga agaaaaaagt gctgtaacag | 840 |
| ctctctgggg aaaagtcaat gtcgacgagg tagggggga agctctcgga agactcctcg | 900 |
| tcgtgtatcc atggacacaa agattttcg aaagcttcgg agacctcagc acaccagacg | 960 |
| cagtaatggg aaatccaaaa gtcaaagcac acggaaaaaa ggtcctgggg gctttctctg | 1020 |
| acggactcgc acatctcgat aatctgaaag gaacattcgc taccctctct gaactccatt | 1080 |
| gcgataaact ccatgtcgac ccagaaaatt ttagactgct cggaaatgtc ctcgtgtgcg | 1140 |
| tcctcgctca ccatttcgga aaggagttta cacctcctgt ccaagcagct taccaaaagg | 1200 |
| tcgtcgcagg ggtcgcaaac gctctcgctc ataaatacca ttaggaattc aaggcctctc | 1260 |
| gagcctctag aactatagtg agtcgtatta cgtagatcca gacatgataa gatacattga | 1320 |
| tgagtttgga caaaccacaa ctagaatgca gtgaaaaaaa tgctttattt gtgaaatttg | 1380 |

```
tgatgctatt gctttatttg taaccattat aagctgcaat aaacaagtta acaacaacaa    1440
ttgcattcat tttatgtttc aggttcaggg ggaggtgtgg gaggtttttt aagcttcagc    1500
tgtgatcata acgttgagct cgtgcatctg actcctgagg agaagtctgc cgttactgcc    1560
ctgtggggca aggtgaacgt ggatgaagtt ggtggtgagg ccctgggcag gttggtatca    1620
aggttacaag acaggtttaa ggagaccaat agaaactggg catgtggaga cagagaagac    1680
tcttgggttt ctgataggca ctgactctct ctgcctattg gtctattttc ccacccttag    1740
gctgctggtg gtctacccct tggacccagag gttctttgag tcctttgggg atctgtccac    1800
tcctgatgct gttatgggca acctaaggt gaaggctcat ggcaagaaag tgctcggtgc    1860
ctttagtgat ggcctggctc acctggacaa cctcaagggc acctttgcca cactgagtga    1920
gctgcactgt gacaagctgc acgtggatcc tgagaacttc agggtgagtc tatgggacgc    1980
ttgatgtttt ctttcccctt cttttctatg gttaagttca tgtcatagga agggataag    2040 taacagggta cagtttagaa tgggaaacag acgaatgatt gcatcagtgt ggaagtctca    2100
ggatcgtttt agtttctttt atttgctgtt cataacaatt gttttctttt gtttaattct    2160
tgctttcttt ttttttcttc tccgcaattt ttactattat acttaatgcc ttaacattgt    2220
gtataacaaa aggaaatatc tctgagatac attaagtaac ttaaaaaaaa actttacaca    2280
gtctgcctag tacattacta tttggaatat atgtgtgctt a                        2321

<210> SEQ ID NO 41
<211> LENGTH: 2439
<212> TYPE: DNA
<213> ORGANISM: Artificial Sequence
<220> FEATURE:
<223> OTHER INFORMATION: hHBB-h1-010 vector, ITRs not included

<400> SEQUENCE: 41
caacaacaaa tgaatgcata tatatgtata tgtatgtgtg tatatataca cacatatata      60
tatatatttt ttcttttctt accagaaggt tttaatccaa ataaggagaa gatatgctta     120
gaaccgaggt agagttttca tccattctgt cctgtaagta ttttgcatat tctggagacg     180
caggaagaga tccatctaca tatcccaaag ctgaattatg gtagacaaaa ctcttccact     240
tttagtgcat caacttctta tttgtgtaat aagaaaattg ggaaaacgat cttcaatatg     300
cttaccaagc tgtgattcca aatattacgt aaatacactt gcaaggagg atgttttag      360 tagcaatttg tactgatggt atggggccaa gagatatatc ttagagggag ggctgagggt     420
ttgaagtcca actcctaagc cagtgccaga agagccaagg acaggtacgg ctgtcatcac     480
ttagacctca ccctgtggag ccacacccta gggttggcca atctactccc aggagcaggg     540
agggcaggag ccagggctgg gcataaaagt cagggcagag ccatctattg cttacatttg     600
cttctgacac aactgtgttc actagcaacc tcaaacagac accatggtgc atctgactcc     660
tgaggagaag tctgccgtta ctgccctgtg ggcaaggtg aacgtggatg aagttggtgg     720
tgaggccctg gcaggttgg tatcaaggtt acaagacagg tttaaggaga ccaatagaaa     780
ctgggcatgt ggagacagag aagcttctga cctcttctct tcctcccaca gggcggtacc     840
agatctggca gcgagaggg cagaggaagt cttctaacat gcggtgacgt ggaggagaat     900
cccggcccta ggggtaccat ggtgcatctg actcctgagg agaagtctgc cgttactgcc     960
ctgtggggca aggtgaacgt ggatgaagtt ggtggtgagg ccctgggcag gctgctggtg    1020
gtctacccct tggacccagag gttctttgag tcctttgggg atctgtccac tcctgatgct    1080
```

| | | |
|---|---|---|
| gttatgggca acccta aggt gaaggctcat ggcaagaaag tgctcggtgc ctttagtgat | 1140 | |
| ggcctggctc acctggacaa cctcaagggc acctttgcca cactgagtga gctgcactgt | 1200 | |
| gacaagctgc acgtggatcc tgagaacttc aggctcctgg gcaacgtgct ggtctgtgtg | 1260 | |
| ctggcccatc actttggcaa agaattcacc ccaccagtgc aggctgccta tcagaaagtg | 1320 | |
| gtggctggtg tggctaatgc cctggcccac aagtatcact aagaattcaa ggcctctcga | 1380 | |
| gcctctagaa ctatagtgag tcgtattacg tagatccaga catgataaga tacattgatg | 1440 | |
| agtttggaca aaccacaact agaatgcagt gaaaaaaatg ctttatttgt gaaatttgtg | 1500 | |
| atgctattgc tttatttgta accattataa gctgcaataa acaagttaac aacaacaatt | 1560 | |
| gcattcattt tatgtttcag gttcaggggg aggtgtggga ggttttttaa gcttcagctg | 1620 | |
| tgatcataac gttgagctca agactcttgg gtttctgata ggcactgact ctctctgcct | 1680 | |
| attggtctat tttcccaccc ttaggctgct ggtggtctac ccttggaccc agaggttctt | 1740 | |
| tgagtccttt ggggatctgt ccactcctga tgctgttatg ggcaacccta aggtgaaggc | 1800 | |
| tcatggcaag aaagtgctcg gtgcctttag tgatggcctg gctcacctgg acaacctcaa | 1860 | |
| gggcaccttt gccacactga gtgagctgca ctgtgacaag ctgcacgtgg atcctgagaa | 1920 | |
| cttcagggt agtctatggg acgcttgatg tttctttcc ccttcttttc tatggttaag | 1980 | |
| ttcatgtcat aggaagggga taagtaacag ggtacagttt agaatgggaa acagacgaat | 2040 | |
| gattgcatca gtgtggaagt ctcaggatcg ttttagtttc ttttatttgc tgttcataac | 2100 | |
| aattgttttc ttttgtttaa ttcttgcttt cttttttttt cttctccgca atttttacta | 2160 | |
| ttatacttaa tgccttaaca ttgtgtataa caaaaggaaa tatctctgag atacattaag | 2220 | |
| taacttaaaa aaaaacttta cacagtctgc ctagtacatt actatttgga atatatgtgt | 2280 | |
| gcttatttgc atattcataa tctccctact ttatttctt tattttaa ttgatacata | 2340 | |
| atcattatac atatttatgg gttaaagtgt aatgttttaa tatgtgtaca catattgacc | 2400 | |
| aaaatcaggt aattttgcat ttgtaatttt aaaaaatgc | 2439 | |

<210> SEQ ID NO 42
<211> LENGTH: 2439
<212> TYPE: DNA
<213> ORGANISM: Artificial Sequence
<220> FEATURE:
<223> OTHER INFORMATION: hHBB-h1W-008 vector, ITRs not included

<400> SEQUENCE: 42

| | | |
|---|---|---|
| caacaacaaa tgaatgcata tatatgtata tgtatgtgtg tatatataca cacatatata | 60 | |
| tatatatttt ttcttttctt accagaaggt tttaatccaa ataaggagaa gatatgctta | 120 | |
| gaaccgaggt agagttttca tccattctgt cctgtaagta ttttgcatat tctggagacg | 180 | |
| caggaagaga tccatctaca tatcccaaag ctgaattatg gtagacaaaa ctcttccact | 240 | |
| tttagtgcat caacttctta tttgtgtaat aagaaaattg ggaaaacgat cttcaatatg | 300 | |
| cttaccaagc tgtgattcca atatattacgt aaatacactt gcaaggagg atgtttttag | 360 | |
| tagcaatttg tactgatggt atggggccaa gagatatatc ttagagggag ggctgagggt | 420 | |
| ttgaagtcca actcctaagc cagtgccaga agagccaagg acaggtacgg ctgtcatcac | 480 | |
| ttagacctca ccctgtggag ccacacccta gggttggcca atctactccc aggagcaggg | 540 | |
| agggcaggag ccagggctgg gcataaaagt cagggcagag ccatctattg cttcatttg | 600 | |
| cttctgacac aactgtgttc actagcaacc tcaaacagac accatggtgc atctgactcc | 660 | |
| tgaggagaag tctgccgtta ctgccctgtg gggcaaggtg aacgtggatg aagttggtgg | 720 | |

```
tgaggccctg ggcaggttgg tatcaaggtt acaagacagg tttaaggaga ccaatagaaa      780
ctgggcatgt ggagacagag aagcttctga cctcttctct tcctcccaca gggcggtacc      840
agatctggca gcggagaggg cagaggaagt cttctaacat gcggtgacgt ggaggagaat      900
cccggcccta ggggtaccat ggtccacctc acaccagaag aaaaaagtgc tgtaacagct      960
ctctggggaa aagtcaatgt cgacgaggta ggggggaag ctctcggaag actcctcgtc      1020
gtgtatccat ggacacaaag atttttcgaa agcttcggag acctcagcac accagacgca     1080
gtaatgggaa atccaaaagt caaagcacac ggaaaaaagg tcctgggggc tttctctgac     1140
ggactcgcac atctcgataa tctgaaagga acattcgcta ccctctctga actccattgc     1200
gataaactcc atgtcgaccc agaaaatttt agactgctcg gaaatgtcct cgtgtgcgtc     1260
ctcgctcacc atttcggaaa ggagtttaca cctcctgtcc aagcagctta ccaaaaggtc     1320
gtcgcagggg tcgcaaacgc tctcgctcat aaataccatt aggaattcaa ggcctctcga     1380
gcctctagaa ctatagtgag tcgtattacg tagatccaga catgataaga tacattgatg     1440
agtttggaca aaccacaact agaatgcagt gaaaaaaatg ctttatttgt gaaatttgtg     1500
atgctattgc tttatttgta accattataa gctgcaataa acaagttaac aacaacaatt     1560
gcattcattt tatgtttcag gttcaggggg aggtgtggga ggttttttaa gcttcagctg     1620
tgatcataac gttgagctca agactcttgg gtttctgata ggcactgact ctctctgcct     1680
attggtctat tttcccaccc ttaggctgct ggtggtctac ccttggaccc agaggttctt     1740
tgagtccttt ggggatctgt ccactcctga tgctgttatg gcaaccccta aggtgaaggc     1800
tcatggcaag aaagtgctcg gtgcctttag tgatggcctg gctcacctgg acaacctcaa     1860
gggcaccttt gccacactga gtgagctgca ctgtgacaag ctgcacgtgg atcctgagaa     1920
cttcagggtg agtctatggg acgcttgatg ttttctttcc ccttctttc tatggttaag     1980 ttcatgtcat aggaagggga taagtaacag ggtacagttt agaatgggaa acagacgaat     2040
gattgcatca gtgtggaagt ctcaggatcg ttttagtttc ttttatttgc tgttcataac     2100
aattgttttc ttttgtttaa ttcttgcttt cttttttttt cttctccgca attttttacta    2160 ttatacttaa tgccttaaca ttgtgtataa caaaaggaaa tatctctgag atacattaag     2220
taacttaaaa aaaaacttta cacagtctgc ctagtacatt actatttgga atatatgtgt     2280
gcttatttgc atattcataa tctccctact ttattttctt ttatttttaa ttgatacata     2340
atcattatac atatttatgg gttaaagtgt aatgttttaa tatgtgtaca catattgacc     2400
aaatcagggt aattttgcat ttgtaatttt aaaaatgc                              2439
```

<210> SEQ ID NO 43
<211> LENGTH: 92
<212> TYPE: DNA
<213> ORGANISM: Artificial Sequence
<220> FEATURE:
<223> OTHER INFORMATION: hHBB coding sequence in exon 1 with silent
      codon alterations

<400> SEQUENCE: 43

```
atggtccacc tcacaccaga agaaaaaagt gctgtaacag ctctctgggg aaaagtcaat        60
gtcgacgagg taggggggga agctctcgga ag                                     92
```

<210> SEQ ID NO 44
<211> LENGTH: 223
<212> TYPE: DNA
<213> ORGANISM: Artificial Sequence

```
<220> FEATURE:
<223> OTHER INFORMATION: hHBB coding sequence in exon 2 with silent
      codon alterations

<400> SEQUENCE: 44
actcctcgtc gtgtatccat ggacacaaag attttcgaa agcttcggag acctcagcac    60
accagacgca gtaatgggaa atccaaaagt caaagcacac ggaaaaaagg tcctgggggc   120
tttctctgac ggactcgcac atctcgataa tctgaaagga acattcgcta ccctctctga   180
actccattgc gataaactcc atgtcgaccc agaaaatttt aga                     223

<210> SEQ ID NO 45
<211> LENGTH: 129
<212> TYPE: DNA
<213> ORGANISM: Artificial Sequence
<220> FEATURE:
<223> OTHER INFORMATION: hHBB coding sequence in exon 3 with silent
      codon alterations

<400> SEQUENCE: 45
ctgctcggaa atgtcctcgt gtgcgtcctc gctcaccatt tcggaaagga gtttacacct    60
cctgtccaag cagcttacca aaaggtcgtc gcaggggtcg caaacgctct cgctcataaa   120
taccattag                                                           129

<210> SEQ ID NO 46
<211> LENGTH: 352
<212> TYPE: DNA
<213> ORGANISM: Artificial Sequence
<220> FEATURE:
<223> OTHER INFORMATION: hHBB coding sequence from second codon to stop
      codon, with silent codon alterations

<400> SEQUENCE: 46
actcctcgtc gtgtatccat ggacacaaag attttcgaa agcttcggag acctcagcac    60
accagacgca gtaatgggaa atccaaaagt caaagcacac ggaaaaaagg tcctgggggc   120
tttctctgac ggactcgcac atctcgataa tctgaaagga acattcgcta ccctctctga   180
actccattgc gataaactcc atgtcgaccc agaaaatttt agactgctcg gaaatgtcct   240
cgtgtgcgtc ctcgctcacc atttcggaaa ggagtttaca cctcctgtcc aagcagctta   300
ccaaaaggtc gtcgcagggg tcgcaaacgc tctcgctcat aaataccatt ag           352

<210> SEQ ID NO 47
<211> LENGTH: 441
<212> TYPE: DNA
<213> ORGANISM: Artificial Sequence
<220> FEATURE:
<223> OTHER INFORMATION: hHBB coding sequence from start codon to stop
      codon, with silent codon alterations

<400> SEQUENCE: 47
gtccacctca caccagaaga aaaagtgct gtaacagctc tctggggaaa agtcaatgtc    60
gacgaggtag gggggaagc tctcggaaga ctcctcgtcg tgtatccatg gacacaaaga   120 ttttcgaaa gcttcggaga cctcagcaca ccagacgcag taatgggaaa tccaaaagtc   180
aaagcacacg gaaaaaaggt cctgggggct ttctctgacg gactcgcaca tctcgataat   240
ctgaaaggaa cattcgctac cctctctgaa ctccattgcg ataaactcca tgtcgaccca   300
gaaaatttta gactgctcgg aaatgtcctc gtgtgcgtcc tcgctcacca tttcggaaag   360
gagtttacac ctcctgtcca agcagcttac caaaaggtcg tcgcaggggt cgcaaacgct   420
```

```
ctcgctcata ataccatta g                                               441

<210> SEQ ID NO 48
<211> LENGTH: 146
<212> TYPE: PRT
<213> ORGANISM: Homo sapiens

<400> SEQUENCE: 48

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 49
<211> LENGTH: 8
<212> TYPE: PRT
<213> ORGANISM: Artificial Sequence
<220> FEATURE:
<223> OTHER INFORMATION: 2A peptide consensus motif
<220> FEATURE:
<221> NAME/KEY: VARIANT
<222> LOCATION: (1)..(1)
<223> OTHER INFORMATION: X is Asp or Gly.
<220> FEATURE:
<221> NAME/KEY: VARIANT
<222> LOCATION: (2)..(2)
<223> OTHER INFORMATION: X is Val or Ile.
<220> FEATURE:
<221> NAME/KEY: VARIANT
<222> LOCATION: (4)..(4)
<223> OTHER INFORMATION: X is any amino acid.

<400> SEQUENCE: 49

Xaa Xaa Glu Xaa Asn Pro Gly Pro
1               5

<210> SEQ ID NO 50
<211> LENGTH: 45
<212> TYPE: DNA
<213> ORGANISM: Homo sapiens

<400> SEQUENCE: 50 agggtggag tcgtgacgtg ccaaatcaag cctctacttg aatcc                     45

<210> SEQ ID NO 51
<211> LENGTH: 54
<212> TYPE: DNA
```

```
<213> ORGANISM: Homo sapiens

<400> SEQUENCE: 51
aatgattaac cgccatgct acttatctac gtaaacctag gctccagata gcca        54

<210> SEQ ID NO 52
<211> LENGTH: 18
<212> TYPE: DNA
<213> ORGANISM: Homo sapiens

<400> SEQUENCE: 52
ggaagcagaa ctctgcac                                              18

<210> SEQ ID NO 53
<211> LENGTH: 27
<212> TYPE: DNA
<213> ORGANISM: Homo sapiens

<400> SEQUENCE: 53
gcattaagag gtctctagtt ttttatc                                    27

<210> SEQ ID NO 54
<211> LENGTH: 26
<212> TYPE: DNA
<213> ORGANISM: Homo sapiens

<400> SEQUENCE: 54
gatggtatgg ggccaagaga tatatc                                     26

<210> SEQ ID NO 55
<211> LENGTH: 20
<212> TYPE: DNA
<213> ORGANISM: Homo sapiens

<400> SEQUENCE: 55
gtctaccctt ggacccagag                                            20

<210> SEQ ID NO 56
<211> LENGTH: 26
<212> TYPE: DNA
<213> ORGANISM: Homo sapiens

<400> SEQUENCE: 56
cagtctgcct agtacattac tatttg                                     26

<210> SEQ ID NO 57
<211> LENGTH: 23
<212> TYPE: DNA
<213> ORGANISM: Homo sapiens

<400> SEQUENCE: 57
catgttcata cctcttatct tcc                                        23

<210> SEQ ID NO 58
<211> LENGTH: 22
<212> TYPE: DNA
<213> ORGANISM: Homo sapiens

<400> SEQUENCE: 58
gcaaacagct aatgcacatt gg                                         22

<210> SEQ ID NO 59
<211> LENGTH: 22
```

```
<212> TYPE: DNA
<213> ORGANISM: Homo sapiens

<400> SEQUENCE: 59
cagaatccag atgctcaagg cc                                            22

<210> SEQ ID NO 60
<211> LENGTH: 20
<212> TYPE: DNA
<213> ORGANISM: Homo sapiens

<400> SEQUENCE: 60
ccctgatttg gtcaatatgt                                               20

<210> SEQ ID NO 61
<211> LENGTH: 23
<212> TYPE: DNA
<213> ORGANISM: Homo sapiens

<400> SEQUENCE: 61
catcaagcgt cccatagact cac                                           23

<210> SEQ ID NO 62
<211> LENGTH: 21
<212> TYPE: DNA
<213> ORGANISM: Homo sapiens

<400> SEQUENCE: 62
gcagacttct cctcaggagt c                                             21

<210> SEQ ID NO 63
<211> LENGTH: 25
<212> TYPE: DNA
<213> ORGANISM: Homo sapiens

<400> SEQUENCE: 63
cttacaggac agaatggatg aaaac                                         25

<210> SEQ ID NO 64
<211> LENGTH: 22
<212> TYPE: DNA
<213> ORGANISM: Homo sapiens

<400> SEQUENCE: 64
gaaaaggtct tctacttggc tc                                            22

<210> SEQ ID NO 65
<211> LENGTH: 20
<212> TYPE: DNA
<213> ORGANISM: Homo sapiens

<400> SEQUENCE: 65
ggttaaccaa aagaaactgg                                               20

<210> SEQ ID NO 66
<211> LENGTH: 22
<212> TYPE: DNA
<213> ORGANISM: Homo sapiens

<400> SEQUENCE: 66
tgcagattag tccaggcaga aa                                            22

<210> SEQ ID NO 67
```

-continued

<210> SEQ ID NO 67
<211> LENGTH: 25
<212> TYPE: DNA
<213> ORGANISM: Homo sapiens

<400> SEQUENCE: 67
gggtaatcag tggtgtcaaa tagga                                              25

<210> SEQ ID NO 68
<211> LENGTH: 20
<212> TYPE: DNA
<213> ORGANISM: Homo sapiens

<400> SEQUENCE: 68
agttagatgt ccccagttaa                                                    20

<210> SEQ ID NO 69
<211> LENGTH: 29
<212> TYPE: DNA
<213> ORGANISM: Artificial Sequence
<220> FEATURE:
<223> OTHER INFORMATION: HBB2MTI100 Forward Primer

<400> SEQUENCE: 69
ctattggtct ccttaaaatc gatactagt                                          29

<210> SEQ ID NO 70
<211> LENGTH: 24
<212> TYPE: DNA
<213> ORGANISM: Homo sapiens

<400> SEQUENCE: 70
atattcaaac ttccgcagaa cact                                               24

<210> SEQ ID NO 71
<211> LENGTH: 18
<212> TYPE: PRT
<213> ORGANISM: Artificial Sequence
<220> FEATURE:
<223> OTHER INFORMATION: T2A peptide

<400> SEQUENCE: 71

Glu Gly Arg Gly Ser Leu Leu Thr Cys Gly Asp Val Glu Glu Asn Pro
1               5                   10                  15

Gly Pro

<210> SEQ ID NO 72
<211> LENGTH: 54
<212> TYPE: DNA
<213> ORGANISM: Artificial Sequence
<220> FEATURE:
<223> OTHER INFORMATION: T2A element

<400> SEQUENCE: 72
gagggcagag gaagtcttct aacatgcggt gacgtggagg agaatcccgg ccct              54

<210> SEQ ID NO 73
<211> LENGTH: 19
<212> TYPE: PRT
<213> ORGANISM: Artificial Sequence
<220> FEATURE:
<223> OTHER INFORMATION: P2A peptide

<400> SEQUENCE: 73

Ala Thr Asn Phe Ser Leu Leu Lys Gln Ala Gly Asp Val Glu Glu Asn
1               5                   10                  15

Pro Gly Pro

<210> SEQ ID NO 74
<211> LENGTH: 57
<212> TYPE: DNA
<213> ORGANISM: Artificial Sequence
<220> FEATURE:
<223> OTHER INFORMATION: P2A element

<400> SEQUENCE: 74
gctactaact tcagcctgct gaagcaggct ggagacgtgg aggagaaccc tggacct      57

<210> SEQ ID NO 75
<211> LENGTH: 9
<212> TYPE: DNA
<213> ORGANISM: Artificial Sequence
<220> FEATURE:
<223> OTHER INFORMATION: GSG coding sequence

<400> SEQUENCE: 75 ggcagcgga                                                            9

<210> SEQ ID NO 76
<211> LENGTH: 198
<212> TYPE: DNA
<213> ORGANISM: Artificial Sequence
<220> FEATURE:
<223> OTHER INFORMATION: SV40 polyA signal

<400> SEQUENCE: 76
ttaaaaaacc tcccacacct cccccctgaac ctgaaacata aaatgaatgc aattgttgtt   60
gttaacttgt ttattgcagc ttataatggt tacaaataaa gcaatagcat cacaaatttc  120
acaaataaag cattttttc actgcattct agttgtggtt tgtccaaact catcaatgta  180
tcttatcatg tctggatc                                                198

<210> SEQ ID NO 77
<211> LENGTH: 198
<212> TYPE: DNA
<213> ORGANISM: Artificial Sequence
<220> FEATURE:
<223> OTHER INFORMATION: SV40 polyA signal

<400> SEQUENCE: 77
gatccagaca tgataagata cattgatgag tttggacaaa ccacaactag aatgcagtga   60
aaaaaatgct ttatttgtga aatttgtgat gctattgctt tatttgtaac cattataagc  120
tgcaataaac aagttaacaa caacaattgc attcatttta tgtttcaggt tcagggggag  180
gtgtgggagg ttttttaa                                                198

<210> SEQ ID NO 78
<211> LENGTH: 122
<212> TYPE: DNA
<213> ORGANISM: Artificial Sequence
<220> FEATURE:
<223> OTHER INFORMATION: SV40 polyA signal

<400> SEQUENCE: 78
aacttgttta ttgcagctta taatggttac aaataaagca atagcatcac aaatttcaca   60
aataaagcat ttttttcact gcattctagt tgtggtttgt ccaaactcat caatgtatct  120
ta                                                                 122

```
<210> SEQ ID NO 79
<211> LENGTH: 122
<212> TYPE: DNA
<213> ORGANISM: Artificial Sequence
<220> FEATURE:
<223> OTHER INFORMATION: SV40 polyA signal

<400> SEQUENCE: 79
taagatacat tgatgagttt ggacaaacca caactagaat gcagtgaaaa aaatgcttta      60
tttgtgaaat ttgtgatgct attgctttat ttgtaaccat tataagctgc aataaacaag    120
tt                                                                   122

<210> SEQ ID NO 80
<211> LENGTH: 12
<212> TYPE: DNA
<213> ORGANISM: Artificial Sequence
<220> FEATURE:
<223> OTHER INFORMATION: TI RE Linker

<400> SEQUENCE: 80
actagtatcg at                                                         12

<210> SEQ ID NO 81
<211> LENGTH: 20
<212> TYPE: DNA
<213> ORGANISM: Artificial Sequence
<220> FEATURE:
<223> OTHER INFORMATION: HBB L NGS S1

<400> SEQUENCE: 81
cctctgggtc caagggtaga                                                 20

<210> SEQ ID NO 82
<211> LENGTH: 87
<212> TYPE: DNA
<213> ORGANISM: Artificial Sequence
<220> FEATURE:
<223> OTHER INFORMATION: HBB NGS Nest 5 Forward Adapter 1

<400> SEQUENCE: 82
aatgatacgg cgaccaccga gatctacaca agtagagtct ttccctacac gacgctcttc     60
cgatctgggc ataaaagtca gggcaga                                         87

<210> SEQ ID NO 83
<211> LENGTH: 88
<212> TYPE: DNA
<213> ORGANISM: Artificial Sequence
<220> FEATURE:
<223> OTHER INFORMATION: HBB NGS Nest 5 Forward Adapter 2

<400> SEQUENCE: 83
aatgatacgg cgaccaccga gatctacacc atgcttatct ttccctacac gacgctcttc     60
cgatcttggg cataaaagtc agggcaga                                        88

<210> SEQ ID NO 84
<211> LENGTH: 89
<212> TYPE: DNA
<213> ORGANISM: Artificial Sequence
<220> FEATURE:
<223> OTHER INFORMATION: HBB NGS Nest 5 Forward Adapter 3

<400> SEQUENCE: 84
aatgatacgg cgaccaccga gatctacacg cacatcttct ttccctacac gacgctcttc     60
```
cgatctatgg gcataaaagt cagggcaga                                       89

<210> SEQ ID NO 85
<211> LENGTH: 90
<212> TYPE: DNA
<213> ORGANISM: Artificial Sequence
<220> FEATURE:
<223> OTHER INFORMATION: HBB NGS Nest 5 Forward Adapter 4

<400> SEQUENCE: 85
aatgatacgg cgaccaccga gatctacact gctcgactct ttccctacac gacgctcttc    60
cgatctgatg ggcataaaag tcagggcaga                                     90

<210> SEQ ID NO 86
<211> LENGTH: 88
<212> TYPE: DNA
<213> ORGANISM: Artificial Sequence
<220> FEATURE:
<223> OTHER INFORMATION: HBB NGS Nest 5 Reverse Adapter 1

<400> SEQUENCE: 86
caagcagaag acggcatacg agatcatgat cggtgactgg agttcagacg tgtgctcttc    60
cgatctgtct ccacatgccc agtttcta                                       88

<210> SEQ ID NO 87
<211> LENGTH: 89
<212> TYPE: DNA
<213> ORGANISM: Artificial Sequence
<220> FEATURE:
<223> OTHER INFORMATION: HBB NGS Nest 5 Reverse Adapter 2

<400> SEQUENCE: 87
caagcagaag acggcatacg agataggatc tagtgactgg agttcagacg tgtgctcttc    60
cgatcttgtc tccacatgcc cagtttcta                                      89

<210> SEQ ID NO 88
<211> LENGTH: 90
<212> TYPE: DNA
<213> ORGANISM: Artificial Sequence
<220> FEATURE:
<223> OTHER INFORMATION: HBB NGS Nest 5 Reverse Adapter 3

<400> SEQUENCE: 88
caagcagaag acggcatacg agatgacagt aagtgactgg agttcagacg tgtgctcttc    60
cgatctatgt ctccacatgc ccagtttcta                                     90

<210> SEQ ID NO 89
<211> LENGTH: 90
<212> TYPE: DNA
<213> ORGANISM: Artificial Sequence
<220> FEATURE:
<223> OTHER INFORMATION: HBB NGS Nest 5 Reverse Adapter 4

<400> SEQUENCE: 89
caagcagaag acggcatacg agatcctatg ccgtgactgg agttcagacg tgtgctcttc    60
cgatctgagt ctccacatgc ccagtttcta                                     90

<210> SEQ ID NO 90
<211> LENGTH: 19
<212> TYPE: DNA
<213> ORGANISM: Artificial Sequence
<220> FEATURE:

<223> OTHER INFORMATION: AAVS1_Genomic, forward primer

<400> SEQUENCE: 90
gcgttagagg gcagagttc                                            19

<210> SEQ ID NO 91
<211> LENGTH: 19
<212> TYPE: DNA
<213> ORGANISM: Artificial Sequence
<220> FEATURE:
<223> OTHER INFORMATION: AAVS1_Genomic, reverse primer

<400> SEQUENCE: 91
agctcccata gctcagtct                                            19

<210> SEQ ID NO 92
<211> LENGTH: 23
<212> TYPE: DNA
<213> ORGANISM: Artificial Sequence
<220> FEATURE:
<223> OTHER INFORMATION: AAVS1_Genomic, probe

<400> SEQUENCE: 92
cattgtcact ttgcgctgcc ctc                                       23

<210> SEQ ID NO 93
<211> LENGTH: 22
<212> TYPE: DNA
<213> ORGANISM: Artificial Sequence
<220> FEATURE:
<223> OTHER INFORMATION: AAVS1_FP forward primer

<400> SEQUENCE: 93
gcaatagcat cacaaatttc ac                                        22

<210> SEQ ID NO 94
<211> LENGTH: 25
<212> TYPE: DNA
<213> ORGANISM: Artificial Sequence
<220> FEATURE:
<223> OTHER INFORMATION: AAVS1_FP, reverse primer

<400> SEQUENCE: 94
gatccagaca tgataagata cattg                                     25

<210> SEQ ID NO 95
<211> LENGTH: 28
<212> TYPE: DNA
<213> ORGANISM: Artificial Sequence
<220> FEATURE:
<223> OTHER INFORMATION: AAVS1_FP, probe

<400> SEQUENCE: 95
tcactgcatt ctagttgtgg tttgtcca                                  28

<210> SEQ ID NO 96
<211> LENGTH: 25
<212> TYPE: DNA
<213> ORGANISM: Artificial Sequence
<220> FEATURE:
<223> OTHER INFORMATION: SA-2A-FM1

<400> SEQUENCE: 96
gcttctgacc tcttctcttc ctccc                                     25

```
<210> SEQ ID NO 97
<211> LENGTH: 21
<212> TYPE: DNA
<213> ORGANISM: Artificial Sequence
<220> FEATURE:
<223> OTHER INFORMATION: SA-2A-FM2

<400> SEQUENCE: 97
gcggtgacgt ggaggagaat c                                              21

<210> SEQ ID NO 98
<211> LENGTH: 24
<212> TYPE: DNA
<213> ORGANISM: Artificial Sequence
<220> FEATURE:
<223> OTHER INFORMATION: HBB-Out-RM2

<400> SEQUENCE: 98
gcagaatggt agctggattg tagc                                           24

<210> SEQ ID NO 99
<211> LENGTH: 444
<212> TYPE: DNA
<213> ORGANISM: Artificial Sequence
<220> FEATURE:
<223> OTHER INFORMATION: silently altered HBB coding sequence

<400> SEQUENCE: 99
atggtgcacc tcaccccaga agagaagtct gctgtgacag ctctctgggg aaaagtaaat      60
gtggatgagg tgggagggga ggccctagga aggcttcttg ttgtctaccc ctggacacag     120
agattctttg aatcctttgg ggacctgagc actcctgatg cagtgatggg caaccccaaa    180
gtcaaagctc atgggaagaa ggttttggga gccttctcag atggcctggc tcacctggac    240
aacctgaagg gcacctttgc caccctgtct gagctgcact gtgacaagct gcatgtggac    300
cctgagaact tcaggctcct gggcaatgtt ctggtatgtg tgttagcaca ccattttggc    360
aaggaattca cccctccagt gcaggctgcc taccagaaag tggtggcagg tgtggccaat    420
gccctggccc acaaatatca ctga                                           444

<210> SEQ ID NO 100
<211> LENGTH: 441
<212> TYPE: DNA
<213> ORGANISM: Artificial Sequence
<220> FEATURE:
<223> OTHER INFORMATION: silently altered HBB coding sequence without
      start codon

<400> SEQUENCE: 100
gtgcacctca ccccagaaga gaagtctgct gtgacagctc tctggggaaa agtaaatgtg      60
gatgaggtgg gaggggaggc cctaggaagg cttcttgttg tctacccctg gacacagaga    120
ttctttgaat cctttgggga cctgagcact cctgatgcag tgatgggcaa ccccaaagtc    180
aaagctcatg ggaagaaggt tttgggagcc ttctcagatg gcctggctca cctggacaac    240
ctgaagggca cctttgccac cctgtctgag ctgcactgtg acaagctgca tgtggaccct    300
gagaacttca ggctcctggg caatgttctg gtatgtgtgt tagcacacca ttttggcaag    360
gaattcaccc ctccagtgca ggctgcctac cagaaagtgg tggcaggtgt ggccaatgcc    420
ctggcccaca aatatcactg a                                              441

<210> SEQ ID NO 101
<211> LENGTH: 489
```

```
<212> TYPE: DNA
<213> ORGANISM: Homo sapiens

<400> SEQUENCE: 101
ttgcatttgt aattttaaaa aatgctttct tcttttaata tacttttttg tttatcttat      60
ttctaatact ttccctaatc tctttctttc agggcaataa tgatacaatg tatcatgcct     120
ctttgcacca ttctaaagaa taacagtgat aatttctggg ttaaggcaat agcaatatct     180
ctgcatataa atatttctgc atataaattg taactgatgt aagaggtttc atattgctaa     240
tagcagctac aatccagcta ccattctgct tttatttat ggttgggata aggctggatt      300
attctgagtc caagctaggc ccttttgcta atcatgttca tacctcttat cttcctccca     360
cagctcctgg gcaacgtgct ggtctgtgtg ctggcccatc actttggcaa agaattcacc     420
ccaccagtgc aggctgccta tcagaaagtg gtggctggtg tggctaatgc cctggcccac     480
aagtatcac                                                            489

<210> SEQ ID NO 102
<211> LENGTH: 1134
<212> TYPE: DNA
<213> ORGANISM: Homo sapiens

<400> SEQUENCE: 102
gctcgctttc ttgctgtcca atttctatta aaggttcctt tgttccctaa gtccaactac      60
taaactgggg gatattatga agggccttga gcatctggat tctgcctaat aaaaaacatt     120
tattttcatt gcaatgatgt atttaaatta tttctgaata ttttactaaa aagggaatgt     180
gggaggtcag tgcatttaaa acataaagaa atgaagagct agttcaaacc ttgggaaaat     240
acactatatc ttaaactcca tgaaagaagg tgaggctgca aacagctaat gcacattggc     300
aacagcccct gatgcatatg ccttattcat ccctcagaaa aggattcaag tagaggcttg     360
atttggaggt taaagttttg ctatgctgta ttttacatta cttattgttt tagctgtcct     420
catgaatgtc ttttcactac ccatttgctt atcctgcatc tctcagcctt gactccactc     480
agttctcttg cttagagata ccaccttttcc cctgaagtgt tccttccatg tttttacggcg    540 agatggtttc tcctcgcctg gccactcagc cttagttgtc tctgttgtct tatagaggtc     600
tacttgaaga aggaaaaaca ggggtcatgg tttgactgtc ctgtgagccc ttcttccctg     660
cctcccccac tcacagtgac ccggaatctg cagtgctagt ctcccggaac tatcactctt     720
tcacagtctg ctttggaagg actgggctta gtatgaaaag ttaggactga aagaatttg      780 aaaggcggct ttttgtagct tgatattcac tactgtctta ttaccctgtc ataggcccac     840
cccaaatgga agtcccattc ttcctcagga tgtttaagat tagcattcag gaagagatca     900
gaggtctgct ggctccctta tcatgtccct tatggtgctt ctggctctgc agttattagc     960
atagtgttac catcaaccac cttaacttca ttttttcttat tcaataccta ggtaggtaga    1020
tgctagattc tggaaataaa atatgagtct caagtggtcc ttgtcctctc tcccagtcaa    1080
attctgaatc tagttggcaa gattctgaaa tcaaggcata taatcagtaa taag           1134

<210> SEQ ID NO 103
<211> LENGTH: 1626
<212> TYPE: DNA
<213> ORGANISM: Homo sapiens

<400> SEQUENCE: 103
ttgcatttgt aattttaaaa aatgctttct tcttttaata tacttttttg tttatcttat      60
```

```
ttctaatact ttccctaatc tctttctttc agggcaataa tgatacaatg tatcatgcct    120
ctttgcacca ttctaaagaa taacagtgat aatttctggg ttaaggcaat agcaatatct    180
ctgcatataa atatttctgc atataaattg taactgatgt aagaggtttc atattgctaa    240
tagcagctac aatccagcta ccattctgct tttattttat ggttgggata aggctggatt    300
attctgagtc caagctaggc ccttttgcta atcatgttca tacctcttat cttcctccca    360
cagctcctgg gcaacgtgct ggtctgtgtg ctggcccatc actttggcaa agaattcacc    420
ccaccagtgc aggctgccta tcagaaagtg gtggctggtg tggctaatgc cctggcccac    480
aagtatcact aagctcgctt tcttgctgtc aatttctat taaaggttcc tttgttccct    540
aagtccaact actaaactgg gggatattat gaagggcctt gagcatctgg attctgccta    600
ataaaaaaca tttattttca ttgcaatgat gtatttaaat tatttctgaa tattttacta    660
aaaagggaat gtgggaggtc agtgcattta aaacataaag aaatgaagag ctagttcaaa    720
ccttgggaaa atacactata tcttaaactc catgaaagaa ggtgaggctg caaacagcta    780
atgcacattg gcaacagccc ctgatgcata tgccttattc atccctcaga aaaggattca    840
agtagaggct tgatttggag gttaaagttt tgctatgctg tattttacat tacttattgt    900
tttagctgtc ctcatgaatg tcttttcact acccatttgc ttatcctgca tctctcagcc    960
ttgactccac tcagttctct tgcttagaga taccacctt ccctgaagt gttccttcca    1020 tgttttacgg cgagatggtt ctcctcgcc tggccactca gccttagttg tctctgttgt    1080
cttatagagg tctacttgaa gaaggaaaaa caggggtcat ggtttgactg tcctgtgagc    1140
ccttcttccc tgcctccccc actcacagtg acccggaatc tgcagtgcta gtctcccgga    1200
actatcactc tttcacagtc tgctttggaa ggactgggct tagtatgaaa agttaggact    1260
gagaagaatt tgaaaggcgg cttttttgtag cttgatattc actactgtct tattaccctg    1320
tcataggccc accccaaatg gaagtcccat tcttcctcag gatgtttaag attagcattc    1380
aggaagagat cagaggtctg ctggctccct tatcatgtcc cttatggtgc ttctggctct    1440
gcagttatta gcatagtgtt accatcaacc accttaactt cattttcctt attcaatacc    1500
taggtaggta gatgctagat tctggaaata aaatatgagt ctcaagtggt ccttgtcctc    1560
tctcccagtc aaattctgaa tctagttggc aagattctga atcaaggca tataatcagt    1620 aataag    1626
```

<210> SEQ ID NO 104
<211> LENGTH: 2332
<212> TYPE: DNA
<213> ORGANISM: Artificial Sequence
<220> FEATURE:
<223> OTHER INFORMATION: hHBB vector

<400> SEQUENCE: 104

```
ttgcatttgt aattttaaaa aatgctttct tcttttaata tacttttttg tttatcttat     60
ttctaatact ttccctaatc tctttctttc agggcaataa tgatacaatg tatcatgcct    120
ctttgcacca ttctaaagaa taacagtgat aatttctggg ttaaggcaat agcaatatct    180
ctgcatataa atatttctgc atataaattg taactgatgt aagaggtttc atattgctaa    240
tagcagctac aatccagcta ccattctgct tttattttat ggttgggata aggctggatt    300
attctgagtc caagctaggc ccttttgcta atcatgttca tacctcttat cttcctccca    360
cagctcctgg gcaacgtgct ggtctgtgtg ctggcccatc actttggcaa agaattcacc    420
ccaccagtgc aggctgccta tcagaaagtg gtggctggtg tggctaatgc cctggcccac    480
```

```
aagtatcacg gcagcggagc tactaacttc agcctgctga agcaggctgg agacgtggag    540
gagaaccctg gacctatggt gcacctcacc ccagaagaga agtctgctgt gacagctctc    600
tggggaaaag taaatgtgga tgaggtggga ggggaggccc taggaaggct tcttgttgtc    660 taccccctgga cacagagatt cttgaatcc tttggggacc tgagcactcc tgatgcagtg    720
atgggcaacc ccaaagtcaa agctcatggg aagaaggttt gggagccttt ctcagatggc    780
ctggctcacc tggacaacct gaagggcacc tttgccaccc tgtctgagct gcactgtgac    840
aagctgcatg tggaccctga aacttcagg ctcctgggca atgttctggt atgtgtgtta    900
gcacaccatt ttggcaagga attcaccct ccagtgcagg ctgcctacca gaaagtggtg    960
gcaggtgtgg ccaatgccct ggcccacaaa tatcactgag atccagacat gataagatac   1020
attgatgagt ttgacaaaac acaactaga atgcagtgaa aaaatgcttt tatttgtgaa   1080
atttgtgatg ctattgcttt atttgtaacc attataagct gcaataaaca agttaacaac   1140
aacaattgca ttcattttat gtttcaggtt caggggagg tgtgggaggt tttttaaagc   1200
tcgctttctt gctgtccaat ttctattaaa ggttcctttg ttccctaagt ccaactacta   1260
aactggggga tattatgaag ggccttgagc atctggattc tgcctaataa aaaacattta   1320
ttttcattgc aatgatgtat ttaaattatt tctgaatatt ttactaaaaa gggaatgtgg   1380
gaggtcagtg catttaaaac ataaagaaat gaagagctag ttcaaacctt gggaaaatac   1440
actatatctt aaactccatg aaagaaggtg aggctgcaaa cagctaatgc acattggcaa   1500
cagcccctga tgcatatgcc ttattcatcc ctcagaaaag gattcaagta gaggcttgat   1560
ttggaggtta aagttttgct atgctgtatt ttacattact tattgtttta gctgtcctca   1620
tgaatgtctt ttcactaccc atttgcttat cctgcatctc tcagccttga ctccactcag   1680
ttctcttgct tagagatacc acctttcccc tgaagtgttc cttccatgtt ttacggcgag   1740
atggtttctc ctcgcctggc cactcagcct tagttgtctc tgttgtctta tagaggtcta   1800
cttgaagaag gaaaaacagg ggtcatggtt tgactgtcct gtgagcccctt cttccctgcc   1860 tccccactc acagtgaccc ggaatctgca gtgctagtct cccggaacta tcactctttc   1920
acagtctgct ttggaaggac tgggcttagt atgaaaagtt aggactgaga agaatttgaa   1980
aggcggcttt ttgtagcttg atattcacta ctgtcttatt accctgtcat aggcccaccc   2040
caaatggaag tccattctt cctcaggatg tttaagatta gcattcagga agagatcaga   2100
ggtctgctgg ctcccttatc atgtccctta tggtgcttct ggctctgcag ttattagcat   2160
agtgttacca tcaaccacct taacttcatt tttcttattc aataccctagg taggtagatg   2220 ctagattctg gaaataaaat atgagtctca agtggtcctt gtcctctctc ccagtcaaat   2280
tctgaatcta gttggcaaga ttctgaaatc aaggcatata atcagtaata ag           2332
```

<210> SEQ ID NO 105
<211> LENGTH: 92
<212> TYPE: DNA
<213> ORGANISM: Artificial Sequence
<220> FEATURE:
<223> OTHER INFORMATION: Silently altered HBB coding sequence
      corresponding to HBB exon 1

<400> SEQUENCE: 105

```
atggtgcacc tcacccccaga agagaagtct gctgtgacag ctctctgggg aaaagtaaat    60
gtggatgagg tgggagggga ggccctagga ag                                   92
```

```
<210> SEQ ID NO 106
<211> LENGTH: 223
<212> TYPE: DNA
<213> ORGANISM: Artificial Sequence
<220> FEATURE:
<223> OTHER INFORMATION: Silently altered HBB coding sequence
      corresponding to HBB exon 2

<400> SEQUENCE: 106
gcttcttgtt gtctacccct ggacacagag attctttgaa tcctttgggg acctgagcac      60
tcctgatgca gtgatgggca accccaaagt caaagctcat gggaagaagg ttttgggagc     120
cttctcagat ggcctggctc acctggacaa cctgaagggc acctttgcca ccctgtctga     180
gctgcactgt gacaagctgc atgtggaccc tgagaacttc agg                       223

<210> SEQ ID NO 107
<211> LENGTH: 129
<212> TYPE: DNA
<213> ORGANISM: Artificial Sequence
<220> FEATURE:
<223> OTHER INFORMATION: Silently altered HBB coding sequence
      corresponding to HBB exon 3

<400> SEQUENCE: 107
ctcctgggca atgttctggt atgtgtgtta gcacaccatt ttggcaagga attcacccct      60
ccagtgcagg ctgcctacca gaaagtggtg gcaggtgtgg ccaatgccct ggcccacaaa    120
tatcactga                                                            129

<210> SEQ ID NO 108
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 108
aaagtcaggg cagagccatc                                                 20

<210> SEQ ID NO 109
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 109
aatgattaac ccgccatgct                                                 20

<210> SEQ ID NO 110
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 110
aactgggcat gtggagacag agaa                                            24

<210> SEQ ID NO 111
<211> LENGTH: 25
<212> TYPE: DNA
<213> ORGANISM: Artificial Sequence
<220> FEATURE:
<223> OTHER INFORMATION: Synthetic polynucleotide
```

```
<400> SEQUENCE: 111
gttacaagac aggactagta tcgat                                              25

<210> SEQ ID NO 112
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 112
tagaccaata ggcagagaga gt                                                 22

<210> SEQ ID NO 113
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 113
ctgagccaag tagaagacct tt                                                 22

<210> SEQ ID NO 114
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 114
ctgtttctgc ctggactaat ct                                                 22

<210> SEQ ID NO 115
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 115
ccctactttc taagtcacag aggct                                              25
```